US009670255B2

(12) United States Patent
Sugiyama et al.

(10) Patent No.: US 9,670,255 B2
(45) Date of Patent: Jun. 6, 2017

(54) MODIFIED BIOTIN, MUTANT STREPTAVIDIN, AND USE THEREOF

(71) Applicant: SAVID THERAPEUTICS INC., Tokyo (JP)

(72) Inventors: Akira Sugiyama, Tokyo (JP); Hirofumi Doi, Chiba (JP); Tatsuhiko Kodama, Tokyo (JP); Tsuyoshi Inoue, Osaka (JP); Eiichi Mizohata, Osaka (JP); Tatsuya Kawato, Tokushima (JP); Tomohiro Meshizuka, Osaka (JP); Motomu Kanai, Tokyo (JP); Yohei Shimizu, Tokyo (JP); Tomohiro Yamamoto, Tokyo (JP)

(73) Assignee: SAVID THERAPEUTICS INC., Tokyo (JP)

( * ) Notice: Subject to any disclaimer, the term of this patent is extended or adjusted under 35 U.S.C. 154(b) by 0 days.

(21) Appl. No.: 14/768,916

(22) PCT Filed: Feb. 18, 2014

(86) PCT No.: PCT/JP2014/053734
§ 371 (c)(1),
(2) Date: Aug. 19, 2015

(87) PCT Pub. No.: WO2014/129446
PCT Pub. Date: Aug. 28, 2014

(65) Prior Publication Data
US 2016/0137704 A1 May 19, 2016

(30) Foreign Application Priority Data
Feb. 20, 2013 (JP) ................................. 2013-031038

(51) Int. Cl.
| C07K 14/36 | (2006.01) |
| C07D 495/04 | (2006.01) |
| C07D 497/04 | (2006.01) |
| C07D 498/04 | (2006.01) |
| G01N 33/543 | (2006.01) |

(52) U.S. Cl.
CPC ............ *C07K 14/36* (2013.01); *C07D 495/04* (2013.01); *C07D 497/04* (2013.01); *C07D 498/04* (2013.01); *G01N 33/54306* (2013.01); *G01N 2333/36* (2013.01)

(58) Field of Classification Search
None
See application file for complete search history.

(56) References Cited
U.S. PATENT DOCUMENTS

| 4,529,587 | A | 7/1985 | Green |
| 5,608,060 | A | 3/1997 | Axworthy et al. |
| 5,976,535 | A | 11/1999 | Fritzberg et al. |
| 6,015,897 | A | 1/2000 | Theodore et al. |
| 6,312,916 | B1 | 11/2001 | Kopetzki et al. |
| 6,368,813 | B1 | 4/2002 | Reznik et al. |
| 6,391,571 | B1 | 5/2002 | Kopetzki et al. |
| 6,417,331 | B1 | 7/2002 | Kopetzki et al. |
| 7,249,061 | B1 | 7/2007 | Suzuki |
| 8,546,537 | B2 * | 10/2013 | Kodama .......... A61K 47/48753 530/350 |
| 2011/0081660 | A1 | 4/2011 | Orser et al. |
| 2012/0039879 | A1 | 2/2012 | Kodama et al. |

FOREIGN PATENT DOCUMENTS

| EP | 2 399 993 | 12/2011 |
| JP | 58-154508 | 9/1983 |
| JP | 9-506594 | 6/1997 |
| JP | 10-28589 | 2/1998 |
| JP | 2001-514524 | 9/2001 |
| JP | 2008-530565 | 8/2008 |
| WO | 95/15979 | 6/1995 |
| WO | 98/40396 | 9/1998 |
| WO | 2006/088823 | 8/2006 |
| WO | 2010/009455 | 1/2010 |
| WO | 2010/095455 | 8/2010 |
| WO | 2012/023579 | 2/2012 |

OTHER PUBLICATIONS

RN:29117-49-5, Chemical Abstracts Service, *STN Registry Database*, Nov. 16, 1984.
Kong et al., "Biotin-Avidin Labeling Technique," *Process in Veterinary Medicine*, vol. 29, No. 4, pp. 100-102, 2008.
Office Action issued in Chinese Application No. 201480009625.2, dated Jul. 29, 2016, along with an English translation thereof.
Revised European Search Opinion issued in EP Patent Application No. 14753647.8, dated Sep. 27, 2016.
"File Registry on STN, RN 66513-70-0", Nov. 16, 1984.
"File Registry on STN, RN 1134348-37-0", Apr. 14, 2009.
"File Registry on STN, RN 76985-52-9", Nov. 16, 1984.
"File Registry on STN, RN 39871-28-8", Nov. 16, 1984.
Green, "Avidin" *Adv. Protein Chem.*, vol. 29, pp. 85-133, 1975.
Hnatowich et al., "Investigations of Avidin and Biotin for Imaging Applications" *J. Nucl. Med.*, vol. 28, pp. 1294-1302, 1987.
Green, "Avidin and Streptavidin" *Methods in Enzymology*, vol. 184, pp. 51-67, 1990.
Paganelli et al., "Three-Step Monoclonal Antibody Tumor Targeting in Carcinoembryonic Antigen-positive Patients" *Cancer Research*, vol. 51, pp. 5960-5966, 1991.

(Continued)

*Primary Examiner* — Suzanne M Noakes
*Assistant Examiner* — Jae W Lee
(74) *Attorney, Agent, or Firm* — Greenblum & Bernstein, P.L.C.

(57) ABSTRACT

It is an object of the present invention to provide a mutant streptavidin with a reduced affinity for natural biotin, and also to provide a modified biotin having a high affinity for the mutant streptavidin with a reduced affinity for natural biotin. According to the present invention, there is provided a reagent kit for use in treatments or diagnoses, which comprises: (a) a mutant streptavidin with a reduced affinity for natural biotin or biocytin; and a modified biotin having a high affinity for the above-described mutant streptavidin.

8 Claims, 8 Drawing Sheets

(56) References Cited

OTHER PUBLICATIONS

Yasugi et al., "Biotin", Iwanami Seibutsugaku Jiten, 4th edition, Iwanami Shoten, p. 1133, Apr. 10, 1997.
Database Caplus on STN, AN 1994:72808, Abstract of Miyamoto et al., "Absolute and Relative Binding Free Energy Calculations of the Interaction of Biotin and its Analogs with Streptavidin Using Molecular Dynamics/Free Energy Perturbation Approaches" *Proteins: Structure, Function, and Genetics*, vol. 16, No. 3, pp. 226-245, 1993.
International Search Report issued in PCT/JP2014/053734, mailed Mar. 25, 2014.
International Preliminary Report on Patentability issued in PCT/JP2014/053734, mailed Sep. 3, 2015, along with an English language translation.
Mulligan et al., "Synthesis of Rabbit β-globin in Cultured Monkey Kidney Cells Following Infection with a SV40 β-globin Recombinant Genome," *Nature*, vol. 277, pp. 108-114, 1979.
Extended European Search Report issued in EP Patent Application No. 14753647.8, mailed Jul. 6, 2016.
Office Action issued in Japanese Patent Application No. 2013-031038, mailed Jan. 24, 2017, along with an English-language translation.

* cited by examiner

FIG. 5
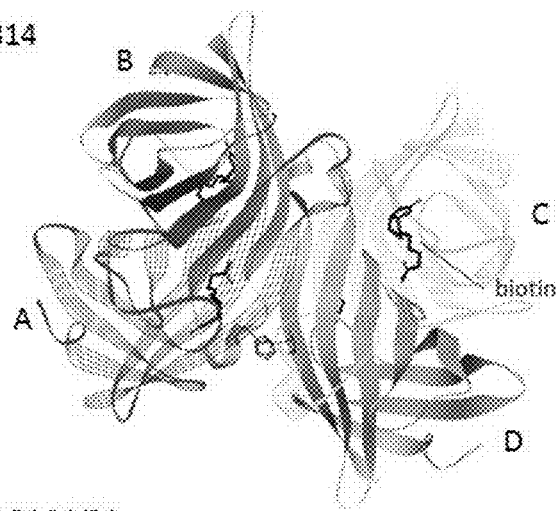
(A) LISA314
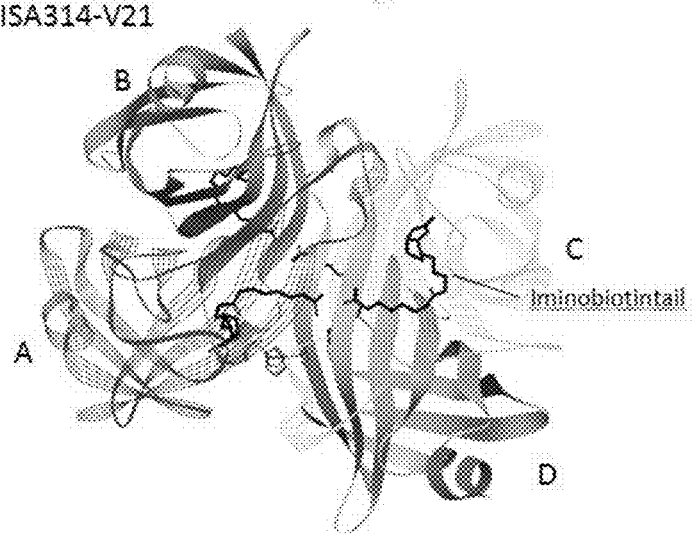
(B) LISA314-V21

D: Denatured
UD: Undenatured

SEQUENCE LISTING

```
<160> NUMBER OF SEQ ID NOS: 39

<210> SEQ ID NO 1
<211> LENGTH: 381
<212> TYPE: DNA
<213> ORGANISM: Streptomyces avidinii
<220> FEATURE:
<221> NAME/KEY: CDS
<222> LOCATION: (1)..(381)

<400> SEQUENCE: 1 gcc gaa gct ggt atc act ggc acc tgg tat aac caa ctg ggg tcg act        48
Ala Glu Ala Gly Ile Thr Gly Thr Trp Tyr Asn Gln Leu Gly Ser Thr
1               5                   10                  15 ttc att gtg acc gct ggt gcg gac gga gct ctg act ggc acc tac gaa        96
Phe Ile Val Thr Ala Gly Ala Asp Gly Ala Leu Thr Gly Thr Tyr Glu
                20                  25                  30 tct gcg gtt ggt aac gca gaa tcc cgc tac gta ctg act ggc cgt tat       144
Ser Ala Val Gly Asn Ala Glu Ser Arg Tyr Val Leu Thr Gly Arg Tyr
            35                  40                  45 gac tct gca cct gcc acc gat ggc tct ggt acc gct ctg ggc tgg act       192
Asp Ser Ala Pro Ala Thr Asp Gly Ser Gly Thr Ala Leu Gly Trp Thr
        50                  55                  60 gtg gct tgg aaa aac aac tat cgt aat gcg cac agc gcc act acg tgg       240
Val Ala Trp Lys Asn Asn Tyr Arg Asn Ala His Ser Ala Thr Thr Trp
65                  70                  75                  80 tct ggc caa tac gtt ggc ggt gct gag gct cgt atc aac act cag tgg       288
Ser Gly Gln Tyr Val Gly Gly Ala Glu Ala Arg Ile Asn Thr Gln Trp
                85                  90                  95 ctg tta aca tcc ggc act acc gaa gcg aat gca tgg aaa tcg aca cta       336
Leu Leu Thr Ser Gly Thr Thr Glu Ala Asn Ala Trp Lys Ser Thr Leu
            100                 105                 110 gta ggt cat gac acc ttt acc aaa gtt aag cct tct gct gct agc           381
Val Gly His Asp Thr Phe Thr Lys Val Lys Pro Ser Ala Ala Ser
        115                 120                 125
```

```
<210> SEQ ID NO 2
<211> LENGTH: 127
<212> TYPE: PRT
<213> ORGANISM: Streptomyces avidinii

<400> SEQUENCE: 2

Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 3
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 3

Ala Glu Ala Gly Ile Thr Gly Thr Trp Ser Asn Gln Leu Gly Ser Thr
1               5                   10                  15

Phe Ile Val Thr Ala Gly Ala Asp Gly Ala Leu Thr Gly Thr Tyr Glu
            20                  25                  30

Asn Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
65                  70                  75                  80

Ser Gly Gln Tyr Val Gly Gly Ala Asp Ala Lys Ile Asn Thr Gln Trp
                85                  90                  95

Leu Leu Thr Ser Gly Thr Thr Asn Ala Asn Ala Trp Lys Ser Thr Leu
            100                 105                 110

Val Gly His Asn Thr Phe Thr Lys Val Lys Pro Ser Ala Ala Ser
        115                 120                 125

<210> SEQ ID NO 4
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 4

Ala Glu Ala Gly Ile Thr Gly Thr Trp Ser Asp Gln Leu Gly Asp Thr
```

```
                1               5                  10                 15
Phe Ile Val Thr Ala Gly Ala Asp Gly Ala Leu Thr Gly Thr Tyr Glu
                20                   25                30

Ser Ala Val Gly Asn Ala Glu Ser Arg Tyr Val Leu Thr Gly Arg Tyr
                35                   40                45

Asp Ser Ala Pro Ala Thr Asp Gly Ser Gly Thr Ala Leu Gly Trp Thr
            50                   55                60

Val Ala Trp Lys Asn Asn Ser Lys Asn Ala His Ser Ala Thr Thr Trp
65                  70                   75                80

Ser Gly Gln Tyr Val Gly Gly Ala Asp Ala Lys Ile Asn Thr Gln Trp
                    85                   90                95

Leu Leu Thr Ser Gly Thr Thr Asn Ala Asn Ala Trp Lys Ser Thr Leu
                100                  105               110

Val Gly His Asp Thr Phe Thr Lys Val Lys Pro Ser Ala Ala Ser
                115                  120               125
```

<210> SEQ ID NO 5
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 5

```
Ala Glu Ala Gly Ile Thr Gly Thr Trp Ser Asp Gln Leu Gly Asp Thr
1               5                   10                15

Phe Ile Val Thr Ala Gly Ala Asp Gly Ala Leu Thr Gly Thr Tyr Glu
                20                  25                 30

Ala Ala Val Gly Asn Ala Glu Ser Arg Tyr Val Leu Thr Gly Arg Tyr
                35                  40                 45

Asp Ser Ala Pro Ala Thr Asp Gly Ser Gly Thr Ala Leu Gly Trp Thr
            50                  55                     60

Val Ala Trp Lys Asn Asn Ser Lys Asn Ala His Ser Ala Thr Thr Trp
65                  70                  75                 80

Ser Gly Gln Tyr Val Gly Gly Ala Asp Ala Lys Ile Asn Thr Gln Trp
                    85                  90                 95

Leu Leu Thr Ser Gly Thr Thr Asn Ala Asn Ala Trp Lys Ser Thr Leu
                100                 105                110

Val Gly His Asp Thr Phe Thr Lys Val Lys Pro Ser Ala Ala Ser
                115                 120                125
```

<210> SEQ ID NO 6
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 6

```
Ala Glu Ala Gly Ile Thr Gly Thr Trp Ser Asp Gln Leu Gly Asp Thr
1               5                   10                15

Phe Ile Val Thr Ala Gly Ala Asp Gly Ala Leu Thr Gly Thr Tyr Glu
                20                  25                 30

Gln Ala Val Gly Asn Ala Glu Ser Arg Tyr Val Leu Thr Gly Arg Tyr
                35                  40                 45

Asp Ser Ala Pro Ala Thr Asp Gly Ser Gly Thr Ala Leu Gly Trp Thr
```

```
                   50                  55                  60

Val Ala Trp Lys Asn Asn Ser Lys Asn Ala His Ser Ala Thr Thr Trp
 65                  70                  75                  80

Ser Gly Gln Tyr Val Gly Gly Ala Asp Ala Lys Ile Asn Thr Gln Trp
                 85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 7
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 7

Ala Glu Ala Gly Ile Thr Gly Thr Trp Ser Asp Gln Leu Gly Asp Thr
 1               5                  10                  15

Phe Ile Val Thr Ala Gly Ala Asp Gly Ala Leu Thr Gly Thr Tyr Glu
                20                  25                  30

Leu Ala Val Gly Asn Ala Glu Ser Arg Tyr Val Leu Thr Gly Arg Tyr
            35                  40                  45

Asp Ser Ala Pro Ala Thr Asp Gly Ser Gly Thr Ala Leu Gly Trp Thr
        50                  55                  60

Val Ala Trp Lys Asn Asn Ser Lys Asn Ala His Ser Ala Thr Thr Trp
 65                  70                  75                  80

Ser Gly Gln Tyr Val Gly Gly Ala Asp Ala Lys Ile Asn Thr Gln Trp
                 85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 8
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 8

Ala Glu Ala Gly Ile Thr Gly Thr Trp Ser Asp Gln Leu Gly Asp Thr
 1               5                  10                  15

Phe Ile Val Thr Ala Gly Ala Asp Gly Ala Leu Thr Gly Thr Tyr Glu
                20                  25                  30

Ile Ala Val Gly Asn Ala Glu Ser Arg Tyr Val Leu Thr Gly Arg Tyr
            35                  40                  45

Asp Ser Ala Pro Ala Thr Asp Gly Ser Gly Thr Ala Leu Gly Trp Thr
        50                  55                  60

Val Ala Trp Lys Asn Asn Ser Lys Asn Ala His Ser Ala Thr Thr Trp
 65                  70                  75                  80

Ser Gly Gln Tyr Val Gly Gly Ala Asp Ala Lys Ile Asn Thr Gln Trp
                 85                  90                  95

Leu Leu Thr Ser Gly Thr Thr Asn Ala Asn Ala Trp Lys Ser Thr Leu
```

```
                    100                 105                 110
Val Gly His Asp Thr Phe Thr Lys Val Lys Pro Ser Ala Ala Ser
        115                 120                 125

<210> SEQ ID NO 9
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 9

Ala Glu Ala Gly Ile Thr Gly Thr Trp Ser Asp Gln Leu Gly Asp Thr
1               5                   10                  15

Phe Ile Val Thr Ala Gly Ala Asp Gly Ala Leu Thr Gly Thr Tyr Glu
            20                  25                  30

His Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
65                  70                  75                  80

Ser Gly Gln Tyr Val Gly Gly Ala Asp Ala Lys Ile Asn Thr Gln Trp
                85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 10
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 10

Ala Glu Ala Gly Ile Thr Gly Thr Trp Ser Asp Gln Leu Gly Asp Thr
1               5                   10                  15

Phe Ile Val Thr Ala Gly Ala Asp Gly Ala Leu Thr Gly Thr Tyr Glu
            20                  25                  30

Thr Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
65                  70                  75                  80

Ser Gly Gln Tyr Val Gly Gly Ala Asp Ala Lys Ile Asn Thr Gln Trp
                85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 11
<211> LENGTH: 127
<212> TYPE: PRT
```

```
<213> ORGANISM: Artificial Sequence
<220> FEATURE:
<223> OTHER INFORMATION: Description of Artificial Sequence: Synthetic
      Recombinant polypeptide

<400> SEQUENCE: 11

Ala Glu Ala Gly Ile Thr Gly Thr Trp Ser Asp Gln Leu Gly Asp Thr
1               5                   10                  15

Phe Ile Val Thr Ala Gly Ala Asp Gly Ala Leu Thr Gly Thr Tyr Glu
            20                  25                  30

Val Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
65                  70                  75                  80

Ser Gly Gln Tyr Val Gly Gly Ala Asp Ala Lys Ile Asn Thr Gln Trp
                85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 12
<211> LENGTH: 127
<212> TYPE: PRT
<213> ORGANISM: Artificial Sequence
<220> FEATURE:
<223> OTHER INFORMATION: Description of Artificial Sequence: Synthetic
      Recombinant polypeptide

<400> SEQUENCE: 12

Ala Glu Ala Gly Ile Thr Gly Thr Trp Ser Asp Gln Leu Gly Asp Thr
1               5                   10                  15

Phe Ile Val Thr Ala Gly Ala Asp Gly Ala Leu Thr Gly Thr Tyr Glu
            20                  25                  30

Asn Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
65                  70                  75                  80

Ser Gly Gln Tyr Val Gly Gly Ala Asp Ala Lys Ile Asn Thr Gln Trp
                85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctcttcaaa gctttggccg aagctggtat cactg                              35
```

```
<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcgaggaat tcttagctag cagcagaagg cttaac                                 36

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tatgaaaacg ccgtgggtaa tgcggaa                                           27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacggcgttt tcataggtgc cggtcag                                           27

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgttggcggt gctgatgctc gtatcaacac                                        30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtgctgatg ctaagatcaa cactcagtgg                                        30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tggagcgatc agctgggcga taccttt                                           27
```

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cagctgatcg ctccaggtgc cggtaat                                27

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
aatgggtcgc ggatccgccg aagcaggtat taccggcac                   39

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ggtggtggtg ctcgaggctg gccgcgctcg gtttaacttt g                41

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
tatgaagcag ccgtgggtaa tgcggaa                                27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cacggctgct tcataggtgc cggtcag                                27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tatgaacagg ccgtgggtaa tgcggaa                                27

<210> SEQ ID NO 26

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cacggcctgt tcataggtgc cggtcag                                          27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tatgaactgg ccgtgggtaa tgcggaa                                          27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cacggccagt tcataggtgc cggtcag                                          27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tatgaaatcg ccgtgggtaa tgcggaa                                          27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacggcgatt tcataggtgc cggtcag                                          27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tatgaacatg ccgtgggtaa tgcggaa                                          27

<210> SEQ ID NO 32
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cacggcatgt tcataggtgc cggtcag                                          27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tatgaaaccg ccgtgggtaa tgcggaa                                          27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cacggcggtt tcataggtgc cggtcag                                          27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tatgaagtgg ccgtgggtaa tgcggaa                                          27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacggccact tcataggtgc cggtcag                                          27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tatgaaaacg ccgtgggtaa tgcggaa                                          27

<210> SEQ ID NO 38
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 38
cacggcgttt tcataggtgc cggtcag                                       27

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 39

His His His His His His
1               5
```

MODIFIED BIOTIN, MUTANT STREPTAVIDIN, AND USE THEREOF

The instant application contains a Sequence Listing which has been submitted electronically in ASCII format and is hereby incorporated by reference in its entirety. Said ASCII copy, created on Nov. 20, 2015, is named P48132_SL.txt and is 22,149 bytes in size.

TECHNICAL FIELD

The present invention relates to a modified biotin, a mutant streptavidin, and their use. More specifically, the present invention relates to a mutant streptavidin with a reduced affinity for natural biotin, a modified biotin having an affinity for the aforementioned mutant streptavidin, and their use.

BACKGROUND ART

Avidin and biotin, or streptavidin and biotin have an extremely high affinity (Kd=$10^{-15}$ to $10^{-14}$ M). This is one of the strongest interactions between two biomolecules. At present, the interaction between avidin/streptavidin and biotin has been widely applied in the field of biochemistry, molecular biology or medicine (Green, (1975), Adv. Protein Chem., 29: 85-133; Green, (1990), Methods Enzymol., 184: 51-67). Avidin is a basic glycoprotein derived from albumen, and its isoelectric point exceeds 10. On the other hand, streptavidin is a protein derived from one type of *Streptomyces* (*Streptomyces avidinii*). Its isoelectric point is around the neutral range, and it does not comprise a sugar chain. The two types of proteins each form a tetramer, and they each bind to a molecule of biotin per subunit. Their molecular weight is approximately 60 kDa.

In recent years, a drug delivery method involving the combination of an antibody molecule with the aforementioned high binding ability of such avidin/streptavidin and biotin, namely, a pretargeting method has been conceived (Hnatowich, (1987), J. Nucl. Med., 28, 1294-1302). However, since a chicken-derived avidin or a microorganism-derived streptavidin exhibits high immunogenicity in human bodies, it has been problematic in that an anti-avidin/streptavidin antibody is generated at an early stage after administration of such avidin/streptavidin to a human body. This is a cause that prevents the practical use of a pretargeting method (Paganelli, (1991), Cancer Res., 51, 5960-5966). In order to solve the aforementioned problem, a low immunogenic streptavidin has been reported (International Publication WO 2010/095455).

PRIOR ART LITERATURES

Patent Literatures

Patent Literature 1: International Publication WO 2010/095455

Non Patent Literatures

Non Patent Literature 1: Green, (1975), Adv. Protein Chem., 29: 85-133
Non Patent Literature 2: Green, (1990), Methods Enzymol., 184: 51-67
Non Patent Literature 3: Hnatowich, (1987), J. Nucl. Med., 28, 1294-1302
Non Patent Literature 4: Paganelli, (1991), Cancer Res., 51, 5960-5966

SUMMARY OF INVENTION

Object to be Solved by the Invention

The aforementioned low immunogenic streptavidin is characterized in that its immunogenicity to a human body is reduced. Since the low immunogenic streptavidin has an affinity for biotin existing in a human body, it is problematic in that it causes high background when used for diagnoses, or it is likely not to exhibit medicinal effects specifically on a disease when used for treatments. Thus, it is an object of the present invention to provide a mutant streptavidin with a reduced affinity for natural biotin, and to further provide a modified biotin having a high affinity for the mutant streptavidin with a reduced affinity for natural biotin. It is another object of the present invention to provide a diagnostic agent and/or a therapeutic agent, in which the combination of the above-described mutant streptavidin and the above-described modified biotin is used, and a diagnostic kit and/or a therapeutic kit, in which the combination of the above-described mutant streptavidin and the above-described modified biotin is used.

Means for Solving the Object

The present inventor has conducted intensive studies directed towards achieving the aforementioned objects. The inventor has introduced predetermined amino acid mutations into the low immunogenic mutant streptavidin described in International Publication WO 2010/095455, so that the inventor has succeeded in obtaining a mutant streptavidin with a reduced affinity for natural biotin. Simultaneously, the present inventor has modified a portion of the structure of biotin, so as to synthesize various types of modified biotins. Thereafter, the inventor has examined the affinity of the above-described mutant streptavidin for the above-described modified biotin, and as a result, the inventor has found a combination in which the mutant streptavidin and the modified biotin have an affinity for each other, thereby completing the present invention.

The present invention provides the following invention.

[1] A compound represented by the following formula (1):

[Formula 1]

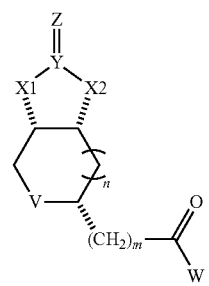

(1)

wherein X1 and X2 each independently represent O or NH; Y represents C or S; Z represents O, S or NH; V represents S or $S^+$—$O^-$; n represents an integer of 0 or 1; m represents an integer of 1 to 10; and W represents —OH, —NH(CH$_2$)$_p$COOH, or —NH(CH$_2$)$_q$C(NH$_2$)COOH, wherein p and q each independently represent an integer of 1 to 10.

[2] The compound according to [1] wherein n is 0, which is represented by the following formula (2):

[Formula 2]

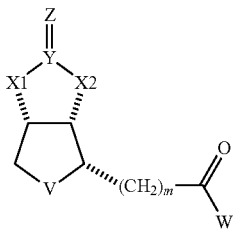

(2)

wherein X1, X2, Y, Z, V, m and W have the same definitions as those in [1].

[3] A compound represented by any one of the following formulae:

[Formula 3]

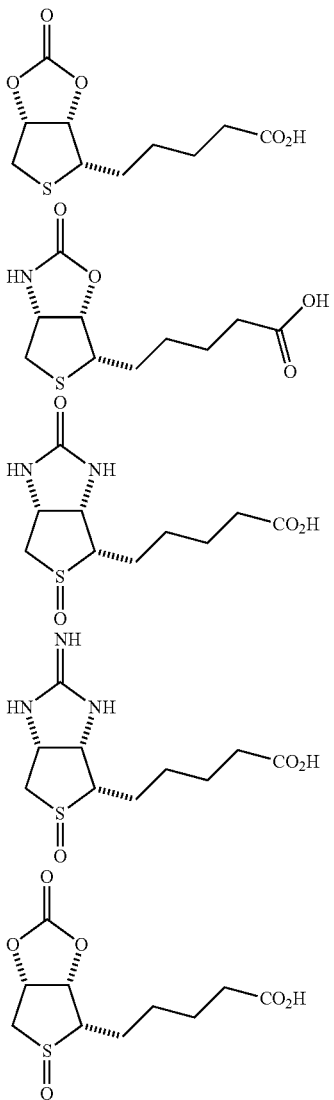

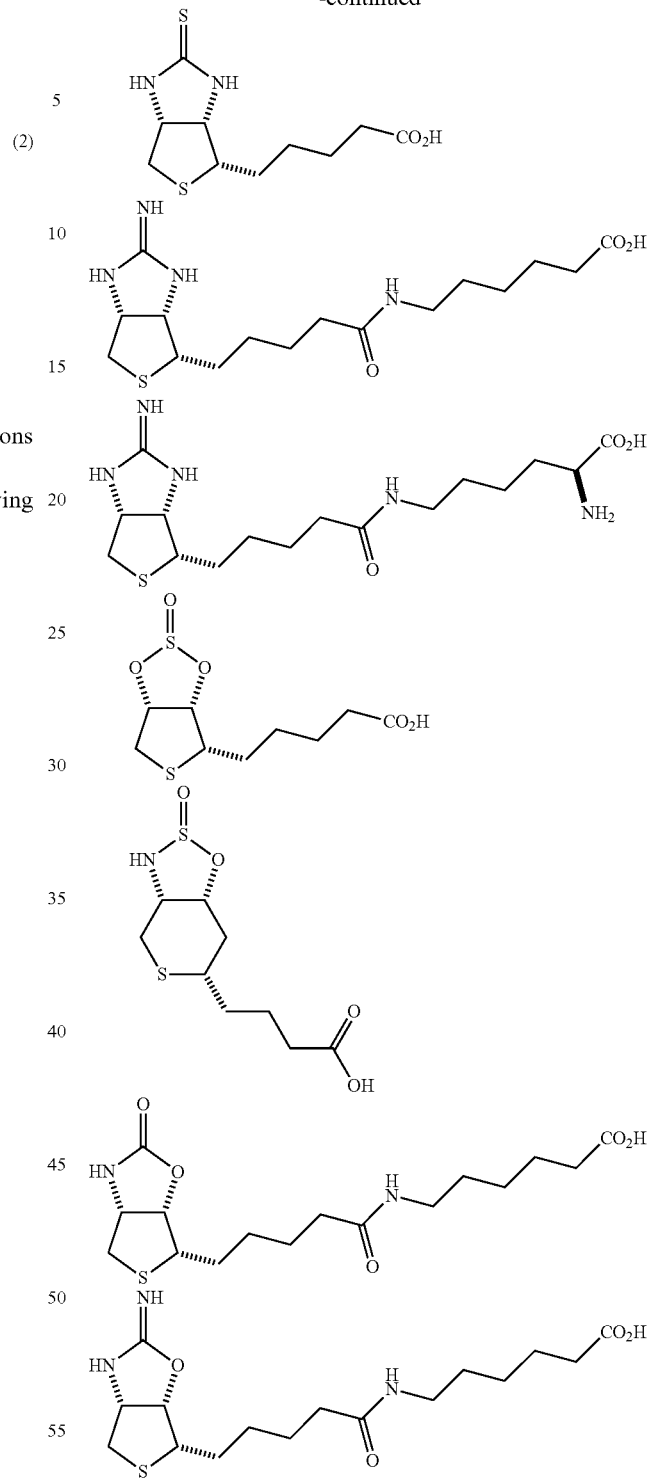

[4] A mutant streptavidin comprising the amino acid sequence shown in any one of SEQ ID NOS: 3 to 12.

[5] DNA encoding the mutant streptavidin according to [4].

[6] A mutant streptavidin-molecular probe conjugate which is obtained by conjugating a molecular probe to the mutant streptavidin according to [4].

[7] A therapeutic agent or an in-vivo or in-vitro diagnostic agent, which comprises the mutant streptavidin-molecular probe conjugate according to [6].

[8] A therapeutic, or in-vivo or in-vitro diagnostic kit, which comprises: (a) the mutant streptavidin-molecular probe conjugate according to [6]; and (b) an in-vivo or in-vitro diagnostic or therapeutic substance that has been labeled with the compound according to any one of [1] to [3].
[9] A reagent kit for use in treatments or in-vivo or in-vitro diagnoses, which comprises:
(a) a mutant streptavidin with a reduced affinity for natural biotin or biocytin; and
(b) a modified biotin having a high affinity for the above-described mutant streptavidin.
[10] A therapeutic, or in-vivo or in-vitro diagnostic kit, which comprises:
(a) a conjugate of a mutant streptavidin with a reduced affinity for natural biotin or biocytin and a molecular probe; and
(b) an in-vivo or in-vitro diagnostic or therapeutic substance that has been labeled with a modified biotin having a high affinity for the above-described mutant streptavidin.

Advantageous Effects of Invention

According to the present invention, the combination of a mutant streptavidin having a reduced affinity for natural biotin as well as a reduced immunogenicity, and a modified biotin having a high affinity for the above-described mutant streptavidin, is provided. The combination of the mutant streptavidin and the modified biotin of the present invention is useful for diagnostic methods and/or therapeutic methods, which are based on a pretargeting method.

BRIEF DESCRIPTION OF DRAWINGS

FIG. 1 discloses "6×His" as SEQ ID NO: 39.
FIG. 5 shows the crystal structures of LISA314 and LISA314-V21. (A) The co-crystal structure of LISA314 and biotin. (B) The co-crystal structure of LISA314-V21 and iminobiotin long tail. Subunits A and C are indicated by the line ribbons, and subunits B and D are indicated by the flat ribbons.

EMBODIMENTS FOR CARRYING OUT THE INVENTION

Figure 1:
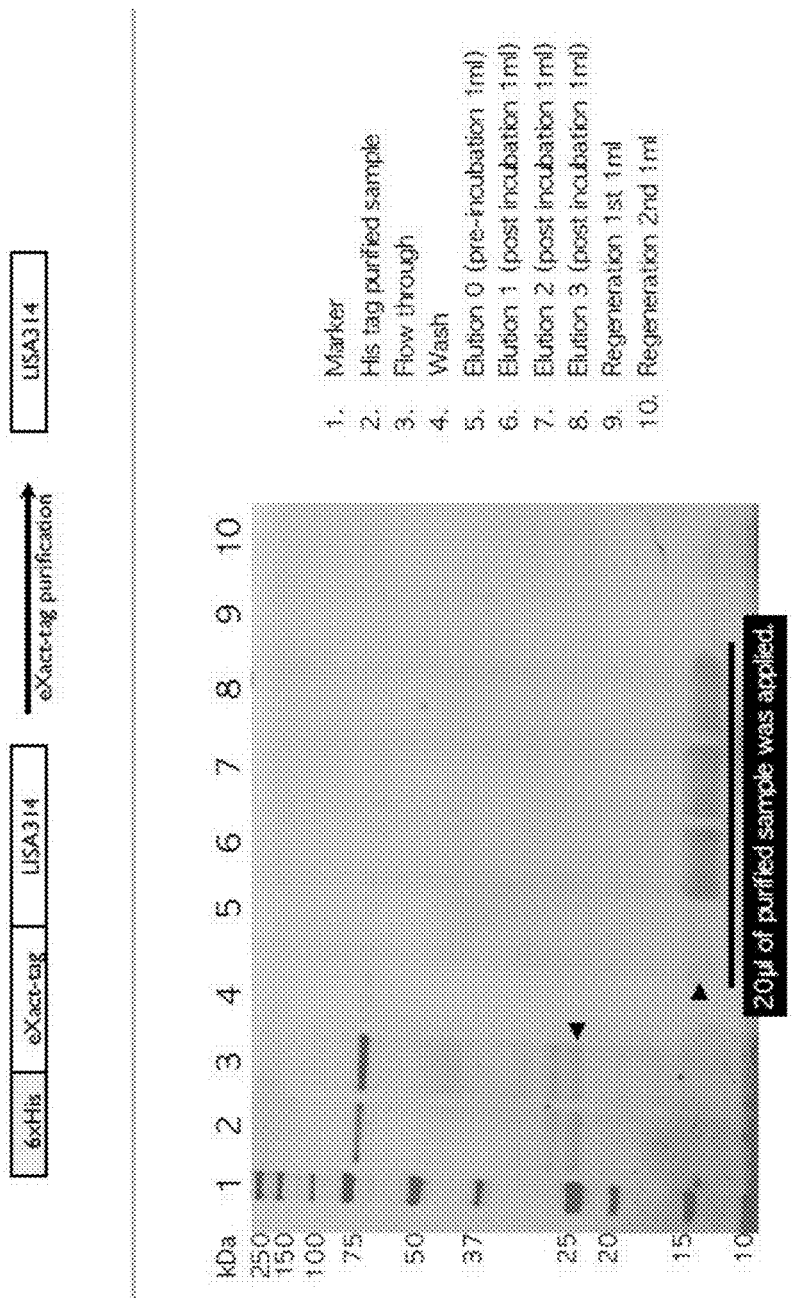
FIG. 1 shows the results of partial purification performed on a recombinant protein of a mutant streptavidin.

Hereinafter, the present invention will be described more in detail.
(1) Modified Biotin
The modified biotin of the present invention is a compound represented by the following formula (1), and preferably a compound represented by the following formula (2), wherein, in the formula (1), n is 0.

[Formula 4]

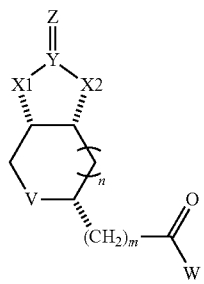

(1)

[Formula 5]

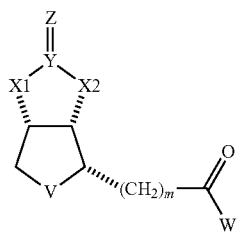

(2)

wherein X1 and X2 each independently represent O or NH; Y represents C or S; Z represents O, S or NH; V represents S or $S^+$—$O^-$; n represents an integer of 0 or 1; m represents an integer of 1 to 10; and W represents —OH, —NH(CH$_2$)$_p$COOH, or —NH(CH$_2$)$_q$C(NH$_2$)COOH, wherein p and q each independently represent an integer of 1 to 10.

In the formula (1) and the formula (2), a portion represented by the following structure:

[Formula 6]

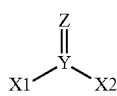

is preferably any one of the following formulae:

[Formula 7]

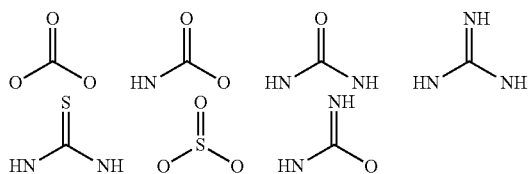

However, the aforementioned portion is not limited thereto.
m represents an integer of 1 to 10, preferably an integer of 2 to 10, more preferably an integer of 2 to 8, further preferably an integer of 2 to 6, and particularly preferably 4.
p and q each independently represent an integer of 1 to 10, preferably an integer of 2 to 10, more preferably an integer of 2 to 8, further preferably an integer of 2 to 6, and particularly preferably 4 or 5.
The compound represented by the formula (1) or formula (2) of the present invention can be synthesized by the synthetic method described in the after-mentioned Example 1. Compounds 11, 19, 21, 23, 24, 27, 29, 31, 36, 37, 46 and 47 of Example 1 are the compounds of the formula (1) or formula (2) of the present invention.

Method for Synthesizing Compound 11

2,2-dimethoxypropane and toluenesulfonic acid monohydrate are added to a DMF solution of (L)-arabinose (Compound 1) to obtain (3aS,7R,7aR)-2,2-dimethyltetrahydro-3aH-[1,3]dioxolo[4,5-c]pyran-6,7-diol (Compound 2). Compound 2 is dissolved in a mixed solvent of water and hexane, and sodium periodate is then added to the solution, followed by stirring the mixture. Thereafter, sodium carbonate is added to the reaction solution to obtain (3aS,6aS)-2,2-dimethyltetrahydrofuro[3,4-d][1,3]dioxol-4-ol (Compound 3). Celite and pyridinium dichromate are added to a DMF solution of Compound 3 to obtain (3aS,6aS)-2,2-dimethyldihydrofuro[3,4-d][1,3]dioxol-4(3aH)-one (Compound 4). Potassium thioacetate is added to a DMF solution of Compound 4 to obtain (3aS,6aR)-2,2-dimethyldihydrothieno[3,4-d][1,3]dioxol-4(3aH)-one (Compound 5). 3-Butenyl-1-magnesium bromide is added to a THF solution of Compound 5 to obtain (3aS,6aR)-4-(3-buten-1-yl)-2,2-dimethyltetrahydrothieno[3,4-d][1,3]dioxol-4-ol (Compound 6). Triethylsilane is added to a $CH_2Cl_2$ solution of Compound 6, and the mixed solution is then stirred. Thereafter, trifluoroacetic acid (675 μL, 9.05 mmol) is added to the reaction solution to obtain (2S,3S,4R)-2-(3-buten-1-yl)tetrahydrothiophene-3,4-diol (Compound 7). Pyridine and triphosgene are added to a $CH_2Cl_2$ solution of Compound 7 to obtain (3aS,4S,6aR)-4-(3-buten-1-yl)tetrahydrothieno[3,4-d][1,3]dioxol-2-one (Compound 8). Benzyl acrylate and a second generation Hoveyda-Grubbs catalyst are added to a $CH_2Cl_2$ solution containing Compound 8, and the obtained mixture is then heated to reflux to obtain (E)-benzyl5-((3aS,4S,6aR)-2-oxotetrahydrothieno[3,4-d][1,3]dioxol-4-yl)-2-pentenoate (Compound 9). Palladium carbon is added to an ethanol solution of Compound 9, and the obtained mixture is then stirred in the presence of hydrogen gas to obtain benzyl 5-((3aS,4S,6aR)-2-oxotetrahydrothieno[3,4-d][1,3]dioxol-4-yl)pentanoate (Compound 10). Boron tribromide is added to a $CH_2Cl_2$ solution containing Compound 10 to obtain ((3aS,4S,6aR)-2-oxotetrahydrothieno[3,4-d][1,3]dioxol-4-yl)pentanoic acid (Compound 11), which is represented by the formula (1) of the present invention.

Method for Synthesizing Compound 19

An n-butyllithium solution (2.6 M hexane solution) is added dropwise to an anhydrous THF solution of Compound 13, and the obtained mixture is then stirred. Thereafter, Compound 12 and a HMPA anhydrous THF solution are added dropwise to the reaction solution, and the obtained mixture is then stirred to obtain (R)-tert-butyl 4-((R)-1-hydroxy-6-(4-methyl-2,6,7-trioxabicyclo[2.2.2]octan-1-yl)-2-hexanyl-1-yl)-2,2-dimethylthiazolidine-3-carboxylate (Compound 14). A hexamethyldisilazane lithium solution is added to an anhydrous toluene solution containing Compound 14 to obtain (1R,7aR)-5,5-dimethyl-1-(5-(4-methyl-2,6,7-trioxabicyclo[2.2.2]octan-1-yl)-1-pentyn-1-yl)dihydro-1H-thiazolo[3,4-c]oxazol-3(5H)-one (Compound 15). Silver(I) nitrate is added to a mixed solution of $CH_3CN$ and $H_2O$ containing Compound 15 to obtain (E)-3-hydroxy-2-(hydroxymethyl)-2-methylpropyl 5-((3aR,6aS)-2-oxotetrahydrothieno[3,4-d]oxazol-6(6aH)-ylidene)pentanoate (Compound 16). Palladium carbon hydroxide is added to a methanol solution of Compound 16 and allyl acetate, and the mixture is stirred in the presence of hydrogen gas to obtain 3-hydroxy-2-(hydroxymethyl)-2-methylpropyl 5-((3aR,6S,6aS)-2-oxohexahydrothieno[3,4-d]oxazol-6-yl)pentanoate (Compound 18). Lithium hydroxide is added to a mixed solution of $CH_3CN$ and $H_2O$ containing Compound 18 to obtain 5-((3aR,6S,6aS)-2-oxahexahydrothieno[3,4-d]oxazol-6-yl)pentanoic acid (Compound 19).

Method for Synthesizing Compound 21

$NaBO_3 \cdot 4H_2O$ is added to an acetic acid solution of biotin (Compound 20) at room temperature, and the obtained mixture is then stirred. Thereafter, thiosodium sulfate is added to the reaction solution, and the solvent is then distilled away under reduced pressure to obtain 5-((3aS,4S,6aR)-5-oxido-2-oxohexahydro-1H-thieno[3,4-d]imidazol-4-yl)pentanoic acid (Compound 21).

Method for Synthesizing Compound 23

An $H_2O_2$ aqueous solution is added to a 1,1,1,3,3,3-hexafluoroisopropanol solution of iminobiotin (Compound 22), and a reaction is then carried out to obtain 5-((3aS,4S,6aR)-2-imino-5-oxidohexahydro-1H-thieno[3,4-d]imidazol-4-yl)pentanoic acid (Compound 23).

Method for Synthesizing Compound 24

An $H_2O_2$ aqueous solution is added to a 1,1,1,3,3,3-hexafluoroisopropanol solution of Compound 11, and a reaction is then carried out to obtain 5-((3aS,4S,6aR)-5-oxido-2-oxotetrahydrothieno[3,4-d][1,3]dioxol-4-yl)pentanoic acid (Compound 24).

Method for Synthesizing Compound 27

A Lawesson's reagent is added to a toluene solution of biotin methyl ester (Compound 25) to obtain methyl 5-((3aS,4S,6aR)-2-thioxohexahydro-1H-thieno[3,4-d]imidazol-4-yl)pentanoate (Compound 26). A sodium hydroxide aqueous solution is added to a THF solution containing Compound 26 to obtain 5-((3aS,4S,6aR)-2-thioxohexahydro-1H-thieno[3,4-d]imidazol-4-yl)pentanoic acid (Compound 27).

Method for Synthesizing Compound 29

A sodium hydroxide aqueous solution is added to a mixed solution of dioxane and $H_2O$ containing 6-aminohexanoic acid, and the pH of the solution is adjusted to approximately pH 9. Thereafter, Compound 28 is added to the resulting solution to obtain 5-((3aR,6S,6aS)-2-oxohexahydrothieno[3,4-d]oxazol-6-yl)pentanoic acid (Compound 29).

Method for Synthesizing Compound 31

A mixed solvent of dioxane and water, which contains Compound 28 and Nα-Boc-L-lysine, is stirred to obtain (S)-2-((tert-butoxycarbonyl)amino)-6-(5-((3aS,4S,6aR,Z)-2-((2,2,2-trifluoroacetyl)imino)hexahydro-1H-thieno[3,4-d]imidazol-4-yl)pentanamide)hexanoic acid (Compound 30). Compound 30 is added to a mixed solution of dioxane and $H_2O$, and hydrochloric acid is then added to the mixed solution to adjust the pH of the solution to approximately pH 3, followed by stirring the solution for 5 hours. Thereafter, the solvent is distilled away under reduced pressure. The obtained solid is dissolved in dioxane and $H_2O$, and ammonia water is then added to the solution to obtain (S)-2-amino-6-(5-((3aS,4S,6aR)-2-iminohexahydro-1H-thieno[3,4-d]imidazol-4-yl)pentanamide)hexanoic acid (Compound 31).

Method for Synthesizing Compound 36

Benzyl acrylate and a second generation Hoveyda-Grubbs catalyst are added to a $CH_2Cl_2$ solution of Compound 32 to obtain (E)-benzyl 5-((3aS,4S,6aR)-2,2-dimethyltetrahydrothieno[3,4-d][1,3]dioxol-4-yl)-2-pentenoate (Compound 33). Palladium carbon is added to an ethanol solution of Compound 33, and a reaction is then carried out in the presence of hydrogen gas to obtain benzyl 5-((3aS,4S,6aR)-2,2-dimethyltetrahydrothieno[3,4-d][1,3]dioxol-4-yl)pentanoate (Compound 34). Boron tribromide is added to a $CH_2Cl_2$ solution of Compound 34 to obtain 5-((2S,3S,4R)-3,4-dihydroxytetrahydrothiophen-2-yl)pentanoic acid (Compound 35). Thionyl chloride is added to a $CH_3CN$ solution of Compound 35 to obtain 5-((3aS,4S,6aR)-2-oxidotetrahydrothieno[3,4-d][1,3,2]dioxathiol-4-yl)pentanoic acid (Compound 36).

Method for Synthesizing Compound 37

Compound 17 is dissolved in MeOH, and the obtained mixture is then stirred using a catalytic amount of Pd/C in a hydrogen atmosphere, so as to reduce a double bond. Subsequently, the ester portion of the obtained compound is hydrolyzed with LiOH in a mixed solvent of $CH_3CN$ and $H_2O$ to obtain 4-((3aR,6S,7aR)-2-oxohexahydro-2H-thiopyrano[3,4-d]oxazol-6-yl)butanoic acid (Compound 37).

Method for Synthesizing Compound 46

Silver fluoride is added to a mixed solution of acetonitrile and water containing Compound 15, and the obtained mixture is then stirred at room temperature to obtain Compound 38. Thereafter, p-toluenesulfonic acid monohydrate is added to an anhydrous acetone solution of the triol form 38 and 2,2-dimethoxypropane, and the obtained mixture is then stirred at room temperature. Thereafter, triethylamine is added to the reaction solution, and the solvent is then distilled away under reduced pressure. The obtained crude product is purified by silica gel column chromatography to obtain Compound 39. A Pearlman catalyst (10% palladium) is added to a methanol solution of the diacetonide form 39, and the obtained mixture is then substituted with hydrogen gas (1 atmosphere, balloon), followed by performing a reaction at room temperature, to obtain a mixture of Compounds 40 and 41, in which a double bond is reduced. This crude product is dissolved in a mixed solvent of acetonitrile and water, and a 2 N lithium hydroxide aqueous solution is then added to the mixed solution, followed by stirring the mixture at room temperature, to obtain Compound 42. 1-Ethyl-3-(3-dimethylaminopropyl)carbodiimide hydrochloride is added to an N,N-dimethylformamide solution of the carboxylic acid 42 and N-hydroxysuccinimide, and the obtained mixture is then stirred at room temperature to obtain an active ester form 43. The obtained Compound 43 is dissolved in a mixed solvent of dioxane and water, and 6-aminohexanoic acid is then added to the solution, followed by stirring the mixture at room temperature, to obtain Compound 44. Thereafter, 3 N hydrochloric acid is added to a dioxane solution of the carboxylic acid 44, and the obtained mixture is then stirred at room temperature to obtain Compound 45. Potassium carbonate and carbonyldiimidazole are added to a tetrahydrofuran solution of the ammonium salt 45, and thereafter, the obtained mixture is stirred at 80° C. and is then cooled to room temperature. After that, a 2 N sodium hydroxide aqueous solution is added to the reaction solution, and the obtained mixture is then stirred at room temperature for 2 hours. Then, 2 N hydrochloric acid is added to the reaction solution, so that the solution is converted to an acidic solution (pH 3), thereby obtaining Compound 46.

Method for Synthesizing Compound 47

Sodium acetate and cyanogen bromide are added to a methanol solution of the ammonium salt 45, and the obtained mixture is then stirred at room temperature. A 2 N sodium hydroxide aqueous solution is added to the reaction solution, and the obtained mixture is then stirred at room temperature. Thereafter, water is added to the reaction solution, the aqueous layer is then washed with diethyl ether, and 2 N hydrochloric acid is then added to the solution to convert it to an acidic solution (pH 3). The solvent is distilled away under reduced pressure, and a mixed solution of dichloromethane/methanol (1:1) is added to the residue. The solid is separated and removed by filtration. The solvent is distilled away under reduced pressure, and the obtained crude product is then purified by reverse-phase HPLC to obtain Compound 47.

(2) Mutant Streptavidin

The mutant streptavidin of the present invention is characterized in that it has a certain amino acid mutation with respect to the amino acid sequence of a core streptavidin as shown in SEQ ID NO: 2 and has a reduced immunogenicity in comparison to that of a wild-type streptavidin, and also in that it has a reduced affinity for natural biotin or biocytin.

The amino acid sequence of a wild-type (natural) core streptavidin is shown in SEQ ID NO: 2 in the sequence listing, and a nucleotide sequence encoding the aforementioned amino acid sequence is shown in SEQ ID NO: 1 in the sequence listing.

The mutant streptavidin of the present invention specifically has the amino acid sequence shown in any one of SEQ ID NOS: 3 to 12 in the sequence listing.

The expression " . . . having a reduced immunogenicity in comparison to that of a wild-type streptavidin" is used in the present invention to mean that, when a mutant streptavidin is administered to a mammal such as a human, the immunogenicity of the mutant streptavidin is reduced. A reduction in the immunogenicity can be confirmed by the following method, for example. That is to say, the reactivity of the mutant streptavidin of the present invention with anti-streptavidin antiserum, which has been obtained by immunizing a crab-eating monkey with a wild-type streptavidin, is analyzed. If the reactivity of the mutant streptavidin with the aforementioned anti-streptavidin antiserum is reduced in comparison to that of the wild-type streptavidin, it can be determined that the immunogenicity of the mutant streptavidin is reduced in comparison to that of the wild-type streptavidin. When a reduction in the immunogenicity is determined by the above-described method, the immunogenicity of the mutant streptavidin of the present invention is reduced by preferably 80% or less, more preferably 60% or less, even more preferably 20% or less, further preferably 15% or less, still further preferably 10% or less, and particularly preferably 5% or less, when compared with the immunogenicity of the wild-type streptavidin.

The expression " . . . having a reduced affinity for natural biotin or biocytin" is used in the present invention to mean that the binding ability of a mutant streptavidin to natural biotin or biocytin is reduced in comparison to the binding ability of a streptavidin to natural biotin or biocytin. The affinity and/or binding ability of a mutant streptavidin to natural biotin or biocytin can be evaluated by SPR analysis or the like. When compared with a wild-type streptavidin, the affinity of the mutant streptavidin of the present invention for natural biotin or biocytin is reduced by preferably 80% or less, more preferably 70% or less, even more preferably 60% or less, further preferably 50% or less, and still further preferably 40% or less.

According to the present invention, there is further provided DNA encoding the above-described mutant streptavidin of the present invention. The DNA of the present invention can be produced by performing site-directed mutagenesis on DNA encoding a wild-type (natural) streptavidin.

The above-described DNA encoding the mutant streptavidin of the present invention can be incorporated into a vector, and it can be then used. In particular, in order to produce the mutant streptavidin of the present invention, DNA encoding the mutant streptavidin of the present invention is incorporated into an expression vector, and a host is then transformed with this expression vector, so that the mutant streptavidin of the present invention can be expressed therein.

When *Escherichia coli* is used as a host, the vector used in the present invention preferably has a replication origin (ori) and also has a gene for selecting the transformed host (e.g. a drug-resistance gene that is resistant to drugs, such as ampicillin, tetracycline, kanamycin or chloramphenicol, etc.). Moreover, an expression vector preferably has a promoter capable of efficiently expressing the mutant streptavidin of the present invention in a host, such as a lacZ promoter or a T7 promoter. Examples of such a vector include an M13 vector, a pUC vector, pBR322, pBluescript, pCR-Script, pGEX-5X-1 (Pharmacia), "QIAexpress system" (QIAGEN), pEGFP, and pET (in this case, BL21 that expresses T7 RNA polymerase is preferably used as a host). Furthermore, a signal sequence and the like may be added to such a vector, so as to increase the yield of the mutant streptavidin of the present invention.

A vector can be introduced into a host cell by applying a calcium chloride method or an electroporation method, for example. Further, a sequence that encodes a tag for improving solubility, such as glutathione S-transferase, thioredoxin or a maltose-binding protein, may be added. Still further, a sequence that encodes a tag designed for facilitating purification, such as a polyhistidine tag, a Myc epitope, a hemagglutinin (HA) epitope, a T7 epitope, an Xpress tag, a FLAG tag or other known tag sequences, may also be added.

Other than *Escherichia coli*, examples of an expression vector include: mammal-derived expression vectors (for example, pcDNA3 (manufactured by Invitrogen), pEGF-BOS (Nucleic Acids. Res. 1990, 18(17), p. 5322), pEF and pCDM8); insect cell-derived expression vectors (for example, "Bac-to-BAC baculovirus expression system" (manufactured by Gibco-BRL) and pBacPAK8); plant-derived expression vectors (for example, pMH1 and pMH2); animal virus-derived expression vectors (for example, pHSV, pMV and pAdexLcw); retrovirus-derived expression vectors (for example, pZIPneo); yeast-derived expression vectors (for example, "*Pichia* Expression Kit" (manufactured by Invitrogen), pNV11 and SP-Q01); *Bacillus subtilis*-derived expression vectors (for example, pPL608 and pKTH50).

When the expression of the present mutant streptavidin in an animal cell such as a CHO cell, a COS cell or an NIH3T3 cell is intended, it is essential for the expression vector to have a promoter necessary for the expression of the mutant streptavidin in such an animal cell, such as an SV40 promoter (Mulligan et al., Nature (1979) 277, 108), an MMLV-LTR promoter, an EF1α promoter (Mizushima et al., Nucleic Acids Res. (1990) 18, 5322) or a CMV promoter. It is more preferable if the expression vector has a gene for selecting the transformation of a cell (for example, a drug-resistance gene capable of determining transformation with the use of drugs (neomycin, G418, etc.)). Examples of a vector having such properties include pMAM, pDR2, pBK-RSV, pBK-CMV, pOPRSV and pOP13.

The type of a host cell, into which a vector is introduced, is not particularly limited. Either prokaryotes or eukaryotes may be used. It is possible to use *Escherichia coli* or various types of animal cells, for example.

In the case of using a eukaryotic cell, for example, an animal cell, a plant cell or a fungal cell can be used as a host. Examples of an animal cell that can be used herein include: mammalian cells such as a CHO cell, a COS cell, a 3T3 cell, a HeLa cell or a Vero cell; and insect cells such as Sf9, Sf21 or Tn5. When the expression of a large amount of the mutant streptavidin in an animal cell is intended, a CHO cell is particularly preferable. A vector can be introduced into a host cell by a calcium phosphate method, a DEAE-dextran method, a method using cationic ribosome DOTAP (manufactured by Boehringer Mannheim), an electroporation method, a lipofection method or the like.

As a plant cell, a cell from *Nicotiana tabacum* has been known as a protein-producing system, for example. These cells may be subjected to callus culture. Examples of a known fungal cell include: yeast cells including genus *Saccharomyces* such as *Saccharomyces cerevisiae*; and filamentous fungi including genus *Aspergillus* such as *Aspergillus niger*.

Examples of a procaryotic cell that can be used herein include *Escherichia coli* (*E. coli*), such as JM109, DH5α or HB101. Moreover, *Bacillus subtilis* has been known.

These cells are transformed with the DNA of the present invention, and the transformed cells are then cultured in vitro, so as to obtain the mutant streptavidin of the present invention. The culture can be carried out in accordance with a known culture method. Examples of a culture solution of animal cells that can be used herein include DMEM, MEM, RPMI1640, and IMDM. During the culture, a serum infusion such as fetal calf serum (FCS) may be used in combination, or serum free culture may also be carried out. The pH applied during the culture is preferably approximately pH 6 to 8. The culture is generally carried out at a temperature of approximately 30° C. to 40° C. for approximately 15 to 200 hours. As necessary, medium replacement, ventilation and stirring are carried out. Furthermore, growth factors may also be added to promote the growth of cells.

(3) Use of Mutant Streptavidin and Modified Biotin

Moreover, according to the present invention, there are provided: a mutant streptavidin-molecular probe conjugate, which is obtained by binding a molecular probe to the mutant streptavidin of the present invention; and a therapeutic or diagnostic agent comprising the mutant streptavidin-molecular probe conjugate. Furthermore, the above-described mutant streptavidin-molecular probe conjugate is combined with a diagnostic or therapeutic substance that has been labeled with a modified biotin having an affinity for the mutant streptavidin of the present invention, so that it can be provided as a therapeutic or diagnostic kit. Examples of the molecular probe used herein include an antibody, a peptide, a nucleic acid, and an aptamer.

Specifically, in the present invention, a fusion body of a molecular probe such as a tumor antigen-specific antibody molecule and the mutant streptavidin of the present invention is prepared, and the prepared fusion body is then administered to a patient, so that the mutant streptavidin of the present invention can be accumulated specifically in cancer cells. Subsequently, a diagnostic or therapeutic substance (a fluorochrome, a chemiluminescent agent, a radioisotope, a sensitizer consisting of a metal compound or the like, a neutron-capturing agent consisting of a metal compound or the like, a low-molecular-weight compound, micro- or nano-bubbles, a protein, etc.) that has been bound to a modified biotin having an affinity for the above-described mutant streptavidin is administered to a patient, so that the substance can be accumulated exactly in cancer cells. In the present invention, the generation of an antibody is suppressed by a reduction in immunogenicity, and thereby, the clearance of the mutant streptavidin from the body in an early stage caused by the antibody, or shock such as anaphylaxis, can be prevented. Moreover, in the present invention, using the mutant streptavidin of the present invention as an in-vitro diagnostic agent or a clinical diagnostic agent, regarding which the tissue, serum and the like collected from patients are used, noise derived from biotin or a biotin-binding protein present in the tissue, serum and the like can be reduced, and thereby, diagnosis and examination with a higher S/N ratio can be carried out.

Various types of molecules can be used as antibodies that are to be bound to the mutant streptavidin. Either a polyclonal antibody or a monoclonal antibody may be used. The subclass of the antibody is not particularly limited. Preferably, IgG, and particularly preferably, $IgG_1$ is used. Furthermore, the term "antibody" includes all of modified antibodies and antibody fragments. Examples of such an antibody include: a humanized antibody; a human type antibody; a human antibody; antibodies from various types of animals such as a mouse, a rabbit, a rat, a guinea pig and a monkey; a chimeric antibody of a human antibody and an antibody from a different type of animal; diabody; scFv; Fd; Fab; Fab'; and $F(ab)'_2$. However, examples are not limited thereto.

The conjugate of the mutant streptavidin and the antibody can be obtained by applying a method known to persons skilled in the art. For example, such a conjugate can be obtained by a chemical bond method (U.S. Pat. No. 5,608,060). Alternatively, DNA encoding the mutant streptavidin is ligated to DNA encoding an antibody, and using an expression vector or the like, the ligated DNA is then expressed in a host cell, so that such a conjugate can be obtained in the form of a fusion protein. The DNA encoding the mutant streptavidin may be ligated to the DNA encoding an antibody via DNA encoding a suitable peptide, called a linker. The mutant streptavidin-molecular probe conjugate is desirably produced, while keeping the specific binding ability between an antibody and a target molecule.

According to the present invention,
a therapeutic or diagnostic reagent kit, which comprises:
(a) a mutant streptavidin with a reduced affinity for natural biotin or biocytin; and
(b) a modified biotin having a high affinity for the above-described mutant streptavidin, and
a therapeutic or diagnostic kit, which comprises:
(a) a conjugate of a mutant streptavidin with a reduced affinity for natural biotin or biocytin and a molecular probe; and
(b) a diagnostic or therapeutic substance that has been labeled with a modified biotin having a high affinity for the above-described mutant streptavidin, are provided.

Specific examples of the mutant streptavidin with a reduced affinity for natural biotin or biocytin include:
a mutant streptavidin, which has all of the following mutations (1) to (6), with respect to a streptavidin having the amino acid sequence shown in SEQ ID NO: 2:
(1) a mutation, in which the tyrosine residue at position 10 is substituted with serine;
(2) a mutation, in which the tyrosine residue at position 71 is substituted with serine;
(3) a mutation, in which the arginine residue at position 72 is substituted with lysine;
(4) a mutation, in which the glutamic acid residue at position 89 is substituted with aspartic acid;
(5) a mutation, in which the arginine residue at position 91 is substituted with lysine; and
(6) a mutation, in which the glutamic acid residue at position 104 is substituted with asparagine; and also has the following mutations (7) and (8):
(7) a mutation, in which the serine residue at position 33 is substituted with another amino acid (for example, asparagine); and (8) a mutation, in which the aspartic acid residue at position 116 is substituted with another amino acid (for example, asparagine), and also,
a mutant streptavidin, which has all of the above mutations (1) to (6), and also has the following mutations (7') and (8'):
(7') a mutation, in which the asparagine residue at position 11 is substituted with another amino acid (for example, aspartic acid); and
(8') a mutation, in which the serine residue at position 15 is substituted with another amino acid (for example, aspartic acid).

Another example of the mutant streptavidin that can be used herein is:
a mutant streptavidin, which has all of the following mutations (1) to (8'), with respect to a streptavidin having the amino acid sequence shown in SEQ ID NO: 2:
(1) a mutation, in which the tyrosine residue at position 10 is substituted with serine;
(2) a mutation, in which the tyrosine residue at position 71 is substituted with serine;
(3) a mutation, in which the arginine residue at position 72 is substituted with lysine;
(4) a mutation, in which the glutamic acid residue at position 89 is substituted with aspartic acid;
(5) a mutation, in which the arginine residue at position 91 is substituted with lysine; and
(6) a mutation, in which the glutamic acid residue at position 104 is substituted with asparagine;
(7') a mutation, in which the asparagine residue at position 11 is substituted with another amino acid (for example, aspartic acid); and
(8') a mutation, in which the serine residue at position 15 is substituted with another amino acid (for example, aspartic acid), and further has the following mutation (9):
(9) a mutation, in which the serine residue at position 33 is substituted with another amino acid (for example, alanine, glutamine, leucine, isoleucine, histidine, threonine, valine, or asparagine).

As a modified biotin having a high affinity for the above-described mutant streptavidin, the compound represented by the formula (1) as described in the present description (preferably, the compound represented by the formula (2)) can be used.

The present invention will be more specifically described in the following examples. However, these examples are not intended to limit the scope of the present invention.

EXAMPLES

Example 1: Synthesis of Modified Biotin

General Method: The NMR spectrum was recorded using a JEOL JNM-LA500 or ECX500 spectrometer (500 MHz for $^1H$ NMR, and 125.65 MHz for $^{13}C$ NMR). The chemical shift was reported in a δ scale to the remaining $CHCl_3$ (δ=7.26 for $^1H$ NMR, and δ=77.0 for $^{13}C$ NMR) used as an internal reference, at a unit of ppm. The ESI mass spectrum was measured by Waters-ZQ4000. Column chromatography was carried out using silica gel Merk 60 (230-400 mesh ASTM) or silica gel 60 N (KANTO CHEMICAL, spherical, neutral, 40-100 μm). Anhydrous tetrahydrofuran (THF) was purchased from Kanto Chemical. Co., Inc., or it was newly distilled from $Ph_2CO$—Na. With regard to other reagents, commercially available products were directly used, unless otherwise specified.

(3aS,7R,7aR)-2,2-Dimethyltetrahydro-3aH-[1,3]dioxolo[4,5-c]pyran-6,7-diol (2)

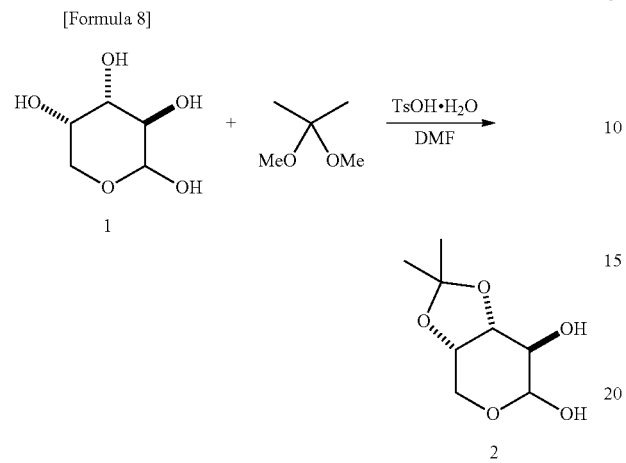

2,2-Dimethoxypropane (10 mL, 81.6 mmol) and toluenesulfonic acid monohydrate (60 mg, 0.32 mmol) were added to a DMF (30 mL) solution of (L)-arabinose (4 g, 26.6 mmol) at room temperature. The obtained mixture was stirred for 12 hours, and thereafter, sodium carbonate was added to the reaction solution to neutralize it. After completion of filtration, the solvent was distilled away under reduced pressure to obtain a crude product containing Compound 2. The routine proceeded to the following reaction without performing further purification.

(3aS,6aS)-2,2-Dimethyltetrahydrofuro[3,4-d][1,3]dioxol-4-ol (3)

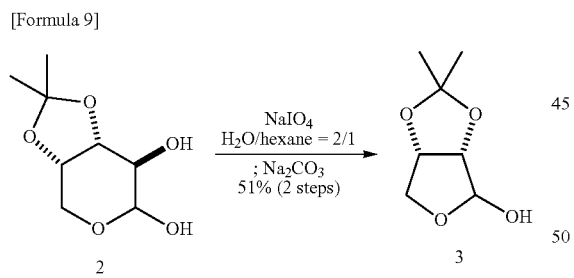

The crude product containing Compound 2 was dissolved in a mixed solvent of water (40 mL) and hexane (20 mL), and sodium periodate (14.2 g, 66.5 mmol) was then added to the solution, followed by stirring the obtained mixture for 2 hours. Thereafter, sodium carbonate was added to the reaction solution, and the obtained mixture was further stirred for 1 hour. Thereafter, water was added to the reaction solution, and the mixture was then extracted with ethyl acetate. The organic layer was washed with brine and was then dried, and the solvent was then distilled away under reduced pressure. The obtained crude product was purified by silica gel column chromatography (dichloromethane-methanol), so as to obtain 2.17 g of the title compound (two-step yield: 51%).

$^1$H NMR (CDCl$_3$): δ=1.32 (s, 3H), 1.47 (s, 3H), 4.02 (d, J=10 Hz, 1H), 4.08 (dd, J=10, 3.7 Hz, 1H), 4.58 (d, J=5.8 Hz, 1H), 4.84 (dd, J=5.8, 3.7 Hz, 1H), 5.42 (s, 1H)

(3aS,6aS)-2,2-Dimethyldihydrofuro[3,4-d][1,3]dioxol-4(3aH)-one (4)

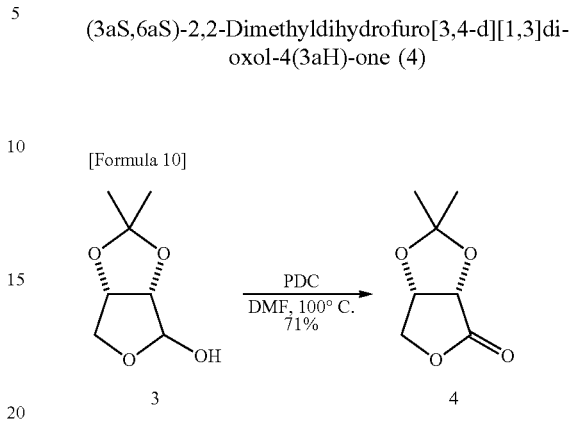

Celite and pyridinium dichromate (5 g, 18.5 mmol) were added to a DMF (20 mL) solution of Compound 3 (740 mg, 4.60 mmol), and the obtained mixture was then stirred at 100° C. for 12 hours. Thereafter, the reaction solution was cooled, and it was then passed through a Florisil short column (ethyl acetate). The solvent was distilled away under reduced pressure, and the obtained crude product was then purified by silica gel column chromatography (dichloromethane-methanol), so as to obtain 520 mg of the title compound (yield: 71%).

$^1$H NMR (CDCl$_3$): δ=1.40 (s, 3H), 1.48 (s, 3H), 4.40 (dd, J=11, 3.7 Hz, 1H), 4.46 (d, J=11 Hz, 1H), 4.74 (d, J=5.8 Hz, 1H), 4.87 (dd, J=5.8, 3.7 Hz, 1H)

(3aS,6aR)-2,2-Dimethyldihydrothieno[3,4-d][1,3]dioxol-4(3aH)-one (5)

[Formula 11]

Potassium thioacetate (1 g, 9.00 mmol) was added to a DMF (40 mL) solution of Compound 4 (1.3 g, 8.22 mmol), and the obtained mixture was then stirred at room temperature for 3 hours. Thereafter, cold water was added to the reaction solution to quench the reaction, and the reaction solution was then extracted with ether. The organic layer was washed with brine and was then dried, and the solvent was then distilled away under reduced pressure. The obtained crude product was purified by silica gel column chromatography (hexane-ethyl acetate), so as to obtain 500 mg of the title compound (yield: 35%, a brown solid).

$^1$H NMR (CDCl$_3$): δ=1.36 (s, 3H), 1.44 (s, 3H), 3.49 (d, J=13 Hz, 1H), 3.60 (dd, J=13, 4.6 Hz, 1H), 4.56 (d, J=4.9 Hz, 1H), 4.81 (dd, J=4.9, 4.6 Hz, 1H)

(3aS,6aR)-4-(3-Buten-1-yl)-2,2-dimethyltetrahydrothieno[3,4-d][1,3]dioxol-4-ol (6)

[Formula 12]

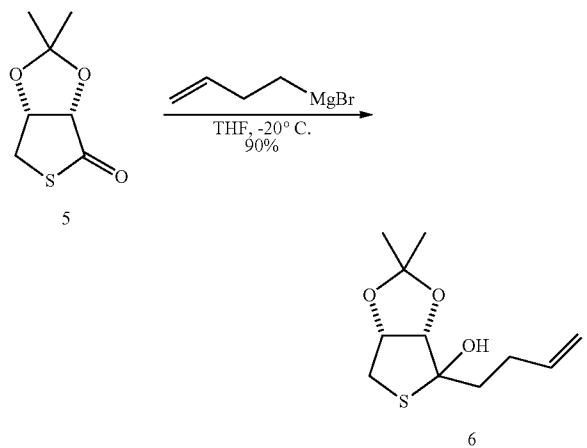

3-Butenyl-1-magnesium bromide (6.05 mmol) was added to a THF (40 mL) solution of Compound 5 (350 mg, 2.01 mmol), and the obtained mixture was then stirred at −20° C. for 30 minutes. Thereafter, a saturated ammonium chloride aqueous solution was added to the reaction solution to quench the reaction, and the reaction solution was then extracted with ethyl acetate. The organic layer was washed with brine and was then dried, and the solvent was then distilled away under reduced pressure. The obtained crude product was purified by silica gel column chromatography (hexane-ethyl acetate), so as to obtain 417 mg of the title compound (yield: 90%, a light yellow oily substance).

$^1$H NMR (CDCl$_3$): δ=1.31 (s, 3H), 1.50 (s, 3H), 2.05 (t, J=7.3 Hz, 2H), 2.05 (m, 2H), 2.90 (d, J=13 Hz, 1H), 3.27 (dd, J=13, 4.3 Hz, 1H), 4.38 (d, J=5.5 Hz, 1H), 5.01 (d, J=10 Hz, 1H), 5.12 (d, J=17 Hz, 1H), 5.85-5.94 (m, 1H)

(2S,3S,4R)-2-(3-Buten-1-yl)tetrahydrothiophene-3,4-diol (7)

[Formula 13]

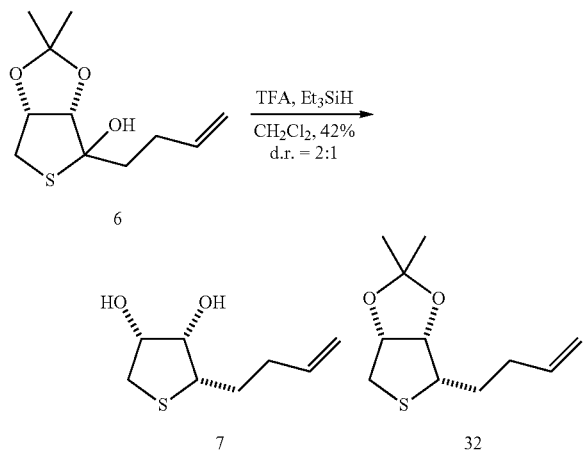

Triethylsilane (2.9 mL, 18.1 mmol) was added to a CH$_2$Cl$_2$ (8 mL) solution of Compound 6 (417 mg, 1.81 mmol) at 0° C., and the obtained mixture was then stirred for 15 minutes. Thereafter, trifluoroacetic acid (675 μL, 9.05 mmol) was added to the reaction solution, and the obtained mixture was then stirred for 12 hours. Thereafter, saturated sodium bicarbonate aqueous solution was added to the reaction mixture to quench the reaction, and the mixture was then extracted with ethyl acetate. The organic layer was washed with brine and was then dried, and the solvent was then distilled away under reduced pressure. The obtained crude product was purified by silica gel column chromatography (hexane-ethyl acetate), so as to obtain 130 mg of the title compound (yield: 42%, a light yellow solid). Also, Compound 32 (yield: 25%) was obtained as a by-product.

Compound 7: $^1$H NMR (CDCl$_3$): δ=1.65-1.74 (m, 1H), 1.89-1.96 (m, 1H), 2.05-2.19 (m, 2H), 2.81 (dd, J=10, 8.8 Hz, 1H), 3.03 (dd, J=10, 7.1 Hz, 1H), 3.39-3.45 (m, 1H), 4.10 (t, J=3.5 Hz, 1H), 4.28-4.33 (m, 1H), 5.00 (d, J=10 Hz, 1H), 5.06 (d, J=17 Hz, 1H), 5.75-5.84 (m, 1H)

Compound 32: $^1$H NMR (CDCl$_3$): δ=1.32 (s, 3H), 1.51 (s, 3H), 1.75-1.84 (m, 1H), 1.89-1.97 (m, 1H), 2.15-2.23 (m, 2H), 2.82 (dd, J=13, 4.0 Hz, 1H), 2.86 (d, J=12 Hz, 1H), 3.10-3.12 (m, 1H), 4.60 (t, J=4.3 Hz, 1H), 4.84 (t, J=5.5 Hz, 1H), 5.00 (d, J=9.0 Hz, 1H), 5.07 (d, J=16 Hz, 1H), 5.78-5.87 (m, 1H)

(3aS,4S,6aR)-4-(3-Buten-1-yl)tetrahydrothieno[3,4-d][1,3]dioxol-2-one (8)

[Formula 14]

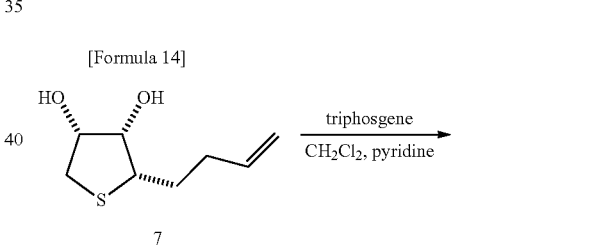

Pyridine (8 μL, 0.10 mmol) and triphosgene (15.3 mg, 0.052 mmol) were added to a CH$_2$Cl$_2$ (600 μL) solution of Compound 7 (6 mg, 0.034 mmol) at 0° C. The obtained mixture was stirred for 30 minutes, and saturated sodium bicarbonate aqueous solution was then added to the reaction mixture to quench the reaction. Then, the resulting mixture was extracted with ethyl acetate. The organic layer was washed with brine and was then dried, and the solvent was then distilled away under reduced pressure. The obtained crude product was used in the subsequent reaction without being subjected to a further purification operation.

(E)-Benzyl 5-((3aS,4S,6aR)-2-oxotetrahydrothieno[3,4-d][1,3]dioxol-4-yl)-2-pentenoate (9)

[Formula 15]

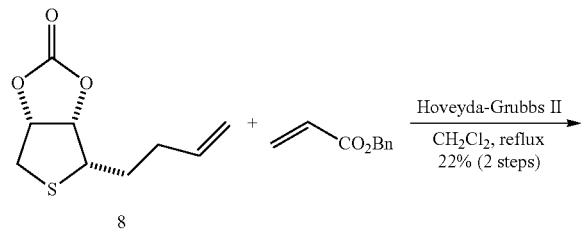

Benzyl acrylate (51 µL, 0.34 mmol) and a second generation Hoveyda-Grubbs catalyst (2.1 mg, 3.4 µmol) were added to a CH$_2$Cl$_2$ (600 µL) solution of the crude product containing Compound 8, and the obtained mixture was then heated to reflux for 12 hours. Thereafter, the solvent was distilled away under reduced pressure, and the obtained crude product was then purified by silica gel column chromatography (hexane-ethyl acetate), so as to obtain 2.6 mg of the title compound (two-step yield: 23%, a light yellow oily substance).

$^1$H NMR (CDCl$_3$): δ=1.93-2.02. (m, 1H), 2.03-2.10 (m, 1H), 2.31-2.45 (m, 2H), 2.96 (dd, J=14, 4.3 Hz, 1H), 3.14 (d, J=14 Hz, 1H), 3.19-3.23 (m, 1H), 5.03 (dd, J=6.4, 4 Hz, 1H), 5.18 (s, 2H), 5.27 (dd, J=6.4, 4.3 Hz, 1H), 5.95 (d, J=15 Hz, 1H), 6.97 (dt, J=15, 7 Hz, 1H), 7.32-7.36 (m, 2H), 7.37 (d, J=4.6 Hz, 3H)

Benzyl 5-((3aS,4S,6aR)-2-oxotetrahydrothieno[3,4-d][1,3]dioxol-4-yl)pentanoate (10)

[Formula 16]

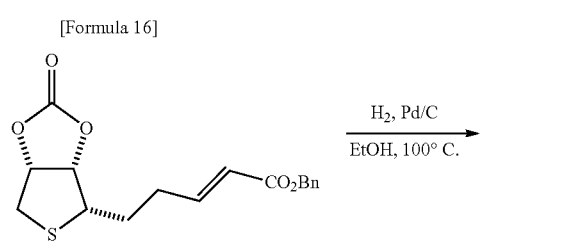

Palladium carbon (10 w/w % Pd, 15 mol %, 1.0 mg) was added to an EtOH (1 mL) solution of Compound 9. The obtained mixture was stirred in the presence of hydrogen gas (30 atm) at 100° C. for 3 hours. Thereafter, the reaction solution was cooled to room temperature, and passed through a Celite short column (ethanol). The solvent was distilled away under reduced pressure. The obtained crude product was used in the subsequent reaction without being subjected to a further purification operation.

(3aS,4S,6aR)-2-Oxotetrahydrothieno[3,4-d][1,3]dioxol-4-yl)pentanoic acid (11)

[Formula 17]

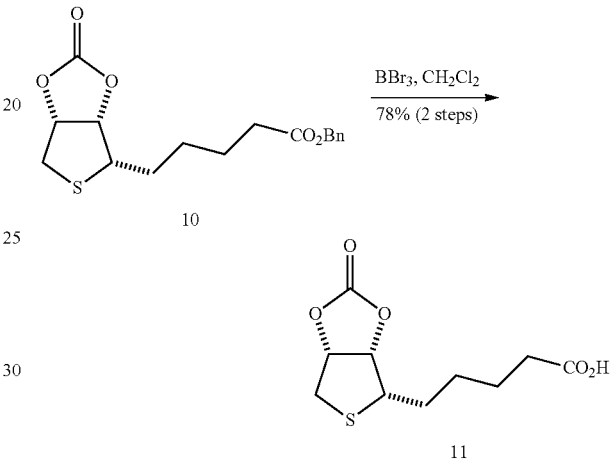

1 M boron tribromide (50 µL, 0.050 mmol) was added to a CH$_2$Cl$_2$ (600 µL) solution of the crude product containing Compound 10 at −78° C. The obtained mixture was stirred at 0° C. for 3 hours. Thereafter, a saturated ammonium chloride aqueous solution was added to the reaction solution, and the obtained mixture was then extracted with ethyl acetate. The organic layer was washed with brine and was then dried, and the solvent was then distilled away under reduced pressure. The obtained crude product was purified by silica gel column chromatography (dichloromethane-methanol), so as to obtain 1.5 mg of the title compound (yield: 78%, a white solid).

$^1$H NMR (CDCl$_3$): δ=1.50-1.55 (m, 2H), 1.70 (q, J=7.3 Hz, 2H), 1.74-1.84 (m, 1H), 1.88-1.95 (m, 1H), 2.39 (t, J=7.4 Hz, 1H), 2.96 (dd, J=14, 4.3 Hz, 1H), 3.14 (d, J=14 Hz, 1H), 3.22 (ddd, J=8.0, 6.7, 4.0 Hz, 1H), 5.05 (dd, J=6.4, 4.0 Hz, 1H), 5.28 (dd, J=6.4, 3.7 Hz, 1H)

(3-Methyloxyethan-3-yl)methyl-5-hexynoate (40)

[Formula 18]

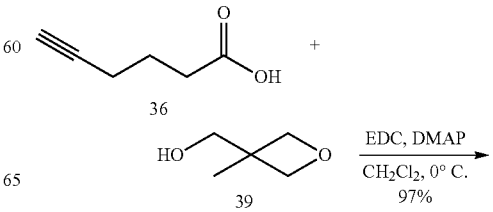

-continued

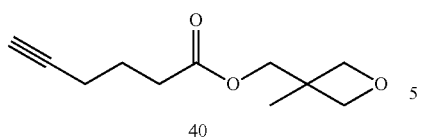

40

1-Ethyl-3-(3-dimethylaminopropyl)carbodiimide hydrochloride (10.3 g, 53.5 mmol) and N,N-dimethyl-4-aminopyridine (545 mg, 4.46 mmol) were added to a CH$_2$Cl$_2$ (20 mL) solution of the 5-hexynoic acid 38 (5 mL, 44.6 mmol) and 3-methyl-3-oxetane methanol 39 (4.5 mL, 44.6 mmol) at 0° C. The obtained mixture was stirred under cooling on ice for 1 hour. After that, water and brine were added to the reaction solution, and the obtained mixture was then extracted with CH$_2$Cl$_2$. The organic layer was washed with brine and was then dried, and the solvent was then distilled away under reduced pressure. The obtained crude product was purified by silica gel column chromatography (hexane-ethyl acetate), so as to obtain 8.5 g of the title compound (yield: 97%, a colorless oily substance).

$^1$H NMR (CDCl$_3$): δ=1.33 (s, 3H), 1.83-1.89 (m, 2H), 2.04 (s, 1H), 2.27 (td, J=6.9, 2.9 Hz, 2H), 2.51 (t, J=7.5 Hz, 2H), 4.17 (s, 2H), 4.38 (d, J=5.7 Hz, 2H), 4.51 (d, J=5.7 Hz, 2H)

4-Methyl-1-(4-pentyl-1-yl)-2,6,7-trioxabicyclo[2.2.2]octane (13)

[Formula 19]

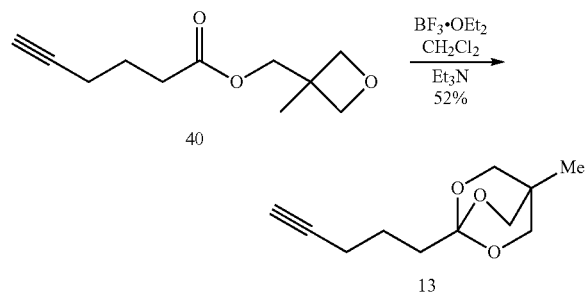

Boron trifluoride diethyl ether complex (2.7 mL, 21.7 mmol) was added dropwise to a CH$_2$Cl$_2$ (40 mL) solution of Compound 40 (8.5 g, 43.3 mmol) at 0° C. The obtained mixture was stirred at room temperature for 12 hours. Thereafter, triethylamine (8 mL) was added dropwise to the reaction solution at 0° C., and the obtained mixture was then stirred at room temperature for 1 hour. Thereafter, the reaction solution was purified by silica gel column chromatography (hexane-ethyl acetate-triethylamine), so as to obtain 4.4 g of the title compound (yield: 52%, a colorless oily substance).

$^1$H NMR (CDCl$_3$): δ=0.79 (s, 3H), 1.66-1.72 (m, 2H), 1.77-1.80 (m, 2H), 2.16 (s, 1H), 2.21 (td, J=6.9, 2.9 Hz, 2H), 3.88 (s, 6H)

(R)-tert-Butyl 4-((R)-1-hydroxy-6-(4-methyl-2,6,7-trioxabicyclo[2.2.2]octan-1-yl)-2-hexanyl-1-yl)-2,2-dimethylthiazolidine-3-carboxylate (14)

[Formula 20]

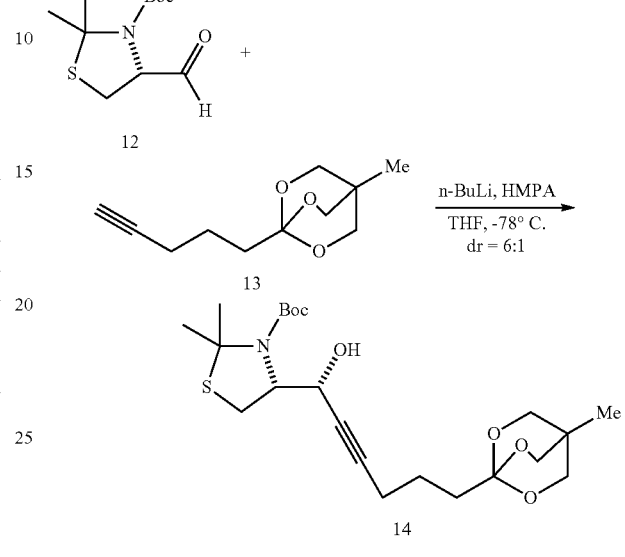

An n-butyllithium solution (15 mL of 2.6 M hexane solution, 38.9 mmol) was added dropwise to an anhydrous THF (50 mL) solution of Compound 13 (4.8 g, 24.4 mmol) at −78° C., and the temperature was then increased to 0° C. Then, the mixture was stirred for 1 hour. Thereafter, an anhydrous THF (50 mL) solution of Compound 12 (2.9 g, 11.8 mmol) (synthesized in accordance with Duthaler, O. D. Angew. Chem. 1991, 103, 729) and HMPA (6 mL) was added dropwise to the reaction solution at −78° C., and the obtained mixture was then stirred for 2 hours. Thereafter, a saturated ammonium chloride aqueous solution was added to the reaction solution to quench the reaction, and the resulting mixture was then extracted with ethyl acetate. The organic layer was washed with brine and was then dried, and the solvent was then distilled away under reduced pressure. The obtained crude product was purified by silica gel column chromatography (hexane-ethyl acetate), so as to obtain a crude product containing Compound 14.

(1R,7aR)-5,5-Dimethyl-1-(5-(4-methyl-2,6,7-trioxabicyclo[2.2.2]octan-1-yl)-1-pentyn-1-yl)dihydro-1H-thiazolo[3,4-c]oxazol-3(5H)-one (15)

[Formula 21]

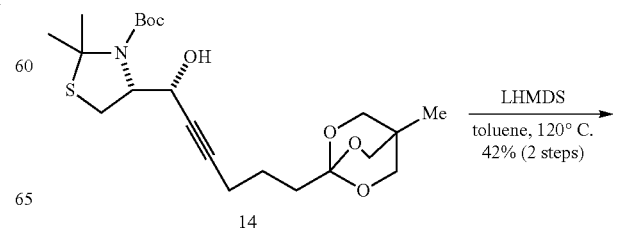

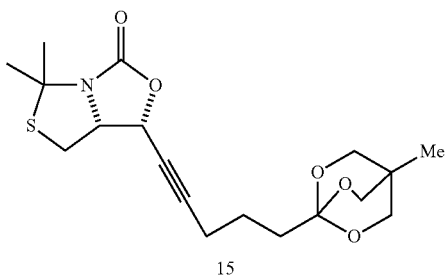

A hexamethyldisilazane lithium solution (1 M THF solution, 7.88 mmol) was added to an anhydrous toluene (40 mL) solution containing Compound 14, and the obtained mixture was then stirred at 120° C. for 12 hours. Thereafter, a saturated ammonium chloride aqueous solution was added to the reaction solution, and the obtained mixture was then extracted with ethyl acetate. The organic layer was washed with brine and was then dried, and the solvent was then distilled away under reduced pressure. The obtained crude product was purified by silica gel column chromatography (hexane-ethyl acetate), so as to obtain 1.82 g of the title compound (two-step yield: 42%, a light yellow oily substance).

$^1$H NMR (CDCl$_3$): δ=0.79 (s, 3H), 1.68 (s, 3H), 1.70-1.75 (m, 4H), 1.80 (s, 3H), 2.28 (td, J=7.5, 1.7 Hz, 2H), 2.39 (t, J=7.4 Hz, 1H), 2.96 (dd, J=14, 4.3 Hz, 1H), 3.87 (s, 6H), 4.57-4.62 (m, 1H), 5.16 (d, J 7.5 Hz, 1H)

(E)-3-Hydroxy-2-(hydroxymethyl)-2-methylpropyl5-((3aR,6aS)-2-oxotetrahydrothieno[3,4-d]oxazol-6(6aH)-ylidene)pentanoate (16)

Silver(I) nitrate (50 mg, 0.30 mmol) was added to a mixed solution of CH$_3$CN (2.7 mL) and H$_2$O (2.7 mL) containing Compound 15 (150 mg, 0.41 mmol). The obtained mixture was stirred for 9 hours. Thereafter, the reaction solution was filtrated through Celite, and was then extracted with ethyl acetate. The organic layer was washed with brine and was then dried, and the solvent was then distilled away under reduced pressure. The obtained crude product was purified by silica gel column chromatography (ethyl acetate), so as to obtain 44 mg of the title compound 16 (yield: 31%, a light yellow oily substance). Also, 35 mg of Compound 17 was obtained as a by-product (yield: 25%, a light yellow oily substance).

$^1$H NMR (CD$_3$OD): δ=0.93 (s, 3H), 1.79 (quin, J=7.5 Hz, 2H), 2.16-2.31 (m, 2H), 2.40 (t, J=7.5 Hz, 2H), 3.02 (d, J=12 Hz, 1H), 3.25 (dd, J=12, 5.2 Hz, 1H), 3.48 (dd, J=18, 11 Hz, 4H), 4.03 (s, 2H), 4.64 (t, J=5.2 Hz, 1H), 5.47 (d, J=10 Hz, 1H), 5.93 (t, J=7.5 Hz, 1H)

3-Hydroxy-2-(hydroxymethyl)-2-methylpropyl 5-((3aR,6S,6aS)-2-oxohexahydrothieno[3,4-d]oxazol-6-yl)pentanoate (18)

[Formula 22]

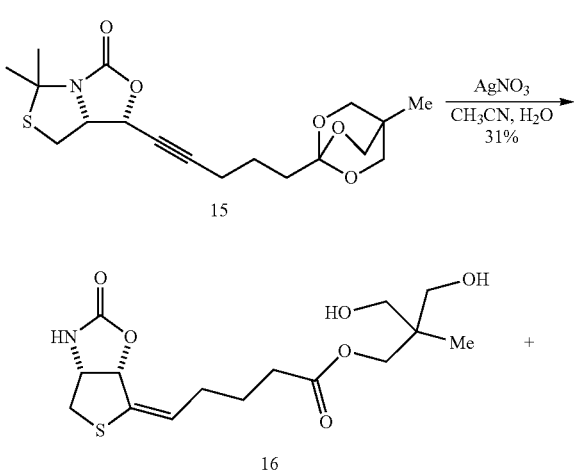

[Formula 23]

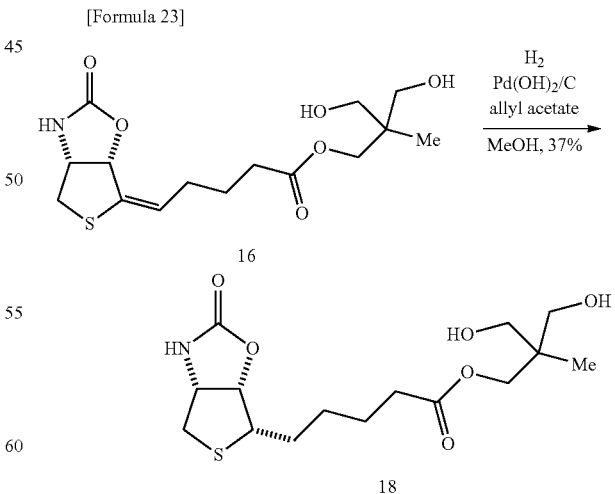

Palladium carbon hydroxide (10 w/w % Pd, 40 mol %, 0.013 mmol) was added to a MeOH (1 mL) solution of Compound 16 (11 mg, 0.032 mmol) and allyl acetate (344 μL, 3.2 mmol). The obtained mixture was stirred under hydrogen atmosphere (25 atm) at 50° C. for 4 hours. Thereafter, the reaction solution was cooled to room temperature and was then passed through a Celite short column (methanol). The solvent was distilled away under reduced pressure, and the obtained crude product was then purified by silica gel column chromatography (dichloromethane-methanol), so as to obtain 4.2 mg of the title compound (yield: 37%, a colorless oily substance).

$^1$H NMR (CD$_3$OD): δ=0.94 (s, 3H), 1.50-1.58 (m, 2H), 1.67-1.80 (m, 4H), 1.85-1.94 (m, 2H), 2.41 (t, J=7.2 Hz, 2H), 2.76 (d, J=13 Hz, 1H), 2.97 (dd, J=13, 4.5 Hz, 1H), 3.29-3.32 (m, 1H), 3.48 (dd, J=18, 11 Hz, 4H), 4.03 (s, 2H), 4.56 (dd, J=6.7, 4.5 Hz, 1H), 5.09 (dd, J=6.7, 4.0 Hz, 1H)

5-((3aR,6S,6aS)-2-Oxahexahydrothieno[3,4-d]oxazol-6-yl)pentanoic acid (19)

[Formula 24]

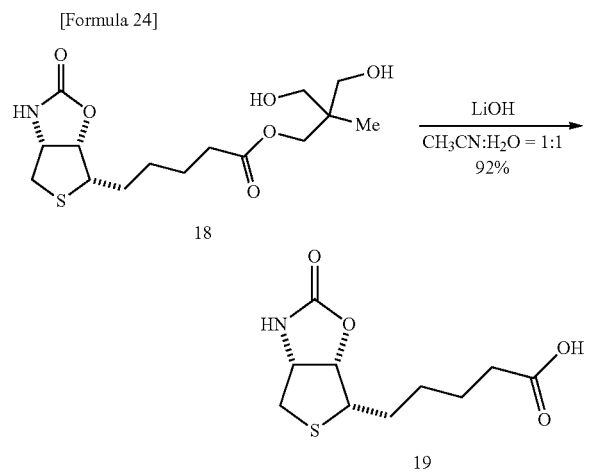

Lithium hydroxide (5 μmol) was added to a mixed solution of CH$_3$CN (500 μL) and H$_2$O (500 μL) containing Compound 18 (1.1 mg, 3.2 μmol). The obtained mixture was stirred for 12 hours, and the reaction was then terminated by addition of 1 M hydrochloric acid. The reaction solution was passed through a silica gel column chromatography (methanol). The solvent was distilled away under reduced pressure, and the obtained crude product was then purified by silica gel column chromatography (dichloromethane-methanol), so as to obtain 700 μg of the title compound (yield: 92%, a white solid).

$^1$H NMR (CD$_3$OD): δ=1.47-1.55 (m, 2H), 1.65-1.74 (m, 4H), 1.85-1.94 (m, 2H), 2.38 (t, J=7.5 Hz, 2H), 2.76 (d, J=13 Hz, 1H), 2.98 (dd, J=13, 4.6 Hz, 1H), 3.29-3.32 (m, 1H), 4.56 (dd, J=6.9, 4.6 Hz, 1H), 5.08 (dd, J=6.9, 4.0 Hz, 1H)

5-((3aS,4S,6aR)-5-Oxido-2-oxohexahydro-1H-thieno[3,4-d]imidazol-4-yl)pentanoic acid (21)

[Formula 25]

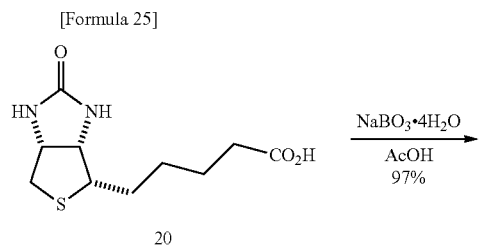

NaBO$_3$·4H$_2$O (94.6 mg, 0.62 mmol) was added to an acetic acid (1 ml) solution of the biotin (20) (50 mg, 0.21 mmol) at room temperature. The obtained mixture was stirred for 1 hour 20 minutes at room temperature. Thereafter, thiosodium sulfate (160 mg) was added to the reaction solution, and the solvent was then distilled away under reduced pressure. The obtained crude product was purified by silica gel column chromatography (dichloromethane-methanol-water), and was further purified by reverse-phase column chromatography (methanol), so as to obtain 51.6 mg of the title compound (yield: 97%, a light yellow oily substance).

$^1$H NMR (CD$_3$OD): δ=1.49-1.63 (m, 2H), 1.63-1.75 (m, 2H), 1.83-1.95 (m, 2H), 2.26 (m, 2H), 3.06 (dd, J=13, 2.1 Hz, 1H), 3.12-3.16 (m, 1H), 3.50 (dd, J=13, 2.1 Hz, 1H), 4.60 (dd, J=8.9, 5.2 Hz, 1H), 4.67 (dd, J=8.9, 2.1 Hz, 1H)

5-((3aS,4S,6aR)-2-Imino-5-oxidohexahydro-1H-thieno[3,4-d]imidazol-4-yl)pentanoic acid (23)

[Formula 26]

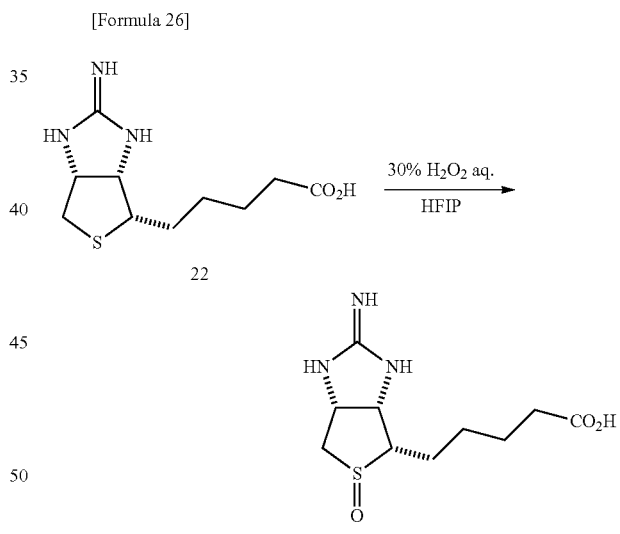

A 30% H$_2$O$_2$ aqueous solution (5 μL) was added to a 1,1,1,3,3,3-hexafluoroisopropanol (100 μL) solution of the iminobiotin (22) (5.0 mg, 0.021 mmol) at room temperature. The obtained mixture was stirred at room temperature for 20 minutes. Thereafter, the solvent was distilled away under reduced pressure, so as to obtain 5.2 mg of the title compound (yield: 98%, a diastereo mixture, dr=1:1.6, a white solid).

$^1$H NMR (CD$_3$OD): δ=1.55-1.82 (m, 10.4H), 1.84-1.93 (m, 3.2H), 2.00-2.11 (m, 2H), 2.19-2.31 (m, 5.2H), 2.96 (dd, J=14, 7.5 Hz, 1H), 3.01 (dd, J=16, 6.9 Hz, 1H), 3.15 (dd, J=13, 5.8 Hz, 1.6H), 3.23-3.28 (m, 1.6H), 3.48 (d, J=16 Hz, 1H), 3.60 (dd, J=14, 1.7 Hz, 1.6H), 4.86-4.91 (m, 2.6H), 4.95 (dd, J=8.6, 6.3 Hz, 1.6H), 5.08 (dd, J=8.6, 6.3 Hz, 1H)

5-((3aS,4S,6aR)-5-Oxido-2-oxotetrahydrothieno[3,4-d][1,3]dioxol-4-yl)pentanoic acid (24)

[Formula 27]

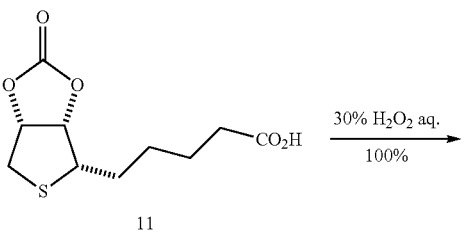

A 30% H₂O₂ aqueous solution (5 μl) was added to a 1,1,1,3,3,3-hexafluoroisopropanol (100 μL) solution of Compound 11 (0.6 mg, 0.002 mmol) at room temperature. The obtained mixture was stirred at room temperature for 10 minutes, and thereafter, the solvent was distilled away under reduced pressure, so as to obtain 0.6 mg of the title compound (yield: 100%, a diastereo mixture, dr=1:1.1, a white solid).

$^1$H NMR (CD$_3$OD): δ=1.60-1.80 (m, 8.4H), 1.90-2.18 (m, 4.2H), 2.33-2.39 (m, 4.2H), 3.03-3.10 (m, 2.1H), 3.20 (dd, J=14, 5.8 Hz, 1H), 3.30-3.40 (m, 1.1H), 3.69 (d, J=16 Hz, 1.1H), 3.96 (dd, J=14, 1.2 Hz, 1H), 5.47 (dd, J=7.4, 5.5 Hz, 1H), 5.53-5.58 (m, 2.1H), 5.73 (dd, 7.1, 5.5 Hz, 1.1H)

Methyl 5-((3aS,4S,6aR)-2-thioxohexahydro-1H-thieno[3,4-d]imidazol-4-yl)pentanoate (26)

[Formula 28]

A Lawesson's reagent (5.3 mg, 0.013 mmol) was added to a toluene (200 μL) solution of the biotin methyl ester (25) (5.0 mg, 0.019 mmol). The obtained mixture was stirred at 100° C. for 13 hours. Thereafter, the reaction solution was cooled to room temperature, and the solvent was then distilled away under reduced pressure. The obtained crude product was purified by silica gel column chromatography (dichloromethane-methanol), so that insoluble compounds were removed, thereby obtaining 3.8 mg of a crude product (a white solid).

5-((3aS,4S,6aR)-2-Thioxohexahydro-1H-thieno[3,4-d]imidazol-4-yl)pentanoic acid (27)

[Formula 29]

100 μL of a 20% sodium hydroxide aqueous solution was added to a THF (100 μL) solution of 2.4 mg of the crude product containing Compound 26 at room temperature. The obtained mixture was stirred at 60° C. for 1 hour. Thereafter, the reaction solution was cooled to room temperature, and 500 μL of 1 M hydrochloric acid was then added dropwise thereto. After that, the solvent was distilled away under reduced pressure. The obtained crude product was purified by silica gel column chromatography (dichloromethane-methanol), so as to obtain 0.7 mg of the title compound (a white solid).

$^1$H NMR (CD$_3$OD): δ=1.42-1.51 (m, 2H), 1.57-1.72 (m, 3H), 1.75-1.82 (m, 1H), 2.28-2.34 (m, 2H), 2.79 (d, J=13 Hz, 1H), 2.96 (dd, J=13, 4.6 Hz, 1H), 3.25-3.28 (m, 1H), 4.48 (dd, J=8.3, 4.6 Hz, 1H), 4.67 (dd, J=4.3, 8.3 Hz, 1H)

5-((3aR,6S,6aS)-2-Oxohexahydrothieno[3,4-d]oxazol-6-yl)pentanoic acid (29)

[Formula 30]

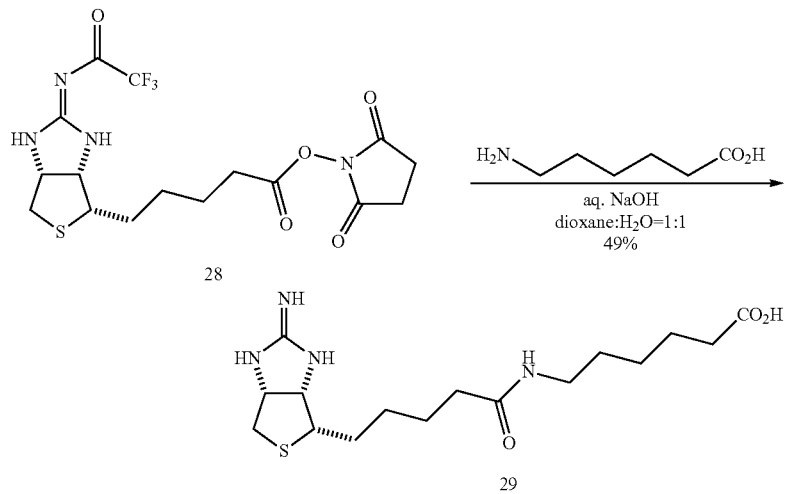

A sodium hydroxide aqueous solution was added to a mixed solution of dioxane (500 μL) and H₂O (500 μL) containing 6-aminohexanoic acid (3 mg, 0.023 mmol), so that the pH of the solution was then adjusted to approximately pH 9. Compound 28 (10 mg, 0.023 mmol) (a commercially available product) was added to the solution, and the obtained mixture was then stirred for 12 hours. Thereafter, ether was added to the reaction solution to remove the organic layer. The water layer was neutralized by hydrochloric acid and was then filtrated. The residue was washed with acetone, and the solvent was then distilled away under reduced pressure. The obtained solid was dissolved in dioxane (500 μL) and H₂O (500 μL), and 29% ammonia water was then added to the mixed solution. The thus obtained mixture was stirred for 3 hours. Thereafter, the solvent was distilled away under reduced pressure, and the obtained crystal was then washed with a mixed solvent of dichloromethane and methanol to obtain 4 mg of the title compound (yield: 49%, a white solid).
MS (ESI) m/z 357 (M+H)⁺

(S)-2-((tert-Butoxycarbonyl)amino)-6-(5-((3aS,4S,6aR,Z)-2-((2,2,2-trifluoroacetyl)imino)hexahydro-1H-thieno[3,4-d]imidazol-4-yl)pentanamido)hexanoic acid (30)

[Formula 31]

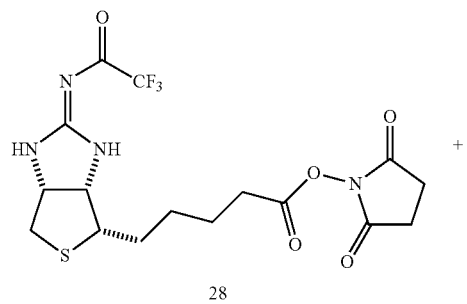

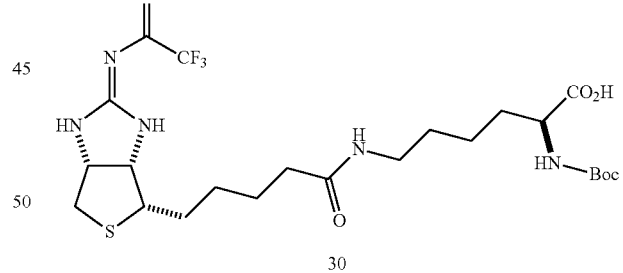

A mixed solvent of dioxane/water containing Compound 28 (10 mg, 0.023 mmol) and Nα-Boc-L-lysine (5 mg, 0.023 mmol) was stirred for 18 hours. Thereafter, ether was added to the reaction solution to remove the organic layer. The solvent was distilled away under reduced pressure, and the obtained crude product was used in the subsequent reaction without being subjected to a further purification operation.

(S)-2-Amino-6-(5-((3aS,4S,6aR)-2-iminohexahydro-1H-thieno[3,4-d]imidazol-4-yl)pentanamide)hexanoic acid (31)

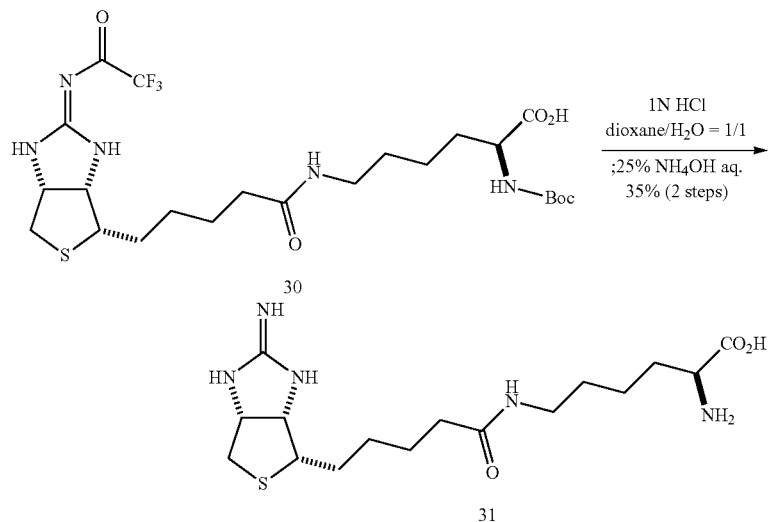

Hydrochloric acid was added to a mixed solution of dioxane (500 μL) and H₂O (500 μL) containing the crude product containing Compound 30, so that the pH of the solution was adjusted to approximately pH 3. The obtained mixture was stirred for 5 hours, and the solvent was then distilled away under reduced pressure. The obtained solid was dissolved in dioxane (500 μL) and H₂O (500 μL), and 25% ammonia water was then added to the solution. The obtained mixture was stirred for 3 hours. Thereafter, the solvent was distilled away under reduced pressure, and the obtained crystal was then washed with a mixed solvent of dichloromethane and methanol, so as to obtain 3.1 mg of the title compound (two-step yield: 35%, a white solid).
MS: 371.80

(E)-Benzyl 5-((3aS,4S,6aR)-2,2-Dimethyltetrahydrothieno[3,4-d][1,3]dioxol-4-yl)-2-pentenoate (33)

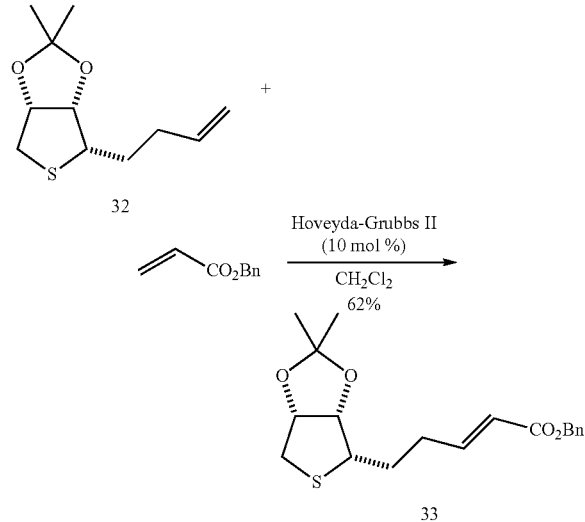

Benzyl acrylate (70 μL, 0.47 mmol) and a second generation Hoveyda-Grubbs catalyst (3 mg, 4.7 mmol) were added to a CH₂Cl₂ (500 μL) solution of Compound 32 (10 mg, 0.047 mmol), and the obtained mixture was then stirred for 12 hours. Thereafter, the solvent was distilled away under reduced pressure, and the obtained crude product was then purified by silica gel column chromatography (hexane-ethyl acetate), so as to obtain 10 mg of the title compound (62%, a yellow oily substance).

¹H NMR (CDCl₃): δ=1.31 (s, 3H), 1.49 (s, 3H), 1.83-1.92, (m, 1H), 1.96-2.03 (m, 1H), 2.32-2.38 (m, 2H), 2.83 (dd, J=13, 4.3 Hz, 1H), 2.87 (d, J=13 Hz, 1H), 3.06-3.11 (m, 1H), 4.59 (t, J=5.5 Hz, 1H), 4.84 (t, J=4.6 Hz, 1H), 5.18 (s, 2H), 5.93 (d, J=16 Hz, 1H), 7.01 (dt, J=16, 7 Hz, 1H), 7.32-7.36 (m, 2H), 7.37 (d, J=4.6 Hz, 3H)

Benzyl 5-((3aS,4S,6aR)-2,2-dimethyltetrahydrothieno[3,4-d][1,3]dioxol-4-yl)pentanoate (34)

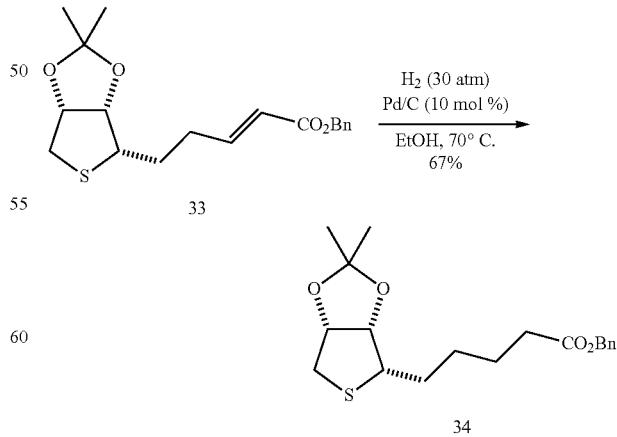

Palladium carbon (10 w/w % Pd, 10 mol %, 5.0 mg) was added to an EtOH (1 mL) solution of Compound 33 (10 mg, 0.028 mmol). The obtained mixture was stirred in the presence of hydrogen gas (30 atm) at 70° C. for 2 hours. The reaction solution was cooled to room temperature, and it was passed through a Celite short column (ethanol). The solvent was distilled away under reduced pressure. The obtained crude product was purified by silica gel column chromatography (hexane-ethyl acetate), so as to obtain 6.5 mg of the title compound (67%, a light yellow oily substance).

$^1$H NMR (CDCl$_3$): δ=1.31 (s, 3H), 1.49 (s, 3H), 1.47-1.50 (m, 2H), 1.65-1.75 (m, 3H), 1.80-1.86 (m, 1H), 2.37 (t, J=7.0 Hz, 2H), 2.80 (dd, J=13, 3.5 Hz, 1H), 2.85 (d, J=13 Hz, 1H), 3.06-3.10 (m, 1H), 4.58 (t, J=4.3 Hz, 1H), 4.88 (t, J=4.3 Hz, 1H), 5.11 (s, 2H), 7.32-7.37 (m, 5H)

5-((2S,3S,4R)-3,4-Dihydroxytetrahydrothiophen-2-yl)pentanoic acid (35)

[Formula 35]

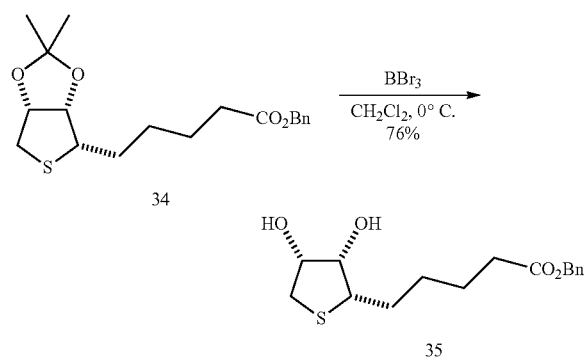

1 M Boron tribromide (36 μL, 0.050 mmol) was added to a CH$_2$Cl$_2$ (600 μL) solution of Compound 34 (2.5 mg, 7.1 μmol) at −78° C. The obtained mixture was stirred at 0° C. for 3 hours. Thereafter, a saturated ammonium chloride aqueous solution was added to the reaction solution, and the obtained mixture was then extracted with ethyl acetate. The organic layer was washed with brine and was then dried, and the solvent was then distilled away under reduced pressure. The obtained crude product was purified by silica gel column chromatography (dichloromethane-methanol), so as to obtain 1.2 mg of the title compound (yield: 76%, a colorless oily substance).

$^1$H NMR (CDCl$_3$): δ=1.43-1.50 (m, 2H), 1.65-1.75 (m, 3H), 1.80-1.88 (m, 1H), 2.38 (t, J=7.3 Hz, 2H), 2.81 (t, J=11 Hz, 1H), 3.03 (dd, J=11, 7.0 Hz, 1H), 3.38-3.43 (m, 1H), 4.11 (t, J=3.3 Hz, 1H), 4.31 (td, J=9.1, 3.3 Hz, 1H)

5-((3aS,4S,6aR)-2-Oxidotetrahydrothieno[3,4-d][1,3,2]dioxathiol-4-yl)pentanoic acid (36)

[Formula 36]

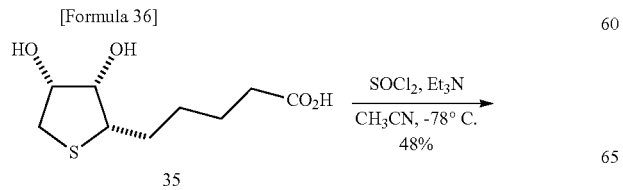

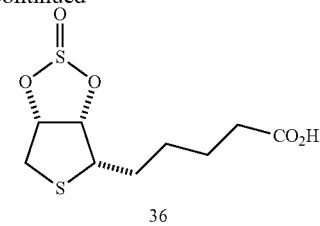

Thionyl chloride (0.5 μL, 7.2 μmol) was added to a CH$_3$CN (400 μL) solution of Compound 35 (1.2 mg, 5.4 μmol) at −78° C. The obtained mixture was stirred at 0° C. for 3 hours. Thereafter, brine was added to the reaction solution, and the obtained mixture was then extracted with CH$_2$Cl$_2$. The organic layer was washed with brine and was then dried, and the solvent was then distilled away under reduced pressure. The obtained crude product was purified by silica gel column chromatography (dichloromethane-methanol), so as to obtain 700 μg of the title compound (yield: 48%, a diastereo mixture, dr=2:1, a white solid).

$^1$H NMR (CDCl$_3$): δ=1.50-1.74 (m, 12H), 1.85-1.95 (m, 6H), 2.39 (t, J=7.4 Hz, 6H), 3.08 (dd, J=14, 5.8 Hz, 1H), 3.14 (dd, J=14, 2.1 Hz, 1H), 3.31-3.37 (m, 4H), 3.64 (br, 1H), 4.27-4.31 (m, 1H), 5.19 (dd, J=5.5, 4.3 Hz, 1H), 5.33-5.36 (m, 1H), 5.36 (dd, 5.5, 4.3 Hz, 2H), 5.54-5.57 (m, 2H)

4-((3aR,6S,7aR)-2-Oxohexahydro-2H-thiopyrano[3,4-d]oxazol-6-yl)butanoic acid (37)

[Formula 37]

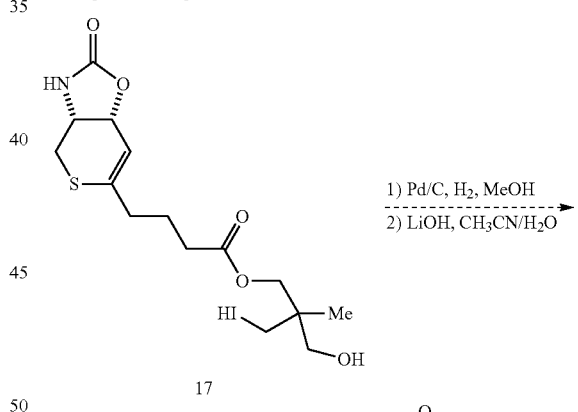

Compound 17 was dissolved in MeOH, and the obtained solution was then stirred using a catalytic amount of Pd/C in a hydrogen atmosphere, so as to reduce a double bond.

Subsequently, the ester portion of the obtained compound was hydrolyzed using LiOH in a mixed solvent of CH₃CN and H₂O, so as to obtain Compound 37.

Additional Example 1: Synthesis of Modified Biotin (Addition)

General Method

The nuclear magnetic resonance (NMR) spectrum was recorded using a JEOL ECX500 (¹H NMR: 500 MHz) or JEOL ECS400 (¹H NMR: 400 MHz) spectrometer. The chemical shift was described as a value relative to the remaining solvent peak in a heavy solvent used as an internal reference, at a unit of ppm (CDCl₃: δ=7.26 ppm, CD₃OD: δ=3.31 ppm, D₂O: δ=4.79 ppm). The low-resolution mass spectrum (LHMS) was measured by ESI-MS using Waters-ZQ4000 spectrometer. Column chromatography was carried out using silica gel Merk 60 (230-400 mesh ASTM). The reaction was traced by thin-layer chromatography (TLC) or low-resolution mass spectrometry (LRMS).

Reverse-phase high performance liquid chromatography (HPLC) was carried out using JASCO-HPLC System. Detection was carried out using ultraviolet light at 210 nm or 254 nm. As a mobile phase, a gradient solvent system (acetonitrile/0.1% trifluoroacetic acid MQ solution) was used. For analysis, a YMC-Pack ODS-AM column (150×4 6 mL) was used, and the flow rate was set at 1 mL/min. For separation, a YMC-Pack ODS-AM column (250×20 mL) was used, and the flow rate was set at 8 to 10 mL/min.

Reagents were purchased from Aldrich, Tokyo Chemical Industry Co., Ltd. (TCI), Kanto Kagaku K. K. (Kanto), Wako Pure Chemical Industries, Ltd., and Watanabe Chemical Industries, Ltd. Commercially available products were directly used as reagents and solvents that were all used in the present method, unless otherwise specified.

3-Hydroxy-2-(hydroxymethyl)-2-methylpropyl(E)-(3S,4R)-5-[4-(tert-butoxycarbonylamino)-3-hydroxydihydrothiophen-2(3H)-ylidene)]pentanoate (38)

[Formula 38]

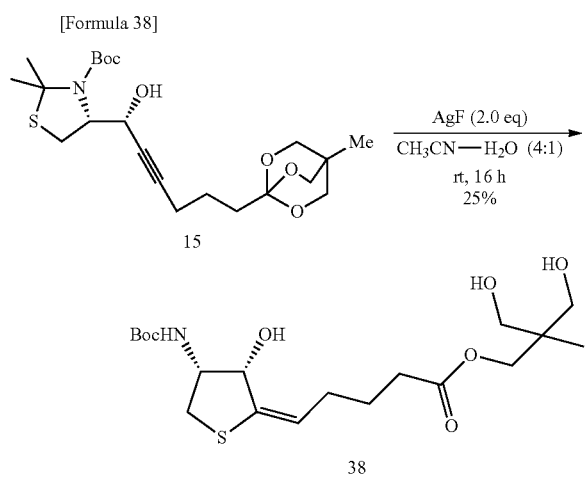

Silver fluoride (1.15 g, 9.06 mmol) was added to a mixed solution of acetonitrile (38 mL) and water (7 mL) containing Compound 15 (2.0 g, 4.53 mmol), and the obtained mixture was then stirred at room temperature for 16 hours. Thereafter, the obtained mixture was passed through a silica gel short column (ethyl acetate). The solvent was distilled away under reduced pressure, and the obtained crude product was then purified by silica gel column chromatography (hexane/ethyl acetate=1:1→1:2), so as to obtain the title compound 38 (0.475 g, yield: 25%, a yellow highly viscous oily substance).

¹H NMR (500 MHz, CD₃OD) δ: 0.91 (s, 3H), 1.45 (s, 9H), 1.75 (quint., 2H, J=7.4 Hz), 2.05 (q, 2H, J=7.4 Hz), 2.38, (t, 2H, J=7.5 Hz), 3.02 (dd, 1H, J=9.2, 10.3 Hz), 3.08 (1H, dd, J=6.3, 10.3 Hz), 3.45 (dd, 4H, J=14.9, 11.5 Hz), 3.98-4.01 (m, 1H), 4.00 (2H, s), 4.39 (d, 1H, J=4.0 Hz), 5.66 (t, 1H, J=6.9 Hz); LRMS (ESI): m/z 442 [M+Na]⁺.

tert-Butyl (E)-(3aR,6aS)-2,2-dimethyl-6-{5-oxo-5-[(2,2,5-trimethyl-1,3-dioxane-5-yl)methoxy]pentylidene}tetrahydrothieno[3,4-d]oxazole-3(2H)-carboxylate (39)

[Formula 39]

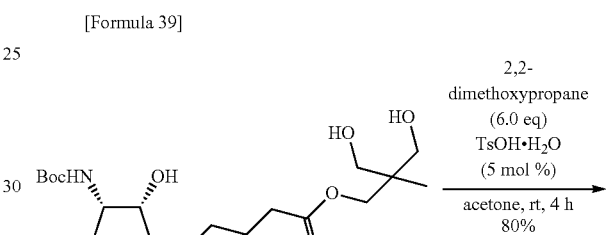

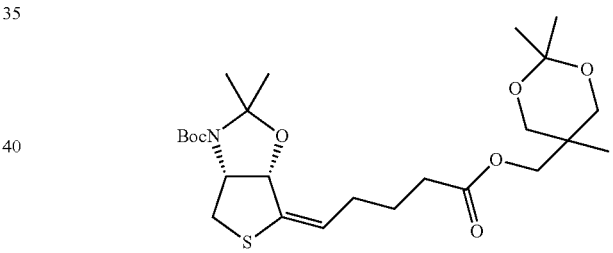

p-Toluenesulfonic acid monohydrate (12 mg, 0.063 mmol) was added to an anhydrous acetone (13 mL) solution of the triol form 38 (0.529 g, 1.26 mmol) and 2,2-dimethoxypropane (0.93 mL, 7.56 mmol), and the obtained mixture was then stirred at room temperature for 4 hours. Thereafter, triethylamine (53 μL, 0.378 mmol) was added to the reaction solution, and the solvent was then distilled away under reduced pressure. The obtained crude product was purified by silica gel column chromatography (hexane/ethyl acetate=4:1), so as to obtain the title compound 39 (0.526 g, yield: 80%, a colorless oily substance).

¹H NMR (500 MHz, CD₃OD) δ: 0.86 (s, 3H), 1.35 (s, 3H), 1.43 (s, 3H), 1.48 (s, 5H), 1.47-1.53 (m, 12H), 1.62 (s, 3H), 1.76 (quint., 2H, J=7.5 Hz), 2.11 (q, 2H, J=7.5 Hz), 2.39 (t, 2H, J=7.5 Hz), 3.01 (td, 1H, J=11.5, 7.4 Hz), 3.37 (m, 1H), 3.65 (s, 4H), 4.14 (dd, 2H, J=13.8, 10.9 Hz), 4.50 (sext., 1H, J=5.7 Hz), 4.96 (dd, 1H, J=8.0, 5.7 Hz), 5.75 (t, 1H, J=7.5 Hz); LRMS (ESI): m/z 522 [M+Na]⁺.

5-[(3aR,6S,6aS)-3-(tert-Butoxycarbonyl)-2,2-dimethylhexahydrothieno[3,4-d]oxazol-6-yl]pentanoic acid (42)

[Formula 40]

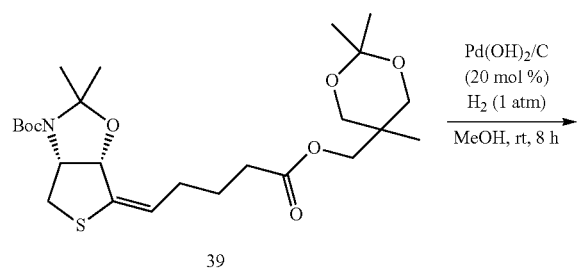

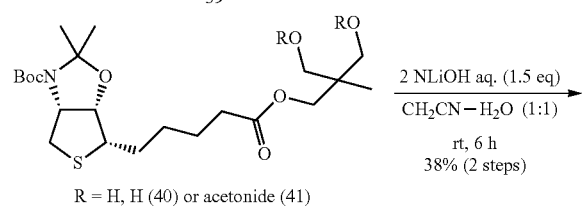

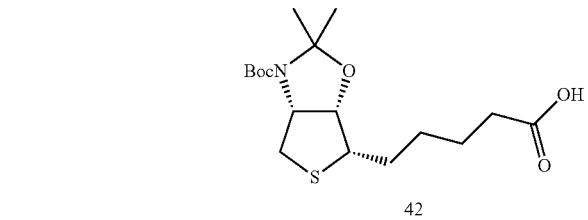

A Pearlman catalyst (10% palladium, 174 mg, 0.124 mmol) was added to a methanol (12 mL) solution of the diacetonide form 39 (0.310 g, 0.620 mmol). Argon gas was added to the mixed solution, and was then substituted with hydrogen gas (1 atmosphere, balloon). The resultant was stirred at room temperature for 8 hours. The mixture was passed through Celite, and was then eluted with methanol to remove the Pearlman catalyst. Then, the solvent was then distilled away under reduced pressure. The obtained crude product was passed through a silica gel short column, and was then eluted with hexane/ethyl acetate=4:1 to obtain a mixture of Compounds 40 and 41, in which a double bond was reduced. This crude product was dissolved in a mixed solvent of acetonitrile (6.2 mL) and water (6.2 mL), and a 2 N lithium hydroxide aqueous solution (0.47 mL, 0.93 mmol) was then added to the solution. The obtained mixture was stirred at room temperature for 6 hours. Thereafter, the water layer was washed with diethyl ether, and 2 N hydrochloric acid was then added to the solution to convert it to an acetic solution (pH<5). The solution was extracted with ethyl acetate, and the organic layer was then washed with brine. It was dried over sodium sulfate, and the solvent was then distilled away under reduced pressure. The obtained crude product was purified by silica gel column chromatography (hexane/ethyl acetate=2:1), so as to obtain the title compound 42 (85 mg, 2-step yield: 38%, a white solid).

40: $^1$H NMR (500 MHz, CD$_3$OD) δ: 0.86 (s, 3H), 1.35 (s, 3H), 1.43 (s, 3H), 1.44-1.50 (m, 14H), 1.60 (s, 3H), 1.64-1.72 (m, 3H), 1.84 (sext., 1H, J=6.9 Hz), 2.38 (t, 2H, J=7.5 Hz), 2.81 (t, 1H, J=10.9 Hz), 3.02 (tt, 1H, J=12.6, 6.3 Hz), 3.22-3.29 (m, 1H), 3.66 (s, 4H), 4.14 (s, 2H), 4.48 (ddd, 1H, J=18.9, 12.6, 6.3 Hz), 4.59-4.64 (m, 1H); LRMS (ESI): m/z 524 [M+Na]$^+$.

41: $^1$H NMR (500 MHz, CD$_3$OD) δ: 0.91 (s, 3H), 1.44-1.50 (m, 14H), 1.60 (s, 3H), 1.63-1.72 (m, 3H), 1.84 (sext., 1H, J=6.9 Hz), 2.37 (t, 2H, J=7.5 Hz), 2.81 (t, 1H, J=10.9 Hz), 3.02 (tt, 1H, J=12.6, 6.3 Hz), 3.23-3.29 (m, 1H), 3.45 (dd, 4H, J=14.9, 10.9 Hz), 4.00 (s, 2H), (ddd, 1H, J=18.9, 12.6, 6.3 Hz), 4.59-4.64 (m, 1H); LRMS (ESI): m/z 484 [M+Na]$^+$.

42: $^1$H NMR (500 MHz, CD$_3$OD) δ: 1.43-1.51 (m, 14H), 1.60 (s, 3H), 1.61-1.72 (m, 3H), 1.84 (sext., 1H, J=6.9 Hz), 2.30 (t, 2H, J=7.5 Hz), 2.81 (t, 2H, J=10.9 Hz), 3.03 (tt, 1H, J=12.6, 6.3 Hz), 3.22-3.29 (m, 1H), (ddd, 1H, J=18.9, 12.6, 6.3 Hz), 4.59-4.64 (m, 1H); LRMS (ESI): m/z 382 [M+Na]$^+$.

6-{[(3aR,6S,6aS)-3-(tert-Butoxycarbonyl)-2,2-dimethylhexahydrothieno[3,4-d]oxazol-6-yl]pentanamide}hexanoic acid (44)

[Formula 41]

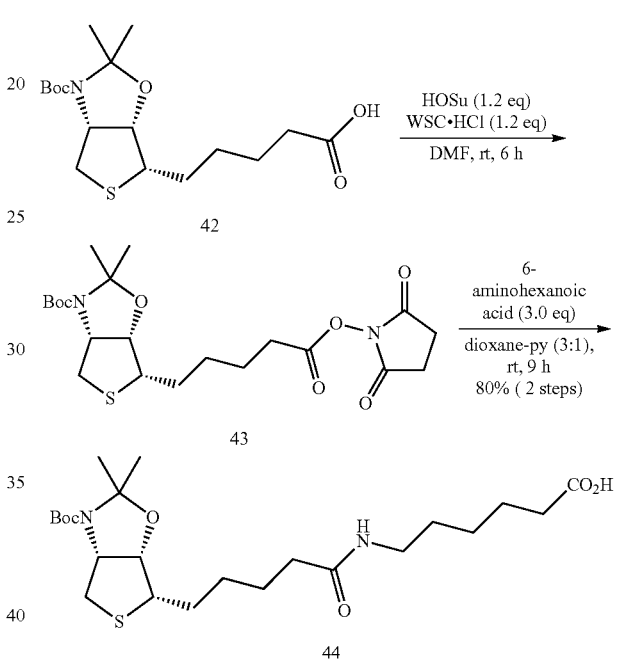

1-Ethyl-3-(3-dimethylaminopropyl)carbodiimide hydrochloride (WSC.HCl, 31.1 mg, 0.162 mmol) was added to an N,N-dimethylformamide (1.4 mL) solution of the carboxylic acid 42 (48.5 mg, 0.135 mmol) and N-hydroxysuccinimide (18.6 mg, 0.162 mmol), and the obtained mixture was then stirred at room temperature for 6 hours. Thereafter, the solvent was distilled away under reduced pressure, and the residue was then dissolved in ethyl acetate. The resulting solution was washed with a small amount of 0.5 N hydrochloric acid three times, and was then washed with brine. The resultant was dried over sodium sulfate, and the solvent was then distilled away under reduced pressure to obtain the active ester form 43. The obtained Compound 43 was dissolved in a mixed solvent of dioxane (1.6 mL) and water (0.5 mL), and 6-aminohexanoic acid (42.1 mg, 0.321 mmol) was then added thereto. The obtained mixture was stirred at room temperature for 9 hours. Thereafter, the solvent was distilled away under reduced pressure, a 1 N sodium hydroxide aqueous solution was then added to the residue, and the water layer was then washed with diethyl ether twice. 1 N Hydrochloric acid was added to the water layer to convert it to an acidic layer (pH<5), the mixture was then extracted with ethyl acetate, and the organic layer was then washed with a saturated saline. It was dried over sodium sulfate, and the solvent was then distilled away under reduced pressure. The obtained crude product was purified by silica gel column chromatography (dichloromethane/methanol=10:1), so as to obtain the title compound 44 (40 mg, 2-step yield: 80%, a colorless highly viscous oily substance).

$^1$H NMR (500 MHz, CD$_3$OD) δ: 1.35-1.40 (m, 3H), 1.42-1.54 (m, 16H), 1.60 (s, 3H), 1.61-1.72 (m, 4H), 1.84 (sext., 1H, J=6.9 Hz), 2.19 (t, 2H, J=7.5 Hz), 2.30 (t, 2H, J=7.5 Hz), 2.80 (t, 2H, J=10.9), 3.02 (tt, 1H, 1H, J=12.6, 6.3 Hz), 3.17 (t, 2H, J=6.9 Hz), 3.22-3.29 (m, 1H), (ddd, 1H, J=18.9, 12.6, 6.3 Hz), 4.58-4.64 (m, 1H); LRMS (ESI): m/z 495 [M+Na]$^+$.

(3R,4S,5S)-5-[5-(5-Carboxylpentylamino)-5-oxy-pentyl]-4-hydroxytetrahydrothiophene-3-ammonium chloride (45)

[Formula 42]

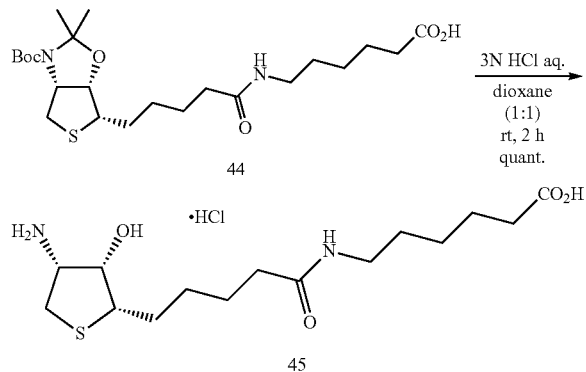

3 N Hydrochloric acid (5 mL) was added to a dioxane (5 mL) solution of the carboxylic acid 44 (76.9 mg, 0.163 mmol), and the obtained mixture was then stirred at room temperature for 2 hours. Thereafter, the solvent was distilled away under reduced pressure, and the residue was then washed with diethyl ether. The obtained solid was dried under reduced pressure to quantitatively obtain the title compound 45. If further purification were necessary, the obtained compound would be purified by silica gel column chromatography (dichloromethane/methanol=1:1) to obtain a white solid.

$^1$H NMR (500 MHz, D$_2$O) δ: 1.27-1.37 (m, 4H), 1.51 (quint., 2H, J=7.5 Hz), 1.55-1.64 (m, 5H), 1.76-1.82 (m, 1H), 2.23 (t, 2H, J=7.5 Hz), 2.38 (t, 2H, J=7.5 Hz), 2.93 (t, 1H, J=10.9 Hz), 3.14-3.18 (m, 3H), 3.58 (ddd, 1H, J=9.2, 6.3, 2.9 Hz), 3.85 (ddd, 1H, J=10.9, 7.5, 3.5 Hz), 4.39 (t, 1H, J=2.9 Hz); LRMS (ESI): m/z 334 [M+H]$^+$.

6-{5-[(3aR,6S,6aS)-2-Oxohexahydrothieno[3,4-d]oxazol-6-yl]pentanamide}hexanoic acid (46)

[Formula 43]

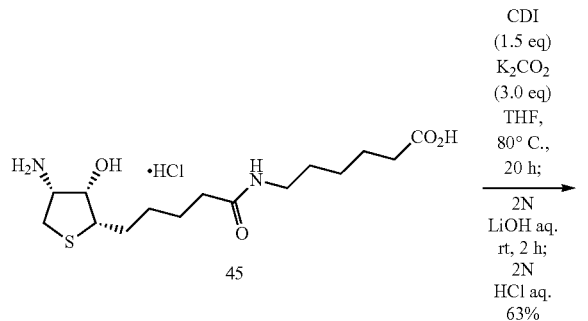

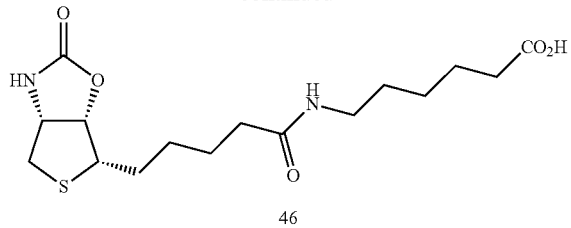

Potassium carbonate (16.9 mg, 0.122 mmol) and carbonyldiimidazole (CDI, 9.9 mg, 0.0611 mmol) were added to a tetrahydrofuran (4 mL) solution of the ammonium salt 45 (15.0 mg, 0.0407 mmol), and the obtained mixture was then stirred at 80° C. for 20 hours. Thereafter, the reaction solution was cooled to room temperature, and a 2 N sodium hydroxide aqueous solution (30 μL) was then added thereto. The obtained mixture was stirred at room temperature for 2 hours. Thereafter, water (0.5 mL) was added to the reaction solution, and the water layer was then washed with diethyl ether twice, and then with ethyl acetate twice. After that, 2 N hydrochloric acid was added thereto to convert it to an acidic layer (pH 3). The solvent was distilled away under reduced pressure, and a mixed solution of dichloromethane/methanol (1:1) was added to the residue. The solid was separated by filtration and was then removed. Thereafter, the solvent was distilled away under reduced pressure, and the obtained crude product was then purified by reverse-phase HPLC (YMC-Pack ODS-AM, gradient: 0-10-11-41-42-55 min; 0-0-21-51-100-100% CH$_3$CN in 0.1% TFA MQ, ramp time 30 min (21-51%), t$_R$=30.2 min), so as to obtain the title compound 46 (9.2 mg, 2-step yield: 63%, a white solid).

$^1$H NMR (400 MHz, CD$_3$OD) δ: 1.35-1.40 (m, 2H), 1.41-1.55 (m, 4H), 1.58-1.77 (m, 5H), 1.86 (next., 1H, J=6.3 Hz), 2.20 (t, 2H, J=7.2 Hz), 2.30 (t, 2H, J=7.2 Hz), 2.73 (d, 1H, J=13 Hz), 2.95 (dd, 1H, J=13.0, 4.5 Hz), 3.17 (t, 2H, J=7.2 Hz), 3.28 (dd, 1H, J=6.7, 3.6 Hz), 4.53 (dd, 1H, J=6.7, 4.5 Hz), 5.05 (dd, 1H, J=6.7, 3.6 Hz); LRMS (ESI): m/z 381 [M+Na]$^+$.

(3aR,6S,6aS)-6-[5-(5-Carboxylpentylamino)-5-oxopentyl]tetrahydrothieno[3,4-d]oxazol-2(3H)-iminium 2,2,2-trifluoroacetate (47)

[Formula 44]

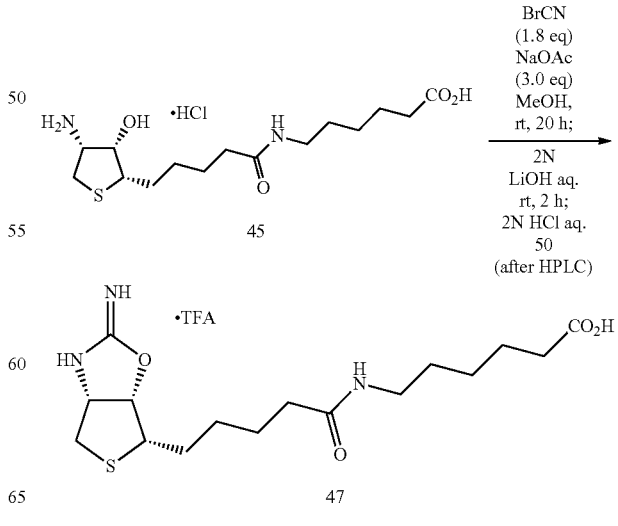

Sodium acetate (9.7 mg, 0.118 mmol) and cyanogen bromide (7.5 mg, 0.0707 mmol) were added to a methanol (2 mL) solution of the ammonium salt 45 (14.5 mg, 0.0393 mmol), and the obtained mixture was then stirred at room temperature for 20 hours. Thereafter, a 2 N sodium hydroxide aqueous solution (30 μL) was added to the reaction solution, and the obtained mixture was then stirred at room temperature for 2 hours. Thereafter, water (0.5 mL) was added to the reaction solution, and the water layer was washed with diethyl ether twice, and was then converted to an acidic layer by addition of 2 N hydrochloric acid (pH 3). The solvent was distilled away under reduced pressure, a mixed solution of dichloromethane/methanol (1:1) was then added to the residue, and a solid was removed by filtration. The solvent was distilled away under reduced pressure, and the obtained crude product was then purified by reverse-phase HPLC (YMC-Pack ODS-AM, gradient: 0-10-11-41-42-55 min; 0-0-18-48-100-100% $CH_3CN$ in 0.1% TFA MQ, ramp time 30 min (18-48%), $t_R$=26.5 min), so as to obtain the title compound 47 (9.2 mg, 2-step yield: 50%, a white solid).

$^1$H NMR (500 MHz, $D_2O$) δ: 1.31-1.38 (m, 2H), 1.41-1.49 (m, 2H), 1.53 (quint., 2H, J=7.5 Hz), 1.58-1.68 (m, 4H), 1.69-1.76 (m, 2H), 2.26 (t, 2H, J=7.5 Hz), 2.39 (t, 2H, J=7.5 Hz), 3.19 (q, 2H, J=6.9 Hz), 3.49 (ddd, 1H, J=9.2, 6.3, 2. Hz), 4.94 (dd, 1H, J=6.9, 5.2), 5.55 (dd, 1H, J=7.0, 4.0 Hz); LRMS (ESI): m/z 358 [M+H]$^+$.

3-Hydroxy-2-(hydroxymethyl)-2-methylpropyl 5-((3aR,6aS)-2-oxotetrahydrothieno[3,4-d]oxazol-6(6aH)-ylidene)pentanoate (16)

[Formula 45]

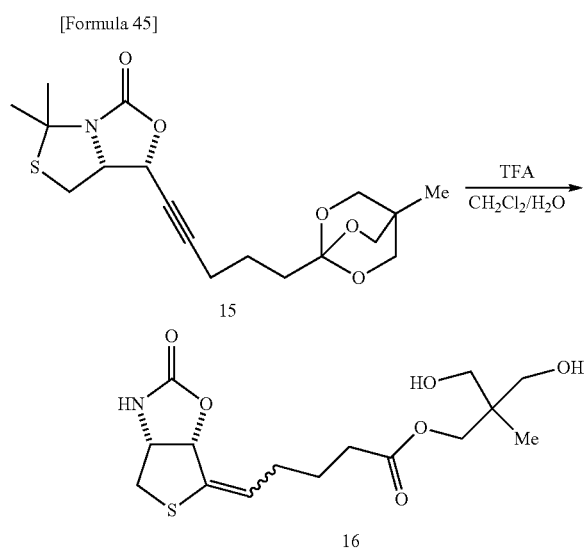

Trifluoroacetic acid (2 ml) was slowly added dropwise to a mixed solution of $CH_2Cl_2$ (2 mL) and $H_2O$ (50 μL) containing the Compound 15 (78 mg, 0.21 mmol). The obtained mixture was stirred for 24 hours. Thereafter, a saturated sodium bicarbonate aqueous solution was added to the reaction solution, and the obtained mixture was then extracted with ethyl acetate. The organic layer was washed with brine and was then dried, and the solvent was then distilled away under reduced pressure. The obtained crude product was used in the subsequent operation without being subjected to a further purification operation.

(2,2,5-Trimethyl-1,3-dioxane-5-yl)methyl 5-((3aR, 6aS)-2-oxotetrahydrothieno[3,4-d]oxazol-6(6aH)-ylidene)pentanoate (48)

[Formula 46]

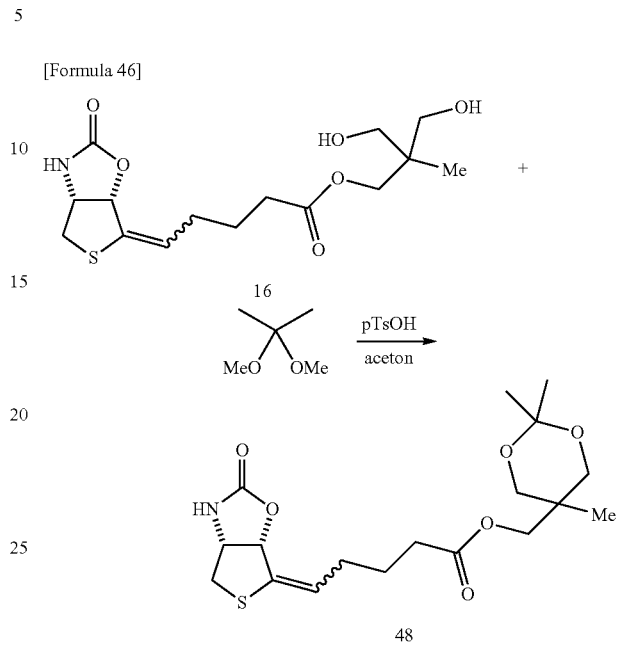

p-Toluenesulfonic acid (3.2 mg, 0.02 mmol) was added to an acetone (1 mL) solution of a crude product containing Compound 16 and 2,2-dimethoxypropane (77 μL, 0.63 mmol). The obtained mixture was stirred at 50° C. for 10 hours, and thereafter, 90 μL of triethylamine was added to the reaction solution. The mixed solution was passed through a short silica column, and was eluted with a mixed solvent of ethyl acetate and triethylamine. The solvent was distilled away under reduced pressure, and the obtained crude product was then purified by gel permeation chromatography to obtain the title compound 48 (40 mg, two-step yield: 53%, a colorless oily substance).

$^1$H NMR ($CD_3OD$): δ=0.89 (s, 3H), 1.37 (s, 3H), 1.45 (s, 3H), 1.76-1.83 (m, 2H), 1.85-1.94 (m, 2H), 2.41 (t, J=7.2 Hz, 2H), 3.02 (d, J=12 Hz, 1H), 3.24 (dd, J=12, 5.5 Hz, 1H), 3.68 (s, 4H), 4.17 (s, 2H), 4.64 (m, 1H), 5.47 (d, J=6.9 Hz, 1H), 5.92 (t, 7.3 Hz, 1H)

(2,2,5-Trimethyl-1,3-dioxane-5-yl)methyl 5-((3aR, 6S,6aS)-2-oxotetrahydrothieno[3,4-d]oxazol-6-yl)pentanoate (50)

[Formula 47]

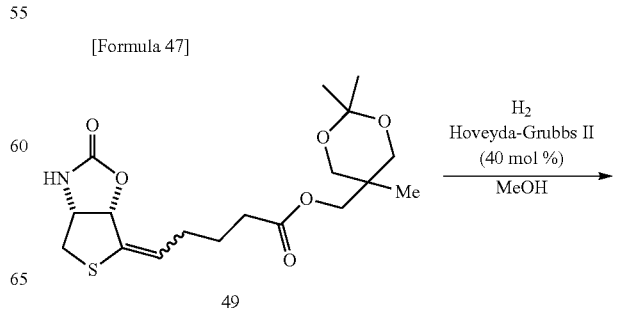

-continued

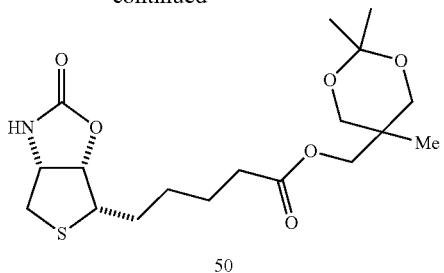

50

A second generation Hoveyda-Grubbs catalyst (0.8 mg, 1.6 μmol) was added to a MeOH (500 μL) solution of Compound 49 (1.5 mg, 3.9 μmol). The obtained mixture was stirred in the presence of hydrogen gas (30 atm) for 18 hours. Thereafter, the reaction solution was cooled to room temperature, and was then passed through a Celite short column (methanol). The solvent was distilled away under reduced pressure to obtain a crude product.

5-((3aR,6S,6aS)-2-Oxohexahydrothieno[3,4-d]oxazol-6-yl)pentanoic acid (51)

[Formula 48]

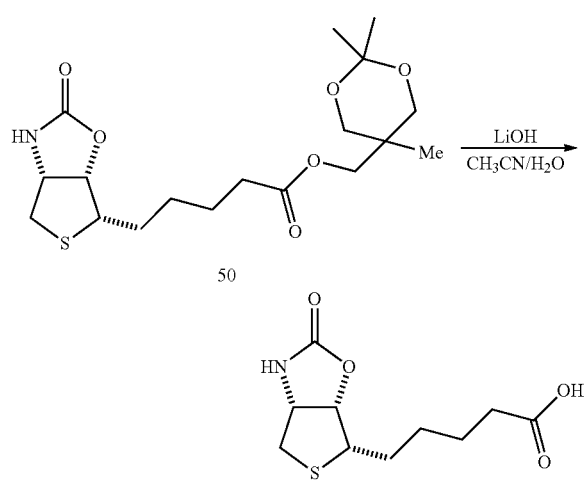

Lithium hydroxide (10 μmol) was added to a mixed solution of CH₃CN (500 μL) and H₂O (500 μL) of a crude product containing Compound 50, and the obtained mixture was then stirred for 12 hours. Thereafter, 1 M hydrochloric acid was added to the reaction solution to quench the reaction, and the resulting solution was passed through a silica gel column chromatography (methanol). The solvent was distilled away under reduced pressure, and the obtained crude product was then purified by silica gel column chromatography (dichloromethane-methanol), so as to obtain the title compound 51 (700 rig, two-step yield: 73%, a white solid)

¹H NMR (CD₃OD): δ=1.47-1.55 (m, 2H), 1.65-1.74 (m, 2H), 1.85-1.94 (m, 2H), 2.38 (t, J=7.5 Hz, 2H), 2.76 (d, J=13 Hz, 1H), 2.98 (dd, J=13, 4.6 Hz, 1H), 3.29-3.32 (m, 1H), 4.56 (dd, J=6.9, 4.6 Hz, 1H), 5.08 (dd, J=6.9, 4.0 Hz, 1H)

3-Hydroxy-2-(hydroxymethyl)-2-methylpropyl 4-((3aR,7aR)-2-oxo-3,3a,4,7a-tetrahydro-2H-thiopyrano[3,4-d]oxazol-6-yl)butanoate (17)

[Formula 49]

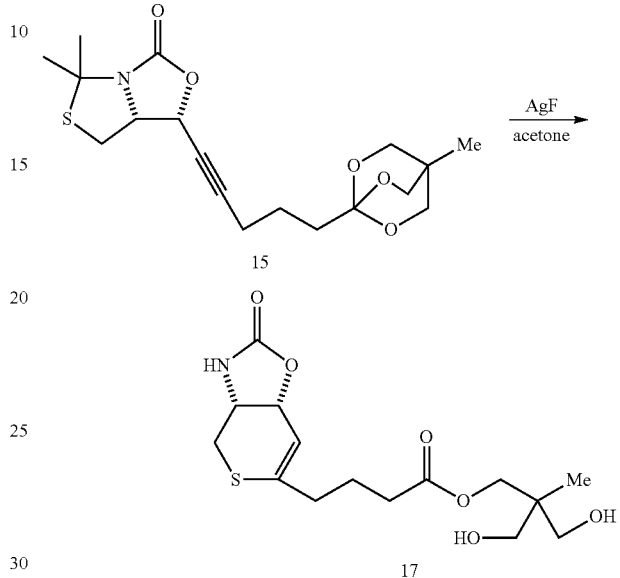

Silver(I) fluoride (34 mg, 0.26 mmol) was added to a mixed solution of acetone (1 mL) and H₂O (100 μL) containing Compound 15 (50 mg, 0.13 mmol), and the obtained mixture was then stirred for 9 hours. Thereafter, the reaction solution was passed through Celite (ethyl acetate). The obtained crude product was purified by silica gel column chromatography (ethyl acetate), so as to obtain 38 mg of the title compound 17 (yield: 77%, a white solid).

¹H NMR (CD₃OD): δ=0.93 (s, 3H), 1.80-1.90 (m, 2H), 2.34 (t, J=7.8 Hz, 2H), 2.40 (t, J=7.5 Hz, 2H), 2.66 (dd, J=13, 11 Hz, 1H), 2.99 (dd, J=13, 4.1 Hz, 1H), 3.48 (dd, J=18, 11 Hz, 4H), 4.03 (s, 2H), 4.64 (m, 1H), 4.97 (dd, J=7.3, 4.6 Hz, 1H), 5.92 (d, J=4.6 Hz, 1H)

3-Hydroxy-2-(hydroxymethyl)-2-methylpropyl 4-((3aR,6S,7aR)-2-oxohexahydro-2H-thiopyrano[3,4-d]oxazol-6-yl)butanoate (52)

[Formula 50]

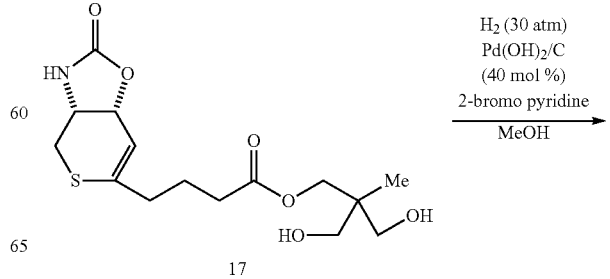

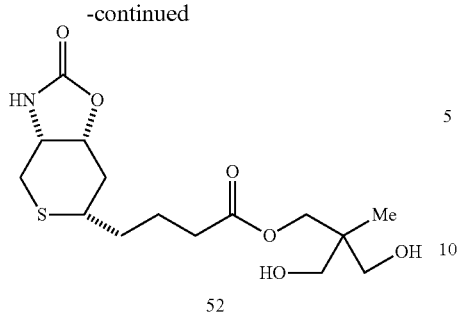

52

Palladium hydroxide on carbon (10 w/w % Pd, 40 mol %, 0.011 mmol) was added to a MeOH (1 mL) solution of Compound 17 (10 mg, 0.029 mmol) and 2-bromopyridine (28 μL, 0.29 mmol). The obtained mixture was stirred in the presence of hydrogen gas (30 atm) for 24 hours. Thereafter, the reaction solution was passed through a Celite short column (methanol). The solvent was distilled away under reduced pressure, and the obtained crude product was then purified by silica gel column chromatography (dichloromethane-methanol), so as to obtain the title compound 52 (7 mg, yield: 69%, a colorless oily substance).

$^1$H NMR (CD$_3$OD): δ=1.08 (s, 3H), 1.82-1.91 (m, 2H), 1.95-2.05 (m, 4H), 2.56 (t, J=7.8 Hz, 2H), 2.76 (dd, J=14, 5.0 Hz, 1H), 3.00 (dd, J=14, 9.2 Hz, 1H), 3.09-3.16 (m, 1H), 3.48 (dd, J=15, 11 Hz, 4H), 4.18 (s, 2H), 4.24-4.31 (m, 1H), 4.96-5.00 (m, 1H)

4-((3aR,6S,7aR)-2-Oxohexahydro-2H-thiopyrano[3,4-d]oxazol-6-yl)butanoic acid (37)

[Formula 51]

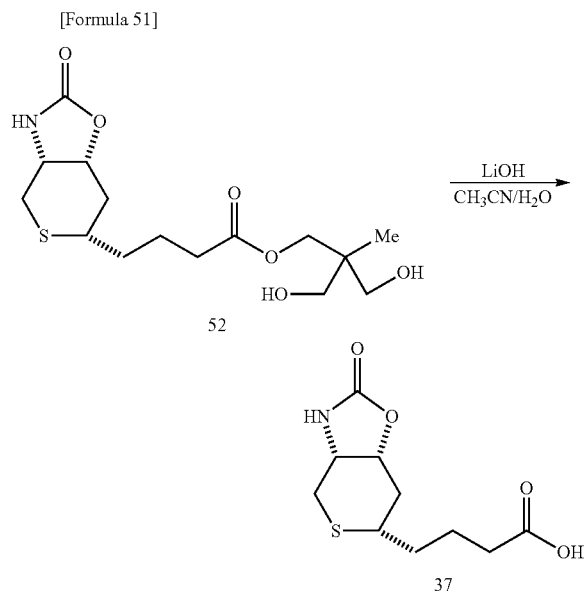

Lithium hydroxide (10 μmol) was added to a mixed solution of CH$_3$CN (500 μL) and CH$_3$CN (500 μl) containing Compound 52 (2 mg, 5.4 μmol). The obtained mixture was stirred for 12 hours, and 1 M hydrochloric acid was then added to the reaction solution to quench the reaction. The reaction solution was passed through a silica gel column chromatography (methanol). The solvent was distilled away under reduced pressure, and the obtained crude product was then purified by silica gel column chromatography (dichloromethane-methanol), so as to obtain the title compound 37 (1.1 mg, yield: 83%, a white solid).

$^1$H NMR (CD$_3$OD): δ=1.79-1.88 (m, 2H), 1.95-2.05 (m, 4H), 2.53 (t, J=7.6 Hz, 2H), 2.76 (dd, J=14, 5.1 Hz, 1H), 2.99 (dd, J=14, 9.0 Hz, 1H), 3.07-3.13 (m, 1H), 4.24-4.30 (m, 1H), 4.97-5.00 (m, 1H)

Example 2: Production of Mutant Streptavidin (1) Construction of Expression Vector The nucleotide sequence of a gene encoding a wild-type core streptavidin is shown in SEQ ID NO: 1 in the sequence listing. In the present invention, mcSA314 described in International Publication WO 2010/09455 (which is also referred to as "LISA314 WT" or "LISA314" in the present description) was used as a low immunogenic (mutant) streptavidin. The mcSA314 is a mutant streptavidin having all of the following mutations with respect to the amino acid sequence of a core streptavidin shown in SEQ ID NO: 2:
(1) a mutation, in which the tyrosine residue at position 10 is substituted with serine;
(2) a mutation, in which the tyrosine residue at position 71 is substituted with serine;
(3) a mutation, in which the arginine residue at position 72 is substituted with lysine;
(4) a mutation, in which the glutamic acid residue at position 89 is substituted with aspartic acid;
(5) a mutation, in which the arginine residue at position 91 is substituted with lysine; and
(6) a mutation, in which the glutamic acid residue at position 104 is substituted with asparagine.

The expression vector was designed, such that a fusion protein comprising the above-described wild-type streptavidin or modified streptavidin and a subtilisin prodomain portion used as a tag for purification was expressed. A vector, into the N'-terminal side of which a subtilisin pro-domain gene sequence had been incorporated, namely, a pPAL7 vector (manufactured by BIO-RAD) was used, and the codon was optimized, so as to prepare a vector that expresses a fusion protein, in which a wild-type streptavidin or a modified streptavidin was fused with the C-terminal side thereof.

Specifically, PCR was carried out using the above-described sequence as a template and also using the following Primers 1 and 2, which added a HindIII site onto the 5-terminal side and an EcoRI site onto the 3-terminal side by PCR. Then, the PCR product was treated with the restriction enzymes HindIII and EcoRI.

```
Primer 1:
                                     (SEQ ID NO: 13)
GCTCTTCAAAGCTTTGGCCGAAGCTGGTATCACTG Primer 2:
                                     (SEQ ID NO: 14)
CTCGAGGAATTCTTAGCTAGCAGCAGAAGGCTTAAC
```

The thus restriction enzyme-treated sample was subjected to electrophoresis, and then to gel purification. Likewise, the pPAL7 vector (manufactured by BIO-RAD) was also treated with enzymes and was then subjected to gel purification. The purified vector was ligated to the purified PCR product according to a designated method using 2× Rapid Ligation Buffer and T4 DNA Polymerase (both of which were manufactured by Promega). *Escherichia coli* was transformed by adding 2 μl of the ligation product to 50 μl of DH5α competent cells (manufactured by TOYOBO). A plasmid was extracted using Miniprep Kit (manufactured by QIAGEN). The obtained plasmid was subjected to sequence analysis, so as to confirm its sequence.

(2) Production of Mutant Strains

Oligo DNA used in the production of each variant was designed in accordance with the instruction manual included with PrimerSTAR Mutagenesis Basal Kit (TAKARA BIO, INC.), such that 15 nucleotides on the 5' side would be overlapped. Using the below-mentioned primers, and also using a pCold TF vector into which LISA314 had been inserted as a template, a codon sequence was altered by the substitution of the nucleotide sequence according to the Site-Directed Mutagenesis method, so as to modify the amino acid sequence. Thereafter, a template plasmid was cleaved with the restriction enzyme DpnI, and the *Escherichia coli* was transformed.

```
Primers:
S45N Fw:
                                        (SEQ ID NO: 15)
TATGAAAACGCCGTGGGTAATGCGGAA S45N Rv:
                                        (SEQ ID NO: 16)
CACGGCGTTTTCATAGGTGCCGGTCAG D128N Fw:
                                        (SEQ ID NO: 17)
CGTTGGCGGTGCTGATGCTCGTATCAACAC D128N Rv:
                                        (SEQ ID NO: 18)
GGTGCTGATGCTAAGATCAACACTCAGTGG
```

S45N means a mutation in which the serine residue (S) at position 33 is substituted with asparagine (N) in the amino acid sequence of the core streptavidin shown in SEQ ID NO: 2.

D128N means a mutation in which the aspartic acid residue (D) at position 116 is substituted with asparagine (N) in the amino acid sequence of the core streptavidin shown in SEQ ID NO: 2.

As described above, there was produced *Escherichia coli* that generates a mutant streptavidin (which is also referred to as "LISA314 N45 N128" in the present description) having the following mutations with respect to the amino acid sequence of the core streptavidin shown in SEQ ID NO: 2:
(1) a mutation, in which the tyrosine residue at position 10 is substituted with serine;
(2) a mutation, in which the tyrosine residue at position 71 is substituted with serine;
(3) a mutation, in which the arginine residue at position 72 is substituted with lysine;
(4) a mutation, in which the glutamic acid residue at position 89 is substituted with aspartic acid;
(5) a mutation, in which the arginine residue at position 91 is substituted with lysine;
(6) a mutation, in which the glutamic acid residue at position 104 is substituted with asparagine;
(7) a mutation, in which the serine residue at position 33 is substituted with asparagine; and
(8) a mutation, in which the aspartic acid residue at position 116 is substituted with asparagine. The amino acid sequence having the mutations as described in (1) to (8) above, with respect to the amino acid sequence shown in SEQ ID NO: 2, is shown in SEQ ID NO: 3.

(3) Expression of Recombinant Protein

*Escherichia coli* BL21 (BIO-RAD) was transfected with a pPAL7 expression vector, into which the gene sequence of a mutant streptavidin had been incorporated, according to an ordinary method. The expression of a protein was carried out as follows. That is to say, the *Escherichia coli* was cultured at 37° C., until the cell density in the culture solution of *Escherichia coli* became 0.5 to 0.7 in OD (600 nm). Thereafter, IPTG (isopropyl-β-D-thiogalactopyranoside) was added to the culture solution to a final concentration of 1 mM, so that protein expression was induced. The culture was carried out at a temperature of 10° C. to 30° C., and preferably at 16° C., for 24 hours or more. After completion of the culture, a cell mass was centrifuged to collect cells, and the collected cells were then preserved at −20° C. until protein purification.

(4) Partial Purification of Recombinant Protein

The recombinant protein (LISA314-V11) was partially purified by affinity chromatography in which the binding ability of a modified subtilisin to a subtilisin prodomain was utilized. Specifically, a column in which the modified subtilisin was immobilized on Sperflow 6% agarose beads (Bio-Scale Mini Profinity eXact Cartridge, BIO-RAD) was used.

For preparation of *Escherichia coli*, 10 mM sodium phosphate, pH7.2-5.6, 10× BugBuser reagent (Novagen), and nucleolytic enzyme (Benzonase) were added to cells as a cell-dissolving solution, and the cells were lysed. Such cell lysis was carried out at room temperature, and the obtained lysate was then subjected to centrifugation at 35,000×g for 30 minutes. After completion of the centrifugation, the supernatant was obtained as a total soluble protein.

Binding buffer and/or washing buffer 1 (10 mM sodium phosphate), washing buffer 2 (10 M sodium phosphate, 300 mM), elution buffer (10 M sodium acetate, 100 mM sodium fluoride), column regeneration buffer (100 mM phosphoric acid), and column preservation buffer (10 mM sodium phosphate) were used in purification. With regard to the pH of the buffer used in purification of a natural streptavidin, the pH was set at pH 6.1. On the other hand, in purification of a modified streptavidin, the pH was set at pH 6.8.

Purification was carried out according to the following procedures.

The column was equilibrated with 10 column volumes of buffer. Subsequently, the total soluble protein from *Escherichia coli* was applied at a flow rate of 2 ml/min to the column. After the total soluble protein had been applied to the column, the column was washed with 10 column volumes of washing buffer 1. Subsequently, the column was washed with 10 column volumes of washing buffer 2. Thereafter, 1 column volume of elution buffer was injected into the column, and incubation was then carried out for 30 minutes at room temperature. Completion of the incubation, the protein was eluted with 3 column volumes of elution buffer. After that, the column was regenerated with 5 column volumes of column regeneration buffer. Finally, the column was washed with 5 column volumes of column preservation buffer to terminate purification.

The results of purification are shown in FIG. 1.

(5) High-Level Purification of Partially Purified Recombinant Protein

Hereinafter, the pH of the buffer for the modified streptavidin was set at pH 7.0.

In preparation for purification with a ceramic hydroxyapatite column, the partially purified recombinant protein was concentrated by centrifugal filtration using an ultrafiltration membrane of 10,000 MWCO. After completion of the concentration, the buffer was replaced with a 5 mM sodium phosphate solution, using a desalination column. As such a ceramic hydroxyapatite column, CHT2-1 (BIO-RAD) was used, and the flow rate was set at 2 ml/min in all operations. First, the column was equilibrated with 10 column volumes of 5 mM sodium phosphate. Next, buffer-replaced partial purification sample was applied to the column, so that it was adsorbed on the column. The column was washed with 6 column volumes of buffer, and a protein was then eluted using 5 mM sodium phosphate, 500 mM sodium chloride buffer.

Example 3: Competitive Analysis with Biotin-HRP Label

Figure 2:
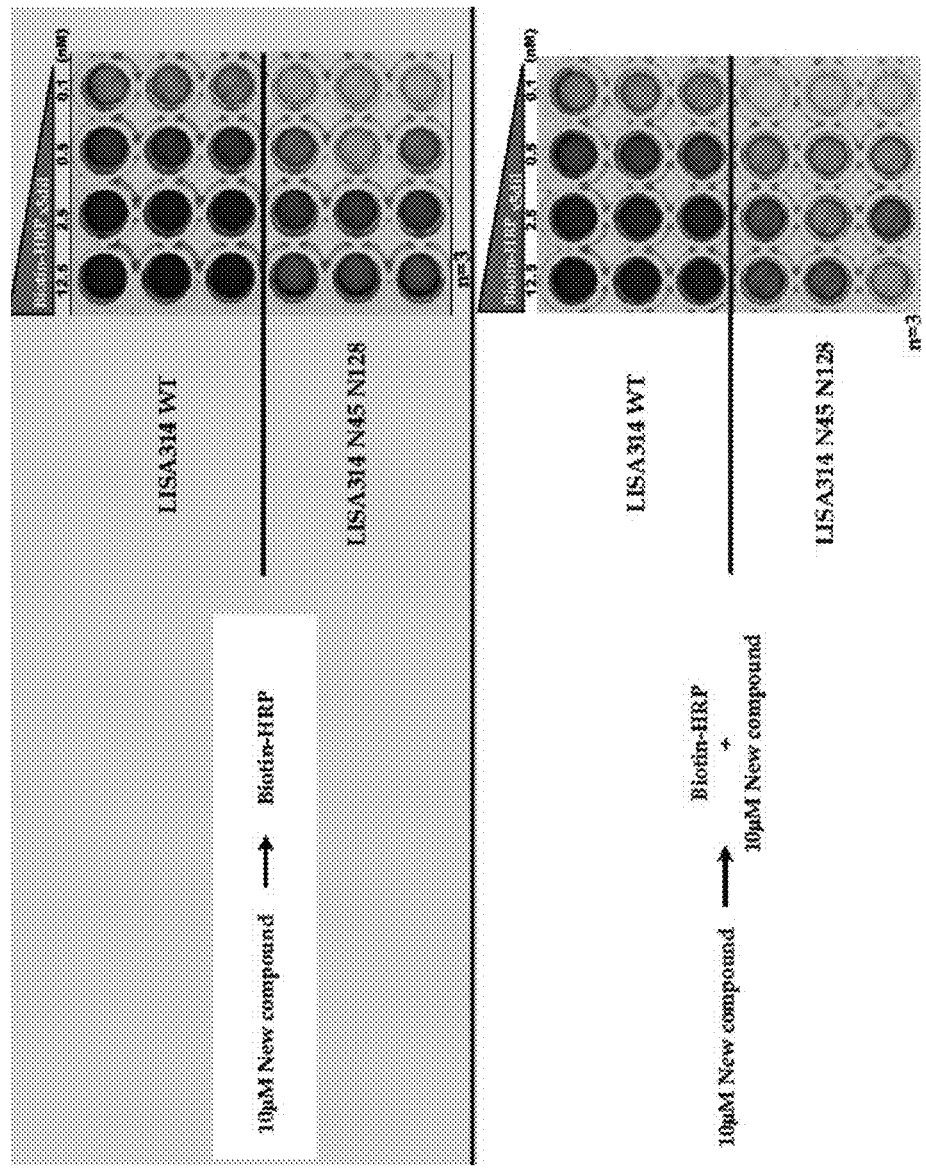
FIG. 2 shows the results of the competitive analysis of a recombinant protein with a biotin-HRP label.

The purified mutant protein was consolidated on ELISA Plate H (Sumitomo Bakelite Co., Ltd.) under conditions of 5 μg/mL, 100 μl, 4° C., and overnight. After preparation of a solid phase, blocking was carried out at 200 μl/well for 5 minutes, using SuperBlock Blocking Buffer (Thermo Scientific). Thereafter, 10 μM Compound 11 described in Example 1 (namely, (3aS,4S,6aR)-2-oxotetrahydrothieno[3,4-d][1,3]dioxol-4-yl)pentanoic acid) was allowed to react therewith in an amount of 100 μl/well at room temperature for 1 hour. After the plate had been washed, a 12.5 nM Biotin-HRP label was allowed to react with the resultant in an amount of 100 μl/well at room temperature for 1 hour. After the plate had been washed, a reaction was carried out in an amount of 100 μl/well at room temperature for 30 minutes. As a result of a comparison made in terms of the level of color development (FIG. 2), it was confirmed that Compound 11 competed with the label.

Example 4: Production of LISA314 Variant

(1) Preparation of Expression Vector for LISA314 Variant

Oligo DNA used in the production of each variant was designed in accordance with the instruction manual included with PrimerSTAR Mutagenesis Basal Kit (TAKARA BIO, INC.), such that 15 nucleotides on the 5' side would be overlapped. Using the below-mentioned primers, and also using, as a template, a pCold TF vector into which LISA314 had been inserted, a codon sequence was altered by the substitution of the nucleotide sequence according to the Site-Directed Mutagenesis method, so as to modify the amino acid sequence. Thereafter, a template plasmid was cleaved with the restriction enzyme DpnI, and the *Escherichia coli* was transformed.

```
Primers:
LISA314 V21 Fw:
                                    (SEQ ID NO: 19)
TGGAGCgatCAGCTGGGCgatACCTTT LISA314 V21 Rv:
                                    (SEQ ID NO: 20)
CAGCTGatcGCTCCAGGTGCCGGTAAT
```

LISA314 V21 that is a LISA314 variant further has N23D and S27D mutations with respect to LISA314. N23D means a mutation in which the asparagine residue (N) at position 11 is substituted with aspartic acid (D) in the amino acid sequence of the core streptavidin shown in SEQ ID NO: 2. S27D means a mutation in which the serine residue (S) at position 15 is substituted with aspartic acid (D) in the amino acid sequence of the core streptavidin shown in SEQ ID NO: 2.

That is to say, LISA314 V21 is a mutant streptavidin having the following mutations with respect to the amino acid sequence of the core streptavidin shown in SEQ ID NO: 2:

(1) a mutation, in which the tyrosine residue at position 10 is substituted with serine;
(2) a mutation, in which the tyrosine residue at position 71 is substituted with serine;
(3) a mutation, in which the arginine residue at position 72 is substituted with lysine;
(4) a mutation, in which the glutamic acid residue at position 89 is substituted with aspartic acid;
(5) a mutation, in which the arginine residue at position 91 is substituted with lysine;
(6) a mutation, in which the glutamic acid residue at position 104 is substituted with asparagine;
(7) a mutation, in which the asparagine residue at position 11 is substituted with aspartic acid; and
(8) a mutation, in which the serine residue at position 15 is substituted with aspartic acid. This amino acid sequence is shown in SEQ ID NO: 4.

(2) Expression of Recombinant Protein

Each mutant protein was allowed to express in accordance with the manual included with a pCold TF vector (TAKARA BIO, INC.). Specifically, *Escherichia coli* BL21 (TAKARA BIO, INC.) was transformed with an expression vector according to an ordinary method. The transformed *Escherichia coli* was then cultured at 37° C., so that the cell density in the culture solution of *Escherichia coli* became OD (600 nm)=0.5 to 0.7. Thereafter, the culture was left at rest at 15° C. for 1 hour. Thereafter, IPTG (isopropyl-β-D-thiogalactopyranoside) was added to the resulting culture to a final concentration of 1 mM, so as to induce the expression of the protein. After that, a culture was carried out at 15° C. for 24 hours. After completion of the culture, a cell mass was centrifuged to collect cells, and the collected cells were then preserved at −20° C. until purification of the protein.

(3) Partial Purification of Recombinant Protein

For partial purification of the recombinant protein, affinity chromatography was carried out using 6×His-tag (SEQ ID NO: 39). Specifically, Ni Sepharose 6 Fast Flow (GE Healthcare Biosciences) was used as a carrier.

For preparation of *Escherichia coli*, 3 mL of B-PER (Thermo SCIETIFIC) Lisonase Bioprocessing Reagent was added as a cell-dissolving solution to 1 mL of B-PER, so that the cells were lysed. The cell lysis was carried out at room temperature, and the obtained lysate was then subjected to centrifugation at 27,000×g for 20 minutes. After completion of the centrifugation, the supernatant was obtained as a total soluble protein.

Using 10 column volumes of binding/washing buffer (20 mM Tris-NaCl, 500 mM NaCl, pH 8), the column was equilibrated, and after application of the sample to the column, the column was washed. In addition, the binding protein was eluted with 3 column volumes of elution buffer (20 mM Tris-NaCl, 500 mM NaCl, 400 mM imidazole, pH 8).

(4) Cleavage and Removal of TF Tag

5 U of HRV 3C Protease was used to 5 μg of the partially purified protein to cleave the tag. After completion of the reaction at 4° C. for 24 hours, the reaction product was denatured with a denaturation buffer (20 mM Tris-NaCl, 6 M guanidine hydrochloride, 500 mM NaCl, pH 8), and was then subjected to affinity chromatography using Ni Sepharose 6 Fast Flow.

Example 5: Analysis of Crystal Structure (1) Crystallization Conditions

LISA314-Biotin

Figure 3:
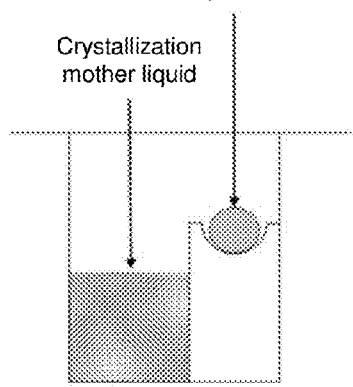
FIG. 3 shows a sitting drop vapor diffusion method.

Applying a sitting drop vapor diffusion method, crystallization was carried out at 20° C. (FIG. 3). A protein solution was 9 mg/ml LISA314, 15 mM tris-HCl pH 7.5, and 150 mM NaCl. An excessive amount of biotin was added to the solution during the purification of LISA314. As a crystallization mother liquid (60 µl), 0.2 M ammonium sulfate, 0.1 M sodium acetate trihydrate pH 5.2, and 22% (w/v) polyethylene glycol 4000 were used. As an internal fluid for crystallization, a mixed solution of 0.5 µl of the protein solution and 0.5 µl of the crystallization mother liquid was used.

LISA314-V21-Iminobiotintail

Applying a sitting drop vapor diffusion method, crystallization was carried out at 20° C. A protein solution was 10 mg/ml LISA314-V21, 20 mM tris-HCl pH 7.5, and 250 mM NaCl. An excessive amount of Iminobiotintail (Compound 29 of Example 1, the structure of which is shown below) was added to the solution during the purification of LISA314-V21.

[Formula 52]

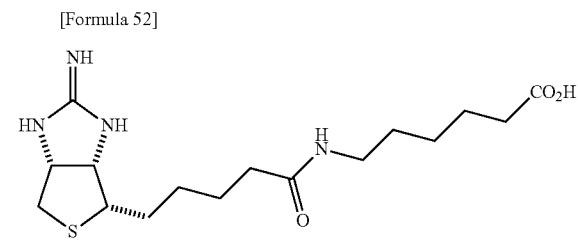

As a crystallization mother liquid (60 µl), 0.1 M Sodium acetate trihydrate pH 4.5, and 30% (w/v) Polyethylene glycol 1500 were used. As an internal fluid for crystallization, a mixed solution of 0.5 µl of the protein solution and 0.5 µl of the crystallization mother liquid was used.

(2) Results

Figure 4:
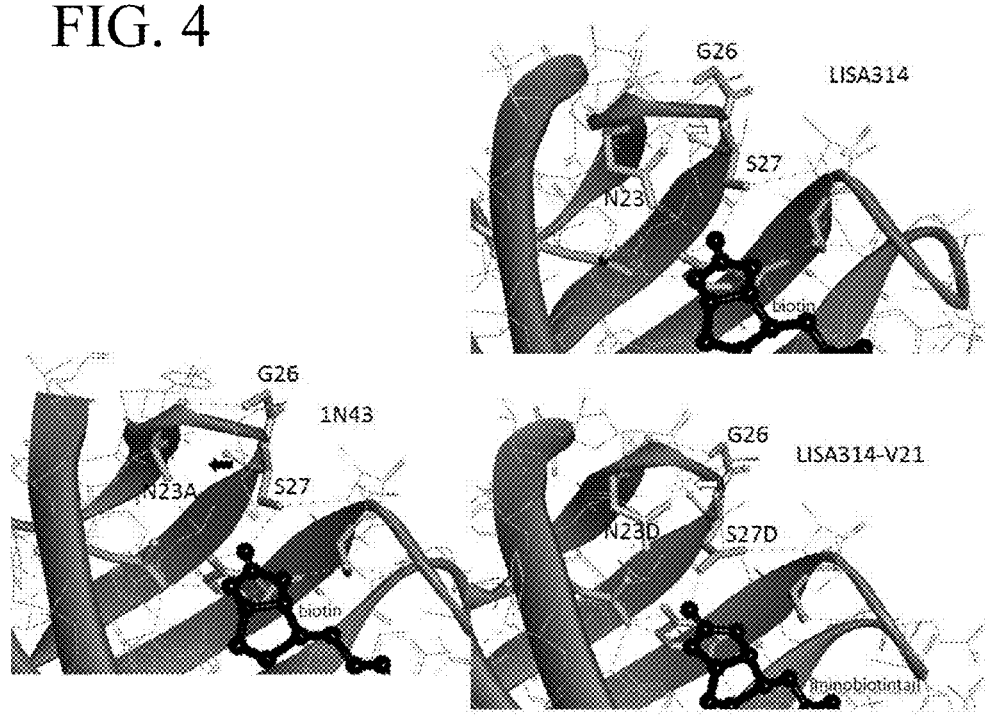
FIG. 4 shows the crystal structures of LISA314 and LISA314-V21.

The results obtained by analyzing the crystal structure are shown in FIG. 4 and FIG. 5.

An N23A mutant streptavidin formed by substituting with Ala, the amino acid at position 23 (Asn23) (that is position 11 in the amino acid sequence of the core streptavidin shown in SEQ ID NO: 2) of a streptavidin having a hydrogen bond with biotin has been reported to have a significantly reduced binding ability with biotin. Moreover, the crystal structure of a complex of this mutant streptavidin and biotin has also been reported (PDB ID, 1N43). If the steric structure of 1N43 and the neighborhood of N23A are compared with the crystal structure of our LISA314, the Asn23 of LISA314 forms a hydrogen bond with Gly26 close thereto, and they interact with each other (the dotted line connecting N23 of LISA314 with G26, which is indicated by the outlined arrow in the upper right view of FIG. 4). On the other hand, no hydrogen bonds corresponding to Ala23 and Gly26 are present in 1N43 (the portion indicated by the black arrow in 1N43 in the lower left of FIG. 4). Thus, the N23A mutation in 1N43 was considered to destabilize the loop structure from N23 to S27 in comparison to LISA314, and it was considered that, by performing the N23D mutation, the hydrogen bond between this amino acid at position 23 (that is position 11 in the amino acid sequence of the core streptavidin shown in SEQ ID NO: 2) and Gly26 would be maintained, and that the loop structure from N23 to S27 would become stable. In fact, as shown in the lower right view of FIG. 4, in the crystal structure of LISA314-V21, on which the N23D mutation has been performed, the aforementioned hydrogen bond is conserved (the dotted line indicated by the outlined arrow). The mutant streptavidin LISA314-V21 was produced with the expectation that it was anticipated to have a strong interaction not with biotin, but with iminobiotin. Accordingly, in addition to the N23D mutation, an S23D mutation was performed on the mutant streptavidin, so that the Asp27 of LISA314-V21 interacted with the N atom of iminobiotin.

Example 6: Affinity Analysis by SPR (1) Construction of Expression Vector (LISA314 V21; N23D, S27, Etc.)

A protein to be used in affinity analysis by Biacore was expressed by a pET-21a (+) vector (Millipore/Merch), and the inclusion body was then refolded to prepare a recombinant protein. Specifically, a pET-21a (+) vector was linearized with the restriction enzymes BamHI and XhoI. Subsequently, PCR primers were designed so as to be suitable for the linearized vector in accordance with the manual included with In-Fusion HD Cloning Kit (Clontech), and using the aforementioned each variant LISA314 V21 expression vector (pCold TF) as a template, PCR was carried out. The amplified sequence was subjected to agarose gel electrophoresis, so that a band of interest was cut out. Thereafter, DNA was extracted and was then purified. The linearized vector was ligated to the purified PCR product using In-Fusion HD Cloning Kit.

```
Primers:
For pET21a(+) Fw:
                                  (SEQ ID NO: 21)
AATGGGTCGCGGATCCGCCGAAGCAGGTATTACCGGCAC For pET21a(+) Rv:
                                  (SEQ ID NO: 22)
GGTGGTGGTGCTCGAGGCTGGCCGCGCTCGGTTTAACTTTG
```

(2) Construction of LISA314 V21 Variant Expression Vector

Oligo DNA used in the production of various variants of LISA314 V21 was designed in accordance with the instruction manual included with PrimerSTAR Mutagenesis Basal Kit (TAKARA BIO, INC.), such that 15 nucleotides on the 5' side would be overlapped. Using the below-mentioned primers, and also using, as a template, a vector into which the aforementioned LISA314 V21 had been inserted, a codon sequence was altered by the substitution of the nucleotide sequence according to the Site-Directed Mutagenesis method, so as to modify the amino acid sequence. Thereafter, a template plasmid was cleaved with the restriction enzyme DpnI, so that the Escherichia coli was transformed.

```
Primers
S45A Fw:
                                  (SEQ ID NO: 23)
TATGAAgcaGCCGTGGGTAATGCGGAA
```

-continued

S45A Rv:
(SEQ ID NO: 24)
CACGGCtgcTTCATAGGTGCCGGTCAG

S45Q Fw:
(SEQ ID NO: 25)
TATGAAcagGCCGTGGGTAATGCGGAA

S45Q Rv:
(SEQ ID NO: 26)
CACGGCctgTTCATAGGTGCCGGTCAG

S45L Fw:
(SEQ ID NO: 27)
TATGAActgGCCGTGGGTAATGCGGAA

S45L Rv:
(SEQ ID NO: 28)
CACGGCcagTTCATAGGTGCCGGTCAG

S45I Fw:
(SEQ ID NO: 29)
TATGAAatcGCCGTGGGTAATGCGGAA

S45I Rv:
(SEQ ID NO: 30)
CACGGCgatTTCATAGGTGCCGGTCAG

S45H Fw:
(SEQ ID NO: 31)
TATGAAcatGCCGTGGGTAATGCGGAA

S45H Rv:
(SEQ ID NO: 32)
CACGGCatgTTCATAGGTGCCGGTCAG

S45T Fw:
(SEQ ID NO: 33)
TATGAAaccGCCGTGGGTAATGCGGAA

S45T Rv:
(SEQ ID NO: 34)
CACGGCggtTTCATAGGTGCCGGTCAG

S45V Fw:
(SEQ ID NO: 35)
TATGAAgtgGCCGTGGGTAATGCGGAA

S45V Rv:
(SEQ ID NO: 36)
CACGGCcacTTCATAGGTGCCGGTCAG

S45N Fw:
(SEQ ID NO: 37)
TATGAAAACGCCGTGGGTAATGCGGAA

S45N Rv:
(SEQ ID NO: 38)
CACGGCGTTTTCATAGGTGCCGGTCAG

S45A, S45Q, S45L, S45I, S45H, S45T, S45V, and S45N indicate that the serine residue at position 33 is substituted with alanine (A), glutamine (Q), leucine (L), isoleucine (I), histidine (H), threonine (T), valine (V) and asparagine (N), respectively, in the amino acid sequence of the core streptavidin shown in SEQ ID NO: 2. That is to say, mutants, in which any one of the above-described amino acid mutations S45A, S45Q, S45L, S45I, S45H, S45T, S45V and S45N is further introduced into LISA314 V21, are produced. The amino acid sequences of these mutants are shown in SEQ ID NOS: 5 to 12 in the sequence listing.

(3) Expression of Recombinant Protein

For the expression of each mutant protein, *Escherichia coli* BL21 (DE3) (Millipore/Merch) was transfected with a pET-21a (+) vector, into which a gene expressing a variant of interest had been incorporated, according to an ordinary method. Thereafter, the *Escherichia coli* was cultured at 37° C., until the cell density in the culture solution of *Escherichia coli* became 0.5 to 0.8 in OD (600 nm). Thereafter, IPTG (isopropyl-β-D-thiogalactopyranoside) was added to the culture solution to a final concentration of 1 mM, so that protein expression was induced. The culture was carried out for 4 to 16 hours. After completion of the culture, a cell mass was centrifuged to collect cells, and the collected cells were then preserved at −20° C. until protein purification.

(4) Preparation of Recombinant Protein (Inclusion Body)

For preparation of *Escherichia coli*, 3 mL of B-PER (Thermo SCIETIFIC) Lisonase Bioprocessing Reagent was added as a cell-dissolving solution to 1 mL of B-PER, so that the cells were lysed. The cell lysis was carried out at room temperature, and the obtained lysate was then subjected to centrifugation at 27,000×g for 20 minutes. After completion of the centrifugation, the supernatant was discarded, and a pellet was recovered as an inclusion body. The recovered inclusion body was resuspended in 10 mL of B-PER that had been 10 times diluted with Milli Q water, and it was then recovered by centrifugation at 27,000×g for 20 minutes. This washing operation was carried out three times. Finally, in order to remove the surfactant, the inclusion body was resuspended in Milli Q water and it was then recovered by centrifugation. The recovered inclusion body was subdivided and was then cryopreserved at −80° C.

(5) Refolding of Inclusion Body

The inclusion body was refolded by solubilizing the cryopreserved inclusion body with a denaturation buffer (20 mM Tris-HCl, 6 M guanidine hydrochloride, 200 mM NaCl, pH 1.5). In order to remove biotin, the inclusion body was dialyzed twice for 4 hours against a 100-fold volume of dialysis buffer (the same as the denaturation buffer). Thereafter, the concentration was adjusted with a dialysis buffer, so that the protein concentration in the solubilized liquid at an absorbance of 280 nm could be 40 to 50 mg/mL. For refolding, a dilution method was applied. Specifically, 100 μL of the protein solution having the regulated concentration was added dropwise to 50 mL of a dilution buffer (20 mM Tris-HCl, 200 mM NaCl, pH 8.0) that was being stirred with a stirrer, so that the protein solution was diluted and the protein was refolded.

(6) Purification of Refolded Protein

The protein that had been refolded by the dilution method was subjected to affinity chromatography using complete His-Tag Purification Resin (Roche). Such a purified protein was concentrated, and was then subjected to gel filtration chromatography to fractionate a tetramer fraction.

Figure 6:
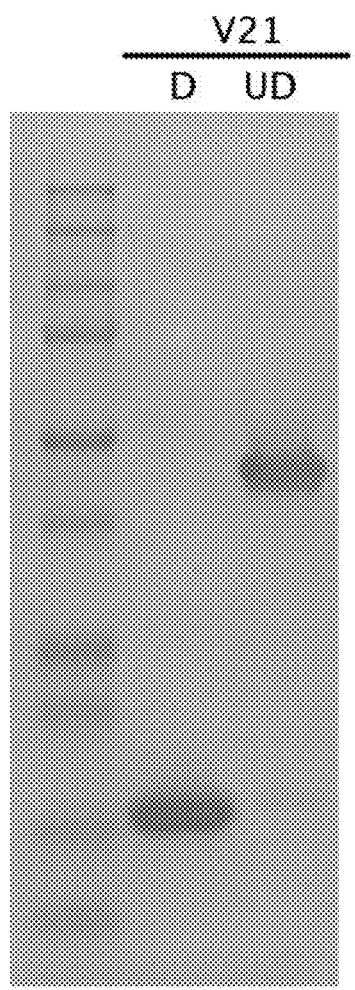
FIG. 6 shows an example of the purification of a refolded protein.

An example of the purification of the refolded protein is shown in FIG. 6.

(7) Affinity Analysis of Compound by SPR

For affinity analysis, Biacore T100 was used. Specifically, the protein that had been fractionated by gel filtration chromatography was immobilized using Sensor Chip NTA. As a running buffer, 0.5% Tween20, HBS-P+ was used. Immobilization of the protein on nickel NTA and ligand capture were carried out according to the template program included therewith.

(8) Biacore Assay

The amount of a ligand immobilized on a sensor chip was adjusted within the range of 1608 RU to 8042 RU, so as to suppress mass transport limitation. As analytes, biocytin and Compound 29 (the structure thereof is shown below) synthesized in Example 1 were used. It is to be noted that biocytin is a main existence form of biotin.

[Formula 52]

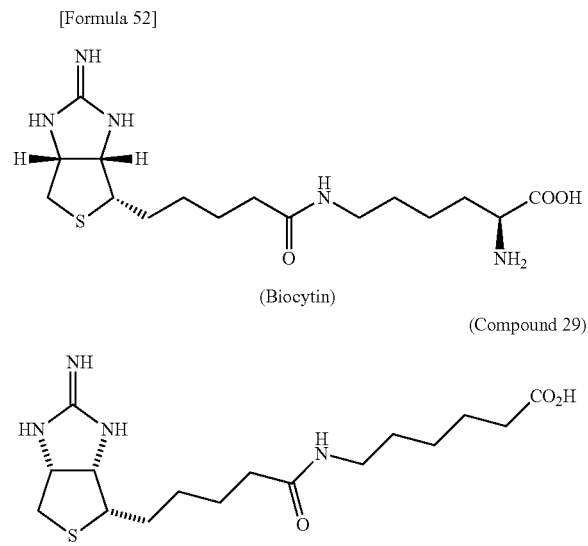

(Biocytin)

(Compound 29)

Figure 7:
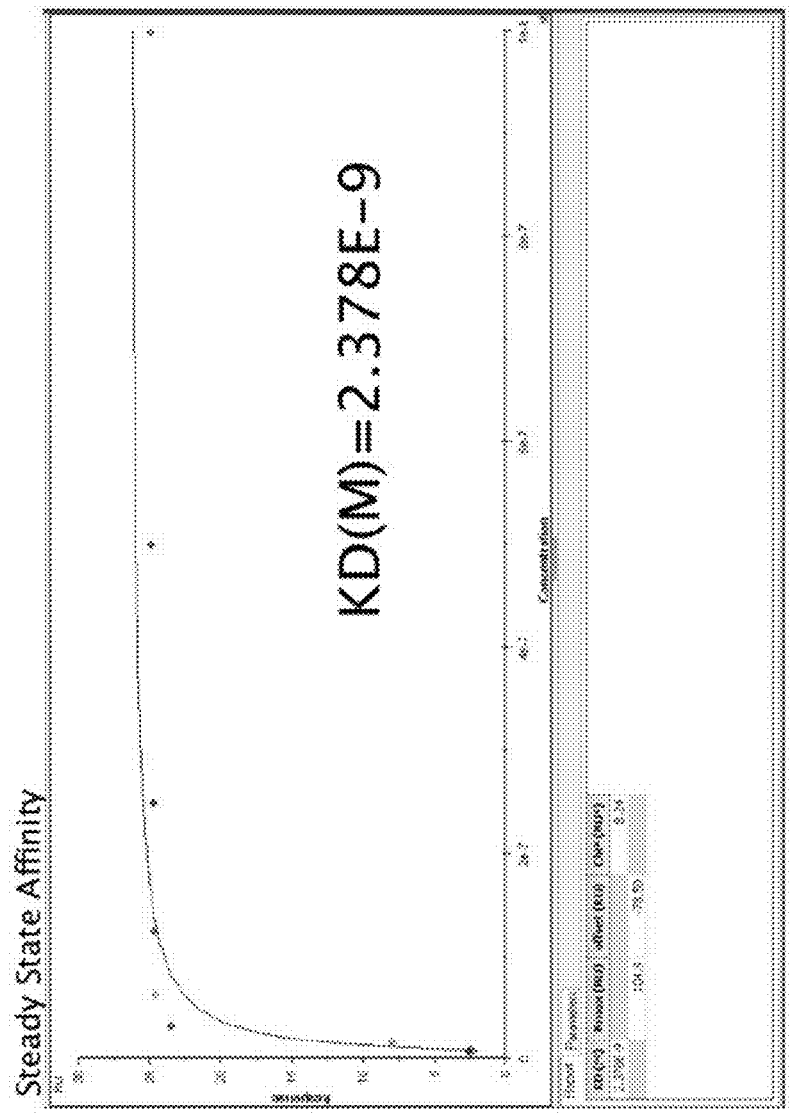
FIG. 7 shows a sensorgram obtained from the SPR analysis of the interaction of biocytin with LISA314 WT.
Figure 8:
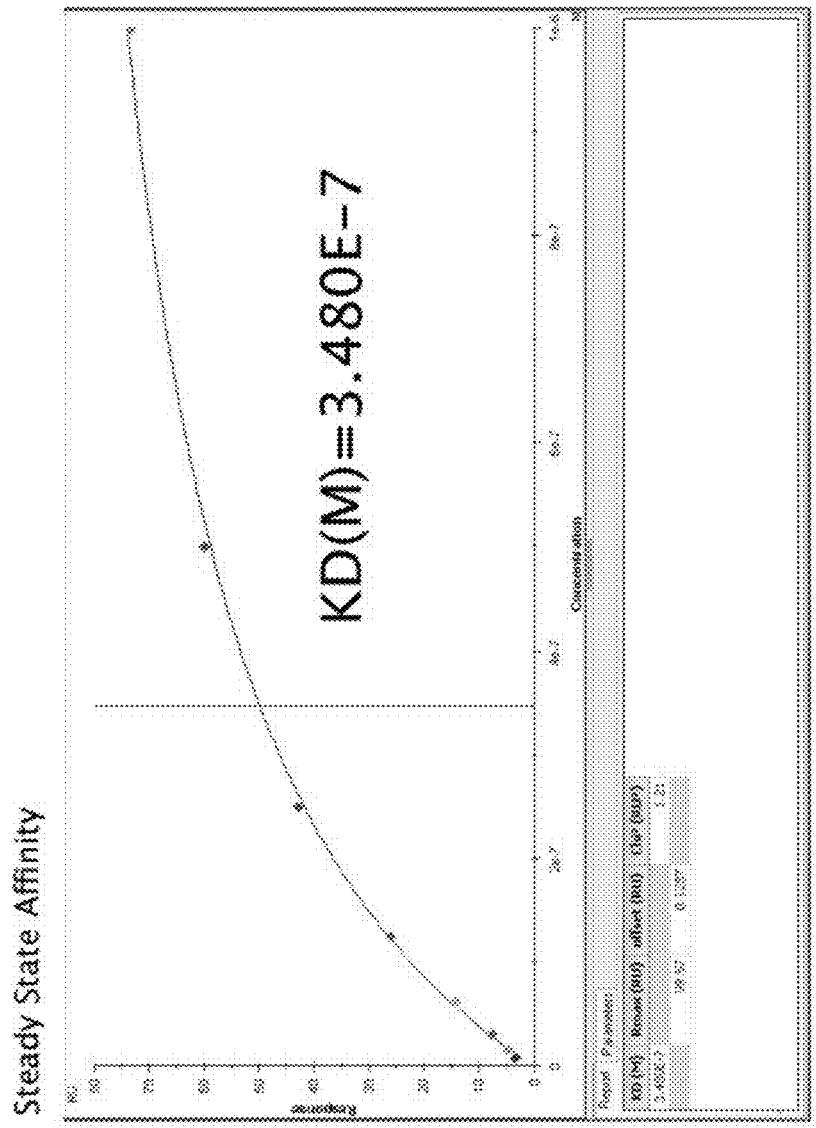
FIG. 8 shows a sensorgram obtained from the SPR analysis of the interaction of biocytin with LISA314 V21.
Figure 9:
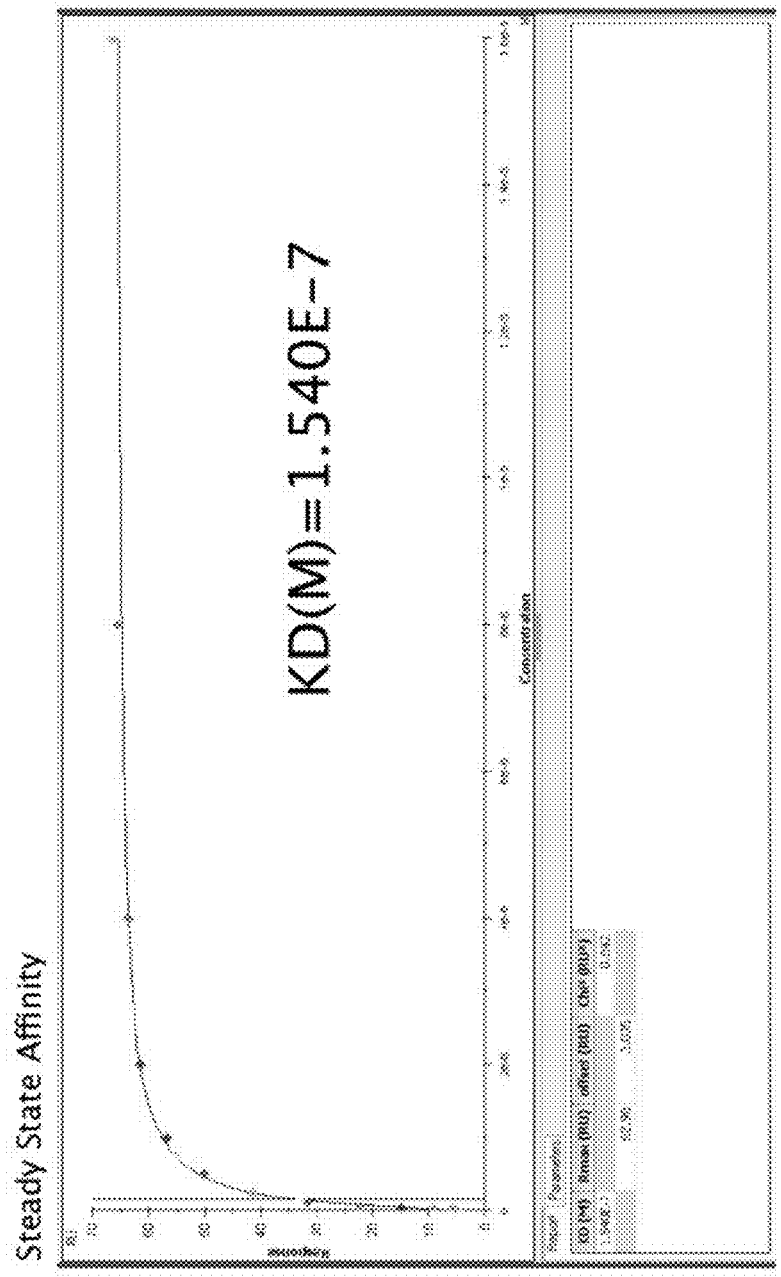
FIG. 9 shows a sensorgram obtained from the SPR analysis of the interaction of Compound 29 with LISA314 V21.

With regard to the concentrations of the analytes, in the case of biocytin, eight 2-fold dilution series were prepared from 1 μM, and in the case of Compound 29, twelve 2-fold dilution series were prepared from 16 μM. The measurement was carried out at a flow rate of 30 μl/min, for a contact time of 120 seconds, and for a dissociation time of 600 seconds. For the analysis of the data, sensorgrams for all concentrations were incorporated into analysis software, the equilibrium value analysis was then carried out, and the dissociation constant KD was then calculated. The graphs are shown in FIG. 7 to FIG. 9, and the calculated KD values are shown in Table 1. As a result, it was found that the interaction of LISA314 V21 with Compound 29 is approximately two times stronger than the interaction of LISA314 V21 with biocytin.

TABLE 1

|  | Dissociation constant: KD (M) |
| --- | --- |
| Biocytin and LISA314 WT | 2.378E−9 |
| Biocytin and LISA314 V21 | 3.480E−7 |
| Compound 29 and LISA314 V21 | 1.540E−7 |

The invention claimed is:

1. A mutant streptavidin comprising the amino acid sequence as set forth in any one of SEQ ID NOS: 3 to 12.

2. A mutant streptavidin-molecular probe conjugate which is obtained by conjugating a molecular probe to the mutant streptavidin according to claim 1.

3. A therapeutic agent or an in-vivo or in-vitro diagnostic agent, which comprises the mutant streptavidin-molecular probe conjugate according to claim 2.

4. A therapeutic, or in-vivo or in-vitro diagnostic kit, which comprises:
(a) a mutant streptavidin-molecular probe conjugate which is obtained by conjugating a molecular probe to the mutant streptavidin according to claim 1; and
(b) an in-vivo or in-vitro diagnostic or therapeutic substance that has been labeled with a compound represented by the following formula (1):

[Formula 1]

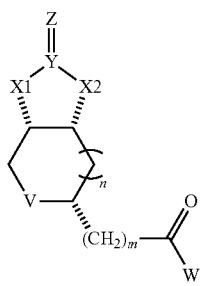

(1)

wherein X1 and X2 each independently represent O or NH; Y represents C or S; Z represents O, S or NH; V represents S or $S^+$—$O^-$; n represents an integer of 0 or 1; m represents an integer of 1 to 10; and W represents —OH, —NH$(CH_2)_p$COOH, or —NH$(CH_2)_q$C (NH$_2$) COOH, wherein p and q each independently represent an integer of 1 to 10.

5. A reagent kit for use in treatments or in-vivo or in-vitro diagnoses, which comprises:
(a) the mutant streptavidin according to claim 1 with a reduced affinity for natural biotin or biocytin; and
(b) a modified biotin having a high affinity for the mutant streptavidin.

6. A therapeutic, or in-vivo or in-vitro diagnostic kit, which comprises:
(a) a conjugate of the mutant streptavidin according to claim 1 with a reduced affinity for natural biotin or biocytin and a molecular probe; and
(b) an in-vivo or in-vitro diagnostic or therapeutic substance that has been labeled with a modified biotin having a high affinity for the mutant streptavidin.

7. A therapeutic, or in-vivo or in-vitro diagnostic kit, which comprises:
(a) a mutant streptavidin-molecular probe conjugate which is obtained by conjugating a molecular probe to the mutant streptavidin according to claim 4; and
(b) an in-vivo or in-vitro diagnostic or therapeutic substance that has been labeled with
a compound represented by the following formula (2):

[Formula 2]

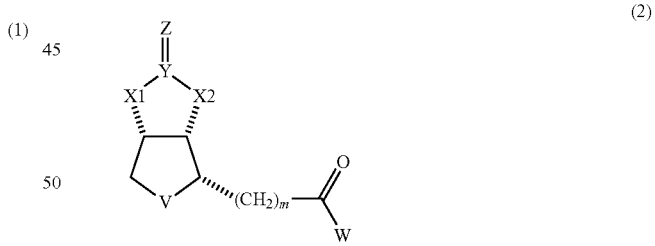

(2)

wherein X1 and X2 each independently represent O or NH; Y represents C or S; Z represents O, S or NH; V represents S or $S_+$—$O^-$; m represents an integer of 1 to 10; and W represents —OH, —NH909$(CH_2)_p$COOH, or —NH$(CH_2)_q$C(NH$_2$)COOH, wherein p and q each independently represent an integer of 1 to 10.

8. A therapeutic, or in-vivo or in-vitro diagnostic kit, which comprises:
(a) a mutant streptavidin-molecular probe conjugate which is obtained by conjugating a molecular probe to the mutant streptavidin according to claim 4; and
(b) an in-vivo or in-vitro diagnostic or therapeutic substance that has been labeled with a compound represented by any one of the following formulae:

[Formula 3]
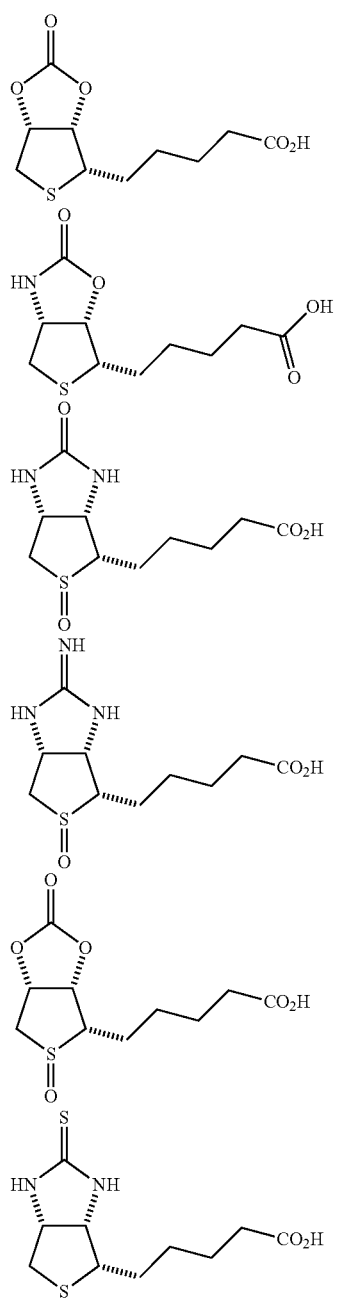
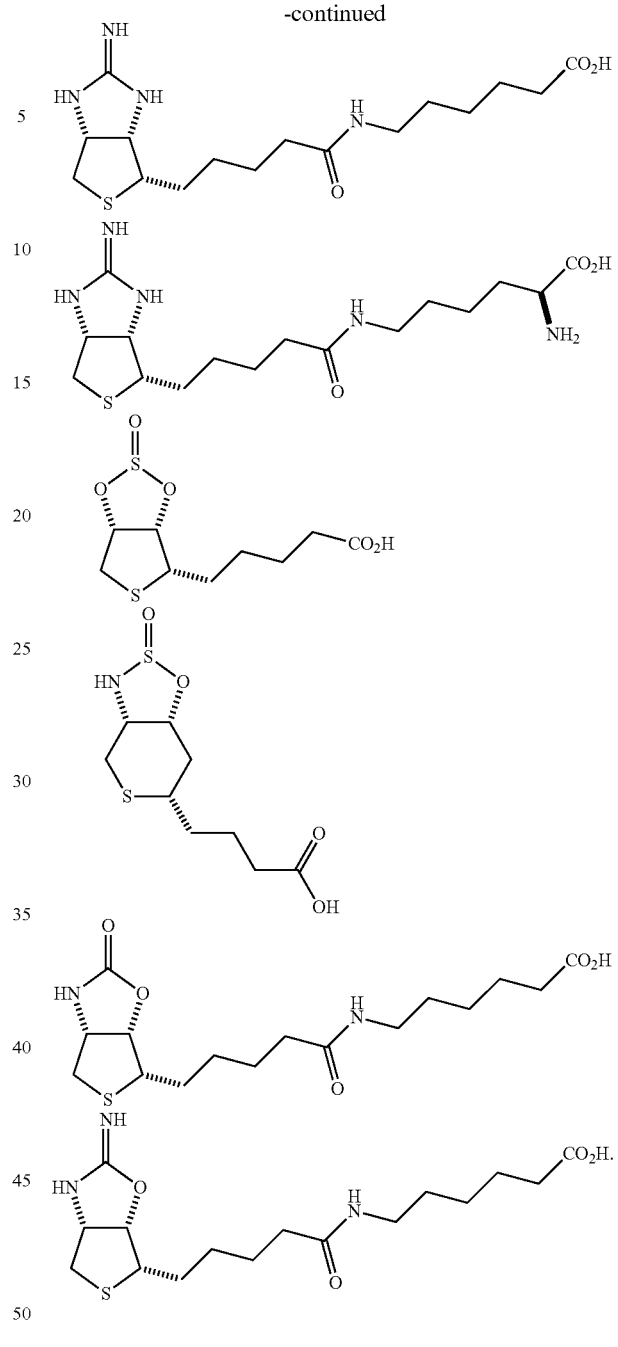
* * * * *

UNITED STATES PATENT AND TRADEMARK OFFICE
CERTIFICATE OF CORRECTION

PATENT NO. : 9,670,255 B2
APPLICATION NO. : 14/768916
DATED : June 6, 2017
INVENTOR(S) : A. Sugiyama et al.

It is certified that error appears in the above-identified patent and that said Letters Patent is hereby corrected as shown below:

On the Title Page

At (56) References Cited, FOREIGN PATENT DOCUMENTS, please add -- CN 102325884 1/2012 --.

In the Claims

In Column 76, Line 36 (Claim 7, Line 5) please change "claim 4" to -- claim 1 --.

In Column 76, Line 56 (Claim 7, Line 11) please change "$S_+\text{-}O^-$" to -- $S^+\text{-}O^-$ --.

In Column 76, Line 64 (Claim 8, Line 5) please change "claim 4" to -- claim 1 --.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*